United States Patent
Frewin et al.

(10) Patent No.: US 7,541,443 B2
(45) Date of Patent: Jun. 2, 2009

(54) ANTI-CD4 ANTIBODIES

(75) Inventors: Mark Frewin, Oxford (GB); Herman Waldmann, Oxford (GB); Scott Gorman, Witney (GB); Geoff Hale, Marston (GB); Patricia Rao, Acton, MA (US); Tadeusz Kornaga, Cambridge, MA (US); Douglas Ringler, Boston, MA (US); Stephen Cobbold, Witney (GB); Dawn Winsor-Hines, Framingham, MA (US)

(73) Assignees: Tolerrx, Inc., Cambridge, MA (US); Isis Innovation, Ltd., Oxford (GB); Cambridge University Technical Services, Ltd., Cambridge (GB)

( * ) Notice: Subject to any disclaimer, the term of this patent is extended or adjusted under 35 U.S.C. 154(b) by 605 days.

(21) Appl. No.: 10/353,708

(22) Filed: Jan. 29, 2003

(65) Prior Publication Data

US 2003/0219403 A1    Nov. 27, 2003

Related U.S. Application Data

(63) Continuation-in-part of application No. 10/171,452, filed on Jun. 13, 2002, now abandoned.

(60) Provisional application No. 60/345,194, filed on Oct. 19, 2001, provisional application No. 60/373,470, filed on Apr. 18, 2002, provisional application No. 60/373,471, filed on Apr. 18, 2002.

(30) Foreign Application Priority Data

Jun. 14, 2001  (GB) ................................ 0114517.6
Sep. 20, 2001  (GB) ................................ 0122724.8

(51) Int. Cl.
    *C07K 16/28*    (2006.01)
(52) U.S. Cl. ................ 530/388.75; 530/387.3
(58) Field of Classification Search ............ None
    See application file for complete search history.

(56) References Cited

U.S. PATENT DOCUMENTS

| 5,859,205 A | * | 1/1999 | Adair et al. ............... 530/387.3 |
| 6,056,956 A | * | 5/2000 | Cobbold et al. .......... 424/144.1 |
| 2003/0170239 A1 | * | 9/2003 | Hering et al. ............ 424/144.1 |

FOREIGN PATENT DOCUMENTS

| WO | WO90/15152 | 12/1990 |
| WO | WO96/36359 | 11/1996 |

OTHER PUBLICATIONS

Winsor-Hines et al., J Immunol. Oct. 1, 2004;173(7):4715-23.*
Gimsa et al., Cytokine. Mar. 1999;11(3):208-15.*
Paitier-Tonneau et al., Leucocyte Typing V, "Characterization of 18 Workshop anti-CD4 mAb; epitope mapping to CD4 mutants and effects on CD4-HLA class II interaction", Schlossman et al. eds., Garland Publishing, Inc., 1995.*
Paitier-Tonneau et al., Leucocyte Typing VI, "CD4 workshop panel report", Kishimoto et al. eds., Garland Publishing, Inc., 1998.*
Rudikoff et al., Proc. Natl. Acad. Sci. USA, 79: 1979-1 983, Mar. 1982.*
Phillips et al., J Immunol. Aug. 15, 2000;165(4):1949-55.*
Chien et al., Proc Natl Acad Sci U S A. Jul. 1989;86(14):5532-6.*
Colman P. M., Research in Immunology, 145:33-36, 1994.*
Eduardo Padlan, Mol Immunol. Feb. 1994;31(3):169-217.*
Portlolano et al., J Immunol. Feb. 1, 1993;150(3):880-7.*
Jefferies et al., Immunol Rev. Jun. 1998;163:59-76.*
Stumbles, et al., *J. Exp. Med.*, vol. 182, pp. 5-13 (Jul. 1995).
Isaacs, et al., *Clin. Exp. Immunol.*, vol. 110, pp. 158-166 (1997).
Stepheus, et al., *Eur. J. Immunol.*, vol. 31, pp. 1247-1254 (2001).
Mould, et al., Clin. Pharmacol. Ther., vol. 66, pp. 246-257 (1999).
Ng, et al., Pharmaceutical Research, vol. 23, No. 1, pp. 95-103(Jan. 2006).

* cited by examiner

*Primary Examiner*—Michail A Belyavskyi
*Assistant Examiner*—Zachary Skelding
(74) *Attorney, Agent, or Firm*—Raymond J. Lillie; Elliot M. Olstein

(57) ABSTRACT

Inducing tolerance in a primate by use of a compound, or a combination of at least two compounds, that has certain characteristics when tested in vitro. The compound, alone or in combination, is preferably TRX1 antibody and the compound or combination is preferably used in accordance with a specified dosing regimen.

13 Claims, 28 Drawing Sheets

FIGURE 1A
TRX1 Light Chain

```
ATG GAG ACA GAC ACA ATC CTG CTA TGG GTG CTG CTG CTC TGG GTT CCA GGC TCC ACT GGT GAC ATT GTG ATG ACC CAA TCT CCA GAT TCT TTG
 M   E   T   D   T   I   L   L   W   V   L   L   L   W   V   P   G   S   T   G   D   I   V   M   T   Q   S   P   D   S   L
<--------------------------Leader------------------------------------> <-----------------------FR1------------------

GCT GTG TCT CTA GGT GAG AGG GCC ACC ATC AAC TGC AAG GCC AGC CAA AGT GTT GAT TAT GAT GGT GAT AGT TAT ATG AAC TGG TAT CAA CAG
 A   V   S   L   G   E   R   A   T   I   N   C   K   A   S   Q   S   V   D   Y   D   G   D   S   Y   M   N   W   Y   Q   Q
-------------------------------------><--------------------------CDR1---------------------------> <---------------

AAA CCA GGA CAG CCA CCC AAA CTC CTC ATC TAT GTT GCA TCC AAT CTA GAG TCT GGG GTC CCA GAC AGG TTT AGT GGC AGT GGG TCT GGG ACA
 K   P   G   Q   P   P   K   L   L   I   Y   V   A   S   N   L   E   S   G   V   P   D   R   F   S   G   S   G   S   G   T
--------------------FR2-------------------> <----------CDR2----------> <---------------------------FR3--------------------

GAC TTC ACC CTC ACC ATC AGT TCT CTG CAG GCG GAG GAT GTT GCA GTC TAT TAC TGT CAG CAA AGT CTT CAG GAC CCT CCG ACG TTC GGT GGA
 D   F   T   L   T   I   S   S   L   Q   A   E   D   V   A   V   Y   Y   C   Q   Q   S   L   Q   D   P   P   T   F   G   G
------------------------------------------------------------------> <--------------CDR3------------> <----------

GGT ACC AAG GTG GAA ATC AAA CGA ACT GTG GCT GCA CCA TCT GTC TTC ATC TTC CCG CCA TCT GAT GAG CAG TTG AAA TCT GGA ACT GCC TCT
 G   T   K   V   E   I   K   R   T   V   A   A   P   S   V   F   I   F   P   P   S   D   E   Q   L   K   S   G   T   A   S
------------FR4----------> <------------------------------------Constant------------------------------------

GTT GTG TGC CTG CTG AAT AAC TTC TAT CCC AGA GAG GCC AAA GTA CAG TGG AAG GTG GAT AAC GCC CTC CAA TCG GGT AAC TCC CAG GAG AGT
 V   V   C   L   L   N   N   F   Y   P   R   E   A   K   V   Q   W   K   V   D   N   A   L   Q   S   G   N   S   Q   E   S
-----------------------------------------------------------------------------------------------------------

GTC ACA GAG CAG GAC AGC AAG GAC AGC ACC TAC AGC CTC AGC AGC ACC CTG ACG CTG AGC AAA GCA GAC TAC GAG AAA CAC AAA GTC TAC GCC
 V   T   E   Q   D   S   K   D   S   T   Y   S   L   S   S   T   L   T   L   S   K   A   D   Y   E   K   H   K   V   Y   A
-----------------------------------------------------------------------------------------------------------

TGC GAA GTC ACC CAT CAG GGC CTG AGC TCG CCC GTC ACA AAG AGC TTC AAC AGG GGA GAG TGT TAG
 C   E   V   T   H   Q   G   L   S   S   P   V   T   K   S   F   N   R   G   E   C   *
-----------------------------------------------------------------------------------> 
```

FIGURE 1B
TRX1 Light Chain Nucleic Acid Sequence

ATGGAGACAGACACAATCCTGCTATGGGTGCTGCTGCTCTGGGTTCCAGGCTCCACTGGTGACAT
TGTGATGACCCAATCTCCAGATTCTTTGGCTGTGTCTCTAGGTGAGAGGGCCACCATCAACTGCAAG
GCCAGCCAAAGTGTTGATTATGATGGTGATAGTTATATGAACTGGTATCAACAGAAACCAGGACAG
CCACCCAAACTCCTCATCTATGTTGCATCCAATCTAGAGTCTGGGGTCCCAGACAGGTTTAGTGG
CAGTGGGTCTGGGACAGACTTCACCCTCACCATCAGTTCTCTGCAGGCGGAGGATGTTGCAGTCT
ATTACTGTCAGCAAAGTCTTCAGGACCCTCCGACGTTCGGTGGAGGTACCAAGGTGGAAATCAAA
CGAACTGTGGCTGCACCATCTGTCTTCATCTTCCCGCCATCTGATGAGCAGTTGAAATCTGGAACT
GCCTCTGTTGTGTGCCTGCTGAATAACTTCTATCCCAGAGAGGCCAAAGTACAGTGGAAGGTGGAT
AACGCCCTCCAATCGGGTAACTCCCAGGAGAGTGTCACAGAGCAGGACAGCAAGGACAGCACCTA
CAGCCTCAGCACACCCTGACGCTGAGCAAAGCAGACTACGAGAAACACAAAGTCTACGCCTGCG
AAGTCACCCATCAGGGCCTGAGCTCGCCCGTCACAAAGAGCTTCAACAGGGGAGAGTGTTAG

FIGURE 1C
TRX1 Light Chain Amino Acid Sequence with CDRs Highlighted

With leader sequence:

METDTILLWVLLLWVPGSTGDIVMTQSPDSLAVSLGERATINCKASQSVDYDGDSYMNWYQQKPG
QPPKLLIYVASNLESGVPDRFSGSGSGTDFTLTISSLQAEDVAVYYCQQSLQDPPTFGGGTKVEIKR
TVAAPSVFIFPPSDEQLKSGTASVVCLLNNFYPREAKVQWKVDNALQSGNSQESVTEQDSKDSTYSL
SSTLTLSKADYEKHKVYACEVTHQGLSSPVTKSFNRGEC

Without leader sequence:

DIVMTQSPDSLAVSLGERATINCKASQSVDYDGDSYMNWYQQKPGQPPKLLIYVASNLESGVPDR
FSGSGSGTDFTLTISSLQAEDVAVYYCQQSLQDPPTFGGGTKVEIKRTVAAPSVFIFPPSDEQLKSGT
ASVVCLLNNFYPREAKVQWKVDNALQSGNSQESVTEQDSKDSTYSLSSTLTLSKADYEKHKVYACEV
THQGLSSPVTKSFNRGEC

FIGURE 1D
TRX1 Heavy Chain

```
ATG GAA TGG ATC TGG ATC TTT CTC CTC ATC CTG TCA GGA ACT CGA GGT GTC CAG TCC CAG GTT CAG CTG GTG CAG TCT GGA GCT GAA GTG AAG
 M   E   W   I   W   I   F   L   L   I   L   S   G   T   R   G   V   Q   S   Q   V   Q   L   V   Q   S   G   A   E   V   K
<--------------------------------Leader-------------------------------> <-------------------FR1----------------------
AAG CCT GGG GCT TCA GTG AAG GTG TCC TGT AAG GCT TCT GGA TAC ACA TTC ACT GCC TAT GTT ATA AGC TGG GTG AGG CAG GCA CCT GGA CAG
 K   P   G   A   S   V   K   V   S   C   K   A   S   G   Y   T   F   T   A   Y   V   I   S   W   V   R   Q   A   P   G   Q
-----------------------------------------------------------> <------CDR1-------> <------------FR2---------------

GGC CTT GAG TGG ATG GGA GAG ATT TAT CCT GGA AGC GGT AGT AGT TAT TAT AAT GAG AAG TTC AAG GGC AGG GTC ACA ATG ACT AGA GAC ACA
 G   L   E   W   M   G   E   I   Y   P   G   S   G   S   S   Y   Y   N   E   K   F   K   G   R   V   T   M   T   R   D   T
----------------------> <---------------------------CDR2-----------------------------> <--------------------------------

TCC ACC AGC ACA GTC TAC ATG GAA CTC AGC AGC CTG AGG TCT GAG GAC ACT GCG GTC TAT TAC TGT GCA AGA TCC GGG GAC GGC AGT CGG TTT
 S   T   S   T   V   Y   M   E   L   S   S   L   R   S   E   D   T   A   V   Y   Y   C   A   R   S   G   D   G   S   R   F
-------------------------FR3----------------------------------------------> <-------------CDR3---------

GTT TAC TGG GGC CAA GGG ACA CTA GTC ACA GTC TCC TCA GCC TCC ACC AAG GGC CCA TCG GTC TTC CCC CTG GCA CCC TCC TCC AAG AGC ACC
 V   Y   W   G   Q   G   T   L   V   T   V   S   S   A   S   T   K   G   P   S   V   F   P   L   A   P   S   S   K   S   T
------> <-----------------FR4----------------> <-------------------------Constant------------------------------

TCT GGG GGC ACA GCG GCC CTG GGC TGC CTG GTC AAG GAC TAC TTC CCC GAA CCG GTG ACG GTG TCG TGG AAC TCA GGC GCC CTG ACC AGC GGC
 S   G   G   T   A   A   L   G   C   L   V   K   D   Y   F   P   E   P   V   T   V   S   W   N   S   G   A   L   T   S   G
-------------------------------------------------------------------------------------------------------------------

GTG CAC ACC TTC CCG GCT GTC CTA CAG TCC TCA GGA CTC TAC TCC CTC AGC AGC GTG GTG ACC GTG CCC TCC AGC AGC TTG GGC ACC CAG ACC
 V   H   T   F   P   A   V   L   Q   S   S   G   L   Y   S   L   S   S   V   V   T   V   P   S   S   S   L   G   T   Q   T
-------------------------------------------------------------------------------------------------------------------

TAC ATC TGC AAC GTG AAT CAC AAG CCC AGC AAC ACC AAG GTG GAC AAG AAA GTT GAG CCC AAA TCT TGT GAC AAA ACT CAC ACA TGC CCA CCG
 Y   I   C   N   V   N   H   K   P   S   N   T   K   V   D   K   K   V   E   P   K   S   C   D   K   T   H   T   C   P   P
-------------------------------------------------------------------------------------------------------------------

TGC CCA GCA CCT GAA CTC GCG GGG GCA CCG TCA GTC TTC CTC TTC CCC CCA AAA CCC AAG GAC ACC CTC ATG ATC TCC CGG ACC CCT GAG GTC
 C   P   A   P   E   L   A   G   A   P   S   V   F   L   F   P   P   K   P   K   D   T   L   M   I   S   R   T   P   E   V
-------------------------------------------------------------------------------------------------------------------

ACA TGC GTG GTG GTG GAC GTG AGC CAC GAA GAC CCT GAG GTC AAG TTC AAC TGG TAC GTG GAC GGC GTG GAG GTG CAT AAT GCC AAG ACA AAG
 T   C   V   V   V   D   V   S   H   E   D   P   E   V   K   F   N   W   Y   V   D   G   V   E   V   H   N   A   K   T   K
-------------------------------------------------------------------------------------------------------------------

CCG CGG GAG GAG CAG TAC AAC AGC ACG TAC CGT GTG GTC AGC GTC CTC ACC GTC CTG CAC CAG GAC TGG CTG AAT GGC AAG GAG TAC AAG TGC
 P   R   E   E   Q   Y   N   S   T   Y   R   V   V   S   V   L   T   V   L   H   Q   D   W   L   N   G   K   E   Y   K   C
-------------------------------------------------------------------------------------------------------------------

AAG GTC TCC AAC AAA GCC CTC CCA GCC CCC ATC GAG AAA ACC ATC TCC AAA GCC AAA GGG CAG CCC CGA GAA CCA CAG GTG TAC ACC CTG CCC
 K   V   S   N   K   A   L   P   A   P   I   E   K   T   I   S   K   A   K   G   Q   P   R   E   P   Q   V   Y   T   L   P
-------------------------------------------------------------------------------------------------------------------

CCA TCC CGG GAT GAG CTG ACC AAG AAC CAG GTC AGC CTG ACC TGC CTG GTC AAA GGC TTC TAT CCC AGC GAC ATC GCC GTG GAG TGG GAG AGC
 P   S   R   D   E   L   T   K   N   Q   V   S   L   T   C   L   V   K   G   F   Y   P   S   D   I   A   V   E   W   E   S
-------------------------------------------------------------------------------------------------------------------

AAT GGG CAG CCG GAG AAC AAC TAC AAG ACC ACG CCT CCC GTG CTG GAC TCC GAC GGC TCC TTC TTC CTC TAC AGC AAG CTC ACC GTG GAC AAG
 N   G   Q   P   E   N   N   Y   K   T   T   P   P   V   L   D   S   D   G   S   F   F   L   Y   S   K   L   T   V   D   K
-------------------------------------------------------------------------------------------------------------------

AGC AGG TGG CAG CAG GGG AAC GTC TTC TCA TGC TCC GTG ATG CAT GAG GCT CTG CAC AAC CAC TAC ACG CAG AAG AGC CTC TCC CTG TCT CCG
 S   R   W   Q   Q   G   N   V   F   S   C   S   V   M   H   E   A   L   H   N   H   Y   T   Q   K   S   L   S   L   S   P
-------------------------------------------------------------------------------------------------------------------

GGT AAA TGA
 G   K   *
---------->
```

FIGURE 1E

TRX1 Heavy Chain Nucleic Acid Sequence

ATGGAATGGATCTGGATCTTTCTCCTCATCCTGTCAGGAACTCGAGGTGTCCAGTCC
CAGGTTCAGCTGGTGCAGTCTGGAGCTGAAGTGAAGAAGCCTGGGGCTTCAGTGA
AGGTGTCCTGTAAGGCTTCTGGATACACATTCACTGCCTATGTTATAAGCTGGGTGA
GGCAGGCACCTGGACAGGGCCTTGAGTGGATGGGAGAGATTTATCCTGGAAGCGG
TAGTAGTTATTATAATGAGAAGTTCAAGGGCAGGGTCACAATGACTAGAGACACATC
CACCAGCACAGTCTACATGGAACTCAGCAGCCTGAGGTCTGAGGACACTGCGGTCT
ATTACTGTGCAAGATCCGGGGACGGCAGTCGGTTTGTTTACTGGGGCCAAGGGACA
CTAGTCACAGTCTCCTCAGCCTCCACCAAGGGCCCATCGGTCTTCCCCCTGGCACC
CTCCTCCAAGAGCACCTCTGGGGGCACAGCGGCCCTGGGCTGCCTGGTCAAGGAC
TACTTCCCCGAACCGGTGACGGTGTCGTGGAACTCAGGCGCCCTGACCAGCGGCG
TGCACACCTTCCCGGCTGTCCTACAGTCCTCAGGACTCTACTCCCTCAGCAGCGTG
GTGACCGTGCCCTCCAGCAGCTTGGGCACCCAGACCTACATCTGCAACGTGAATCA
CAAGCCCAGCAACACCAAGGTGGACAAGAAAGTTGAGCCCAAATCTTGTGACAAAA
CTCACACATGCCCACCGTGCCCAGCACCTGAACTCGCGGGGGCACCGTCAGTCTT
CCTCTTCCCCCCAAAACCCAAGGACACCCTCATGATCTCCCGGACCCCTGAGGTCA
CATGCGTGGTGGTGGACGTGAGCCACGAAGACCCTGAGGTCAAGTTCAACTGGTA
CGTGGACGGCGTGGAGGTGCATAATGCCAAGACAAAGCCGCGGGAGGAGCAGTAC
AACAGCACGTACCGTGTGGTCAGCGTCCTCACCGTCCTGCACCAGGACTGGCTGA
ATGGCAAGGAGTACAAGTGCAAGGTCTCCAACAAAGCCCTCCCAGCCCCCATCGAG
AAAACCATCTCCAAAGCCAAAGGGCAGCCCCGAGAACCACAGGTGTACACCCTGCC
CCCATCCCGGGATGAGCTGACCAAGAACCAGGTCAGCCTGACCTGCCTGGTCAAA
GGCTTCTATCCCAGCGACATCGCCGTGGAGTGGGAGAGCAATGGGCAGCCGGAGA
ACAACTACAAGACCACGCCTCCCGTGCTGGACTCCGACGGCTCCTTCTTCCTCTAC
AGCAAGCTCACCGTGGACAAGAGCAGGTGGCAGCAGGGGAACGTCTTCTCATGCT
CCGTGATGCATGAGGCTCTGCACAACCACTACACGCAGAAGAGCCTCTCCCTGTCT
CCGGGTAAATGA

FIGURE 1F
TRX1 Heavy Chain Amino Acid Sequence with CDRs Highlighted

With leader sequence:

MEWIWIFLLILSGTRGVQSQVQLVQSGAEVKKPGASVKVSCKASGYTFTAYVISWVRQAPGQGLEW
MGEIYPGSGSSYYNEKFKGRVTMTRDTSTSTVYMELSSLRSEDTAVYYCARSGDGSRFVYWGQG
TLVTVSSASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELAGAPSVFLFPPKPK
DTLMISRTPEVTCVVVDVSHEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNHYTQKSLSLSPGK

Without leader sequence:

QVQLVQSGAEVKKPGASVKVSCKASGYTFTAYVISWVRQAPGQGLEWMG**EIYPGSGSSYYNEKF
KGRVTMTRDTSTSTVYMELSSLRSEDTAVYYCARSGDGSRFVY**WGQGTLVTVSSASTKGPSVFPLA
PSSKSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELAGAPSVFLFPPKPKDTLMISRTPEVTCVVVDVSHE
DPEVKFNWYVDGVEVHNAKTKPREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQPENNYKTTPPVLDSDGSFFLY
SKLTVDKSRWQQGNVFSCSVMHEALHNHYTQKSLSLSPGK

FIGURE 2A

TRX1 Light Chain

```
ATG GAG ACA GAC ACA ATC CTG CTA TGG GTG CTG CTG CTC TGG GTT CCA GGC TCC ACT GGT GAC ATT GTG ATG ACC CAA TCT CCA GAT TCT TTG
 M   E   T   D   T   I   L   L   W   V   L   L   L   W   V   P   G   S   T   G   D   I   V   M   T   Q   S   P   D   S   L
<------------------------Leader------------------------------------> <-----------------------FR1-----------------

GCT GTG TCT CTA GGT GAG AGG GCC ACC ATC AAC TGC AAG GCC AGC CAA AGT GTT GAT TAT GAT GGT GAT AGT TAT ATG AAC TGG TAT CAA CAG
 A   V   S   L   G   E   R   A   T   I   N   C   K   A   S   Q   S   V   D   Y   D   G   D   S   Y   M   N   W   Y   Q   Q
-----------------------------------------------><-----------------------CDR1-----------------------------> <---------------

AAA CCA GGA CAG CCA CCC AAA CTC CTC ATC TAT GTT GCA TCC AAT CTA GAG TCT GGG GTC CCA GAC AGG TTT AGT GGC AGT GGG TCT GGG ACA
 K   P   G   Q   P   P   K   L   L   I   Y   V   A   S   N   L   E   S   G   V   P   D   R   F   S   G   S   G   S   G   T
-------------------FR2---------------------> <----------CDR2----------> <------------------------FR3---------------------

GAC TTC ACC CTC ACC ATC AGT TCT CTG CAG GCG GAG GAT GTT GCA GTC TAT TAC TGT CAG CAA AGT CTT CAG GAC CCT CCG ACG TTC GGT GGA
 D   F   T   L   T   I   S   S   L   Q   A   E   D   V   A   V   Y   Y   C   Q   Q   S   L   Q   D   P   P   T   F   G   G
-----------------------------------------------------------------> <----------------CDR3--------------> <----------

GGT ACC AAG GTG GAA ATC AAA CGA ACT GTG GCT GCA CTA TCT GTC TTC ATC TTC CCG CCA TCT GAT GAG CAG TTG AAA TCT GGA ACT GCC TCT
 G   T   K   V   E   I   K   R   T   V   A   A   L   S   V   F   I   F   P   P   S   D   E   Q   L   K   S   G   T   A   S
-----------FR4----------> <---------------------------Constant-----------------------------------------

GTT GTG TGC CTG CTG AAT AAC TTC TAT CCC AGA GAG GCC AAA GTA CAG TGG AAG GTG GAT AAC GCC CTC CAA TCG GGT AAC TCC CAG GAG AGT
 V   V   C   L   L   N   N   F   Y   P   R   E   A   K   V   Q   W   K   V   D   N   A   L   Q   S   G   N   S   Q   E   S
-------------------------------------------------------------------------------------------------------

GTC ACA GAG CAG GAC AGC AAG GAC AGC ACC TAC AGC CTC AGC AGC ACC CTG ACG CTG AGC AAA GCA GAC TAC GAG AAA CAC AAA GTC TAC GCC
 V   T   E   Q   D   S   K   D   S   T   Y   S   L   S   S   T   L   T   L   S   K   A   D   Y   E   K   H   K   V   Y   A
-------------------------------------------------------------------------------------------------------

TGC GAA GTC ACC CAT CAG GGC CTG AGC TCG CCC GTC ACA AAG AGC TTC AAC AGG GGA GAG TGT TAG
 C   E   V   T   H   Q   G   L   S   S   P   V   T   K   S   F   N   R   G   E   C   *
-----------------------------------------------------------------------------------> 
```

FIGURE 2B

TRX1 Light Chain Nucleic Acid Sequence

ATGGAGACAGACACAATCCTGCTATGGGTGCTGCTGCTCTGGGTTCC
AGGCTCCACTGGTGACATTGTGATGACCCAATCTCCAGATTCTTTGGC
TGTGTCTCTAGGTGAGAGGGCCACCATCAACTGCAAGGCCAGCCAAA
GTGTTGATTATGATGGTGATAGTTATATGAACTGGTATCAACAGAAAC
CAGGACAGCCACCCAAACTCCTCATCTATGTTGCATCCAATCTAGAGT
CTGGGGTCCCAGACAGGTTTAGTGGCAGTGGGTCTGGGACAGACTTC
ACCCTCACCATCAGTTCTCTGCAGGCGGAGGATGTTGCAGTCTATTAC
TGTCAGCAAAGTCTTCAGGACCCTCCGACGTTCGGTGGAGGTACCAA
GGTGGAAATCAAACGAACTGTGGCTGCACTATCTGTCTTCATCTTCCC
GCCATCTGATGAGCAGTTGAAATCTGGAACTGCCTCTGTTGTGTGCCT
GCTGAATAACTTCTATCCCAGAGAGGCCAAAGTACAGTGGAAGGTGG
ATAACGCCCTCCAATCGGGTAACTCCCAGGAGAGTGTCACAGAGCAG
GACAGCAAGGACAGCACCTACAGCCTCAGCAGCACCCTGACGCTGAG
CAAAGCAGACTACGAGAAACACAAAGTCTACGCCTGCGAAGTCACCC
ATCAGGGCCTGAGCTCGCCCGTCACAAAGAGCTTCAACAGGGGAGAG
TGTTAG

FIGURE 2C

TRX1 Light Chain Amino Acid Sequence with CDRs Highlighted

With leader sequence:

METDTILLWVLLLWVPGSTGDIVMTQSPDSLAVSLGERATINCKASQSVDYDGDSYMNWYQQKP
GQPPKLLIYVASNLESGVPDRFSGSGSGTDFTLTISSLQAEDVAVYYCQQSLQDPPTFGGGTKVEI
KRTVAALSVFIFPPSDEQLKSGTASVVCLLNNFYPREAKVQWKVDNALQSGNSQESVTEQDSKDS
TYSLSSTLTLSKADYEKHKVYACEVTHQGLSSPVTKSFNRGEC

Without leader sequence:

DIVMTQSPDSLAVSLGERATINCKASQSVDYDGDSYMNWYQQKPGQPPKLLIYVASNLESGVPDR
FSGSGSGTDFTLTISSLQAEDVAVYYCQQSLQDPPTFGGGTKVEIKRTVAALSVFIFPPSDEQLKSG
TASVVCLLNNFYPREAKVQWKVDNALQSGNSQESVTEQDSKDSTYSLSSTLTLSKADYEKHKVY
ACEVTHQGLSSPVTKSFNRGEC

FIGURE 2D
TRX1 Heavy Chain
(aglycosyl)

```
ATG GAA TGG ATC TGG ATC TTT CTC CTC ATC CTG TCA GGA ACT CGA GGT GTC CAG TCC CAG GTT CAG CTG GTG CAG TCT GGA GCT GAA GTG AAG
 M   E   W   I   W   I   F   L   L   I   L   S   G   T   R   G   V   Q   S   Q   V   Q   L   V   Q   S   G   A   E   V   K
<--------------------------Leader-----------------------------> <--------------------FR1----------------------

AAG CCT GGG GCT TCA GTG AAG GTG TCC TGT AAG GCT TCT GGA TAC ACA TTC ACT GCC TAT GTT ATA AGC TGG GTG AGG CAG GCA CCT GGA CAG
 K   P   G   A   S   V   K   V   S   C   K   A   S   G   Y   T   F   T   A   Y   V   I   S   W   V   R   Q   A   P   G   Q
-------------------------------------------------------------> <------CDR1-------> <-----------FR2---------------

GGC CTT GAG TGG ATG GGA GAG ATT TAT CCT GGA AGC GGT AGT AGT TAT TAT AAT GAG AAG TTC AAG GGC AGG GTC ACA ATG ACT AGA GAC ACA
 G   L   E   W   M   G   E   I   Y   P   G   S   G   S   S   Y   Y   N   E   K   F   K   G   R   V   T   M   T   R   D   T
--------------------> <----------------------------CDR2---------------------------> <---------------------

TCC ACC AGC ACA GTC TAC ATG GAA CTC AGC AGC CTG AGG TCT GAG GAC ACT GCG GTC TAT TAC TGT GCA AGA TCC GGG GAC GGC AGT CGG TTT
 S   T   S   T   V   Y   M   E   L   S   S   L   R   S   E   D   T   A   V   Y   Y   C   A   R   S   G   D   G   S   R   F
------------------------------FR3------------------------------------------------> <------------CDR3---------

GTT TAC TGG GGC CAA GGG ACA CTA GTC ACA GTC TCC TCA GCC TCC ACC AAG GGC CCA TCG GTC TTC CCC CTG GCA CCC TCC TCC AAG AGC ACC
 V   Y   W   G   Q   G   T   L   V   T   V   S   S   A   S   T   K   G   P   S   V   F   P   L   A   P   S   S   K   S   T
------> <-----------------FR4-------------------> <----------------------------Constant--------------------------

TCT GGG GGC ACA GCG GCC CTG GGC TGC CTG GTC AAG GAC TAC TTC CCC GAA CCG GTG ACG GTG TCG TGG AAC TCA GGC GCC CTG ACC AGC GGC
 S   G   G   T   A   A   L   G   C   L   V   K   D   Y   F   P   E   P   V   T   V   S   W   N   S   G   A   L   T   S   G

GTG CAC ACC TTC CCG GCT GTC CTA CAG TCC TCA GGA CTC TAC TCC CTC AGC AGC GTG GTG ACC GTG CCC TCC AGC AGC TTG GGC ACC CAG ACC
 V   H   T   F   P   A   V   L   Q   S   S   G   L   Y   S   L   S   S   V   V   T   V   P   S   S   S   L   G   T   Q   T

TAC ATC TGC AAC GTG AAT CAC AAG CCC AGC AAC ACC AAG GTG GAC AAG AAA GTT GAG CCC AAA TCT TGT GAC AAA ACT CAC ACA TGC CCA CCG
 Y   I   C   N   V   N   H   K   P   S   N   T   K   V   D   K   K   V   E   P   K   S   C   D   K   T   H   T   C   P   P

TGC CCA GCA CCT GAA CTC CTG GGG GGA CCG TCA GTC TTC CTC TTC CCC CCA AAA CCC AAG GAC ACC CTC ATG ATC TCC CGG ACC CCT GAG GTC
 C   P   A   P   E   L   L   G   G   P   S   V   F   L   F   P   P   K   P   K   D   T   L   M   I   S   R   T   P   E   V

ACA TGC GTG GTG GTG GAC GTG AGC CAC GAA GAC CCT GAG GTC AAG TTC AAC TGG TAC GTG GAC GGC GTG GAG GTG CAT AAT GCC AAG ACA AAG
 T   C   V   V   V   D   V   S   H   E   D   P   E   V   K   F   N   W   Y   V   D   G   V   E   V   H   N   A   K   T   K

CCG CGG GAG GAG CAG TAC GCC AGC ACG TAC CGT GTG GTC AGC GTC CTC ACC GTC CTG CAC CAG GAC TGG CTG AAT GGC AAG GAG TAC AAG TGC
 P   R   E   E   Q   Y   A   S   T   Y   R   V   V   S   V   L   T   V   L   H   Q   D   W   L   N   G   K   E   Y   K   C

AAG GTC TCC AAC AAA GCC CTC CCA GCC CCC ATC GAG AAA ACC ATC TCC AAA GCC AAA GGG CAG CCC CGA GAA CCA CAG GTG TAC ACC CTG CCC
 K   V   S   N   K   A   L   P   A   P   I   E   K   T   I   S   K   A   K   G   Q   P   R   E   P   Q   V   Y   T   L   P

CCA TCC CGG GAT GAG CTG ACC AAG AAC CAG GTC AGC CTG ACC TGC CTG GTC AAA GGC TTC TAT CCC AGC GAC ATC GCC GTG GAG TGG GAG AGC
 P   S   R   D   E   L   T   K   N   Q   V   S   L   T   C   L   V   K   G   F   Y   P   S   D   I   A   V   E   W   E   S

AAT GGG CAG CCG GAG AAC AAC TAC AAG ACC ACG CCT CCC GTG CTG GAC TCC GAC GGC TCC TTC TTC CTC TAC AGC AAG CTC ACC GTG GAC AAG
 N   G   Q   P   E   N   N   Y   K   T   T   P   P   V   L   D   S   D   G   S   F   F   L   Y   S   K   L   T   V   D   K

AGC AGG TGG CAG CAG GGG AAC GTC TTC TCA TGC TCC GTG ATG CAT GAG GCT CTG CAC AAC CAC TAC ACG CAG AAG AGC CTC TCC CTG TCT CCG
 S   R   W   Q   Q   G   N   V   F   S   C   S   V   M   H   E   A   L   H   N   H   Y   T   Q   K   S   L   S   L   S   P

GGT AAA TGA
 G   K   *              ---------->
```

FIGURE 2E

TRX1 aglycosyl mut Heavy Chain Nucleic Acid Sequence

ATGGAATGGATCTGGATCTTTCTCCTCATCCTGTCAGGAACTCGAGGTGTCCAGTCCCAG
GTTCAGCTGGTGCAGTCTGGAGCTGAAGTGAAGAAGCCTGGGGCTTCAGTGAAGGTGTC
CTGTAAGGCTTCTGGATACACATTCACTGCCTATGTTATAAGCTGGGTGAGGCAGGCACC
TGGACAGGGCCTTGAGTGGATGGGAGAGATTTATCCTGGAAGCGGTAGTAGTTATTATAA
TGAGAAGTTCAAGGGCAGGGTCACAATGACTAGAGACACATCCACCAGCACAGTCTACAT
GGAACTCAGCAGCCTGAGGTCTGAGGACACTGCGGTCTATTACTGTGCAAGATCCGGGG
ACGGCAGTCGGTTTGTTTACTGGGGCCAAGGGACACTAGTCACAGTCTCCTCAGCCTCCA
CCAAGGGCCCATCGGTCTTCCCCCTGGCACCCTCCTCCAAGAGCACCTCTGGGGGCACA
GCGGCCCTGGGCTGCCTGGTCAAGGACTACTTCCCCGAACCGGTGACGGTGTCGTGGA
ACTCAGGCGCCCTGACCAGCGGCGTGCACACCTTCCCGGCTGTCCTACAGTCCTCAGGA
CTCTACTCCCTCAGCAGCGTGGTGACCGTGCCCTCCAGCAGCTTGGGCACCCAGACCTA
CATCTGCAACGTGAATCACAAGCCCAGCAACACCAAGGTGGACAAGAAAGTTGAGCCCA
AATCTTGTGACAAAACTCACACATGCCCACCGTGCCCAGCACCTGAACTCCTGGGGGGA
CCGTCAGTCTTCCTCTTCCCCCCAAAACCCAAGGACACCCTCATGATCTCCCGGACCCCT
GAGGTCACATGCGTGGTGGTGGACGTGAGCCACGAAGACCCTGAGGTCAAGTTCAACTG
GTACGTGGACGGCGTGGAGGTGCATAATGCCAAGACAAAGCCGCGGGAGGAGCAGTAC
GCCAGCACGTACCGTGTGGTCAGCGTCCTCACCGTCCTGCACCAGGACTGGCTGAATGG
CAAGGAGTACAAGTGCAAGGTCTCCAACAAAGCCCTCCCAGCCCCCATCGAGAAAACCA
TCTCCAAAGCCAAAGGGCAGCCCCGAGAACCACAGGTGTACACCCTGCCCCCATCCCGG
GATGAGCTGACCAAGAACCAGGTCAGCCTGACCTGCCTGGTCAAAGGCTTCTATCCCAG
CGACATCGCCGTGGAGTGGGAGAGCAATGGGCAGCCGGAGAACAACTACAAGACCACG
CCTCCCGTGCTGGACTCCGACGGCTCCTTCTTCCTCTACAGCAAGCTCACCGTGGACAA
GAGCAGGTGGCAGCAGGGGAACGTCTTCTCATGCTCCGTGATGCATGAGGCTCTGCACA
ACCACTACACGCAGAAGAGCCTCTCCCTGTCTCCGGGTAAATGA

FIGURE 2F

TRX1 Heavy Chain aglycosyl mut Amino Acid Sequence with CDRs Highlighted

With leader sequence:

MEWIWIFLLILSGTRGVQSQVQLVQSGAEVKKPGASVKVSCKASGYTFTAYVISWVRQAPGQGLE
WMGEIYPGSGSSYYNEKFKGRVTMTRDTSTSTVYMELSSLRSEDTAVYYCARSGDGSRFVYWG
QGTLVTVSSASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYASTYRVVSVL
TVLHQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHNHYT
QKSLSLSPGK

Without leader sequence:

QVQLVQSGAEVKKPGASVKVSCKASGYTFTAYVISWVRQAPGQGLEWMG**EIYPGSGSSYYNEK
FKGRVTMTRDTSTSTVYMELSSLRSEDTAVYYCARSGDGSRFVY**WGQGTLVTVSSASTKGPSVFP
LAPSSKSTSGGTAALGCLVKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYASTYRVVSVLTVLHQDWLNGKEYKCKVS
NKALPAPIEKTISKAKGQPREPQVYTLPPSRDELTKNQVSLTCLVKGFYPSDIAVEWESNGQPENNY
KTTPPVLDSDGSFFLYSKLTVDKSRWQQGNVFSCSVMHEALHNHYTQKSLSLSPGK

FIGURE 3A
TRX1 Light Chain

```
ATG GAG ACA GAC ACA ATC CTG CTA TGG GTG CTG CTG CTC TGG GTT CCA GGC TCC ACT GGT GAC ATT GTG ATG ACC CAA TCT CCA GAT TCT TTG
 M   E   T   D   T   I   L   L   W   V   L   L   L   W   V   P   G   S   T   G   D   I   V   M   T   Q   S   P   D   S   L
<-------------------------------Leader-----------------------------------> <-----------------------FR1------------------

GCT GTG TCT CTA GGT GAG AGG GCC ACC ATC AAC TGC AAG GCC AGC CAA AGT GTT GAT TAT GAT GGT GAT AGT TAT ATG AAC TGG TAT CAA CAG
 A   V   S   L   G   E   R   A   T   I   N   C   K   A   S   Q   S   V   D   Y   D   G   D   S   Y   M   N   W   Y   Q   Q
----------------------------------------------------><-------------------------CDR1-----------------------> <-------------

AAA CCA GGA CAG CCA CCC AAA CTC CTC ATC TAT GTT GCA TCC AAT CTA GAG TCT GGG GTC CCA GAC AGG TTT AGT GGC AGT GGG TCT GGG ACA
 K   P   G   Q   P   P   K   L   L   I   Y   V   A   S   N   L   E   S   G   V   P   D   R   F   S   G   S   G   S   G   T
-----------------FR2--------------------> <-----------CDR2----------> <------------------------FR3--------------------

GAC TTC ACC CTC ACC ATC AGT TCT CTG CAG GCG GAG GAT GTT GCA GTC TAT TAC TGT CAG CAA AGT CTT CAG GAC CCT CCG ACG TTC GGT GGA
 D   F   T   L   T   I   S   S   L   Q   A   E   D   V   A   V   Y   Y   C   Q   Q   S   L   Q   D   P   P   T   F   G   G
-------------------------------------------------------------------> <----------------CDR3-------------> <----------

GGT ACC AAG GTG GAA ATC AAA CGA ACT GTG GCT GCA CTA TCT GTC TTC ATC TTC CCG CCA TCT GAT GAG CAG TTG AAA TCT GGA ACT GCC TCT
 G   T   K   V   E   I   K   R   T   V   A   A   L   S   V   F   I   F   P   P   S   D   E   Q   L   K   S   G   T   A   S
----------FR4-----------> <-----------------------------------Constant-----------------------------------------------

GTT GTG TGC CTG CTG AAT AAC TTC TAT CCC AGA GAG GCC AAA GTA CAG TGG AAG GTG GAT AAC GCC CTC CAA TCG GGT AAC TCC CAG GAG AGT
 V   V   C   L   L   N   N   F   Y   P   R   E   A   K   V   Q   W   K   V   D   N   A   L   Q   S   G   N   S   Q   E   S
--------------------------------------------------------------------------------------------------------------

GTC ACA GAG CAG GAC AGC AAG GAC AGC ACC TAC AGC CTC AGC AGC ACC CTG ACG CTG AGC AAA GCA GAC TAC GAG AAA CAC AAA GTC TAC GCC
 V   T   E   Q   D   S   K   D   S   T   Y   S   L   S   S   T   L   T   L   S   K   A   D   Y   E   K   H   K   V   Y   A
--------------------------------------------------------------------------------------------------------------

TGC GAA GTC ACC CAT CAG GGC CTG AGC TCG CCC GTC ACA AAG AGC TTC AAC AGG GGA GAG TGT TAG
 C   E   V   T   H   Q   G   L   S   S   P   V   T   K   S   F   N   R   G   E   C   *
--------------------------------------------------------------------------->
```

FIGURE 3B
TRX1 Light Chain Nucleic Acid Sequence

ATGGAGACAGACACAATCCTGCTATGGGTGCTGCTGCTCTGGGTTCCAGGCTCCACTGGTGACAT
TGTGATGACCCAATCTCCAGATTCTTTGGCTGTGTCTCTAGGTGAGAGGGCCACCATCAACTGCAAG
GCCAGCCAAAGTGTTGATTATGATGGTGATAGTTATATGAACTGGTATCAACAGAAACCAGGACAG
CCACCCAAACTCCTCATCTATGTTGCATCCAATCTAGAGTCTGGGGTCCCAGACAGGTTTAGTGG
CAGTGGGTCTGGGACAGACTTCACCCTCACCATCAGTTCTCTGCAGGCGGAGGATGTTGCAGTCT
ATTACTGTCAGCAAAGTCTTCAGGACCCTCCGACGTTCGGTGGAGGTACCAAGGTGGAAATCAAA
CGAACTGTGGCTGCACTATCTGTCTTCATCTTCCCGCCATCTGATGAGCAGTTGAAATCTGGAACT
GCCTCTGTTGTGTGCCTGCTGAATAACTTCTATCCCAGAGAGGCCAAAGTACAGTGGAAGGTGGATAA
CGCCCTCCAATCGGGTAACTCCCAGGAGAGTGTCACAGAGCAGGACAGCAAGGACAGCACCTACAGC
CTCAGCAGCACCCTGACGCTGAGCAAAGCAGACTACGAGAAACACAAAGTCTACGCCTGCGAAGTCA
CCCATCAGGGCCTGAGCTCGCCCGTCACAAAGAGCTTCAACAGGGGAGAGTGTTAG

FIGURE 3C
TRX1 Light Chain Amino Acid Sequence with CDRs Highlighted

With leader sequence:

METDTILLWVLLLWVPGSTGDIVMTQSPDSLAVSLGERATINCKASQSVDYDGDSYMNWYQQKPG
QPPKLLIYVASNLESGVPDRFSGSGSGTDFTLTISSLQAEDVAVYYCQQSLQDPPTFGGGTKVEIKR
TVAALSVFIFPPSDEQLKSGTASVVCLLNNFYPREAKVQWKVDNALQSGNSQESVTEQDSKDSTYSL
SSTLTLSKADYEKHKVYACEVTHQGLSSPVTKSFNRGEC

Without leader sequence:

DIVMTQSPDSLAVSLGERATINCKASQSVDYDGDSYMNWYQQKPGQPPKLLIYVASNLESGVPDR
FSGSGSGTDFTLTISSLQAEDVAVYYCQQSLQDPPTFGGGTKVEIKRTVAALSVFIFPPSDEQLKSGT
ASVVCLLNNFYPREAKVQWKVDNALQSGNSQESVTEQDSKDSTYSLSSTLTLSKADYEKHKVYACEV
THQGLSSPVTKSFNRGEC

FIGURE 3D
TRX1 Heavy Chain

```
ATG GAA TGG ATC TGG ATC TTT CTC CTC ATC CTG TCA GGA ACT CGA GGT GTC CAG TCC CAG GTT CAG CTG GTG CAG TCT GGA GCT GAA GTG AAG
 M   E   W   I   W   I   F   L   L   I   L   S   G   T   R   G   V   Q   S   Q   V   Q   L   V   Q   S   G   A   E   V   K
<--------------------------Leader----------------------------> <-------------------FR1--------------------
AAG CCT GGG GCT TCA GTG AAG GTG TCC TGT AAG GCT TCT GGA TAC ACA TTC ACT GCC TAT GTT ATA AGC TGG GTG AGG CAG GCA CCT GGA CAG
 K   P   G   A   S   V   K   V   S   C   K   A   S   G   Y   T   F   T   A   Y   V   I   S   W   V   R   Q   A   P   G   Q
------------------------------------------------------> <------CDR1-------> <------------FR2---------------

GGC CTT GAG TGG ATG GGA GAG ATT TAT CCT GGA AGC GGT AGT AGT TAT TAT AAT GAG AAG TTC AAG GGC AGG GTC ACA ATG ACT AGA GAC ACA
 G   L   E   W   M   G   E   I   Y   P   G   S   G   S   S   Y   Y   N   E   K   F   K   G   R   V   T   M   T   R   D   T
---------------------> <-----------------------------CDR2----------------------------> <---------------------------------

TCC ACC AGC ACA GTC TAC ATG GAA CTC AGC AGC CTG AGG TCT GAG GAC ACT GCG GTC TAT TAC TGT GCA AGA TCC GGG GAC GGC AGT CGG TTT
 S   T   S   T   V   Y   M   E   L   S   S   L   R   S   E   D   T   A   V   Y   Y   C   A   R   S   G   D   G   S   R   F
----------------------------FR3----------------------------------------------> <--------------CDR3---------

GTT TAC TGG GGC CAA GGG ACA CTA GTC ACA GTC TCC TCA GCC TCC ACC AAG GGC CCA TCG GTC TTC CCC CTG GCA CCC TCC TCC AAG AGC ACC
 V   Y   W   G   Q   G   T   L   V   T   V   S   S   A   S   T   K   G   P   S   V   F   P   L   A   P   S   S   K   S   T
------> <------------------FR4--------------------> <---------------------------Constant----------------------------

TCT GGG GGC ACA GCG GCC CTG GGC TGC CTG GTC AAG GAC TAC TTC CCC GAA CCG GTG ACG GTG TCG TGG AAC TCA GGC GCC CTG ACC AGC GGC
 S   G   G   T   A   A   L   G   C   L   V   K   D   Y   F   P   E   P   V   T   V   S   W   N   S   G   A   L   T   S   G
-----------------------------------------------------------------------------------------------------------------------

GTG CAC ACC TTC CCG GCT GTC CTA CAG TCC TCA GGA CTC TAC TCC CTC AGC AGC GTG GTG ACC GTG CCC TCC AGC AGC TTG GGC ACC CAG ACC
 V   H   T   F   P   A   V   L   Q   S   S   G   L   Y   S   L   S   S   V   V   T   V   P   S   S   S   L   G   T   Q   T
-----------------------------------------------------------------------------------------------------------------------

TAC ATC TGC AAC GTG AAT CAC AAG CCC AGC AAC ACC AAG GTG GAC AAG AAA GTT GAG CCC AAA TCT TGT GAC AAA ACT CAC ACA TGC CCA CCG
 Y   I   C   N   V   N   H   K   P   S   N   T   K   V   D   K   K   V   E   P   K   S   C   D   K   T   H   T   C   P   P
-----------------------------------------------------------------------------------------------------------------------

TGC CCA GCA CCT GAA CTC GCG GGG GCA CCG TCA GTC TTC CTC TTC CCC CCA AAA CCC AAG GAC ACC CTC ATG ATC TCC CGG ACC CCT GAG GTC
 C   P   A   P   E   L   A   G   A   P   S   V   F   L   F   P   P   K   P   K   D   T   L   M   I   S   R   T   P   E   V
-----------------------------------------------------------------------------------------------------------------------

ACA TGC GTG GTG GTG GAC GTG AGC CAC GAA GAC CCT GAG GTC AAG TTC AAC TGG TAC GTG GAC GGC GTG GAG GTG CAT AAT GCC AAG ACA AAG
 T   C   V   V   V   D   V   S   H   E   D   P   E   V   K   F   N   W   Y   V   D   G   V   E   V   H   N   A   K   T   K
-----------------------------------------------------------------------------------------------------------------------

CCG CGG GAG GAG CAG TAC AAC AGC ACG TAC CGT GTG GTC AGC GTC CTC ACC GTC CTG CAC CAG GAC TGG CTG AAT GGC AAG GAG TAC AAG TGC
 P   R   E   E   Q   Y   N   S   T   Y   R   V   V   S   V   L   T   V   L   H   Q   D   W   L   N   G   K   E   Y   K   C
-----------------------------------------------------------------------------------------------------------------------

AAG GTC TCC AAC AAA GCC CTC CCA GCC CCC ATC GAG AAA ACC ATC TCC AAA GCC AAA GGG CAG CCC CGA GAA CCA CAG GTG TAC ACC CTG CCC
 K   V   S   N   K   A   L   P   A   P   I   E   K   T   I   S   K   A   K   G   Q   P   R   E   P   Q   V   Y   T   L   P
-----------------------------------------------------------------------------------------------------------------------

CCA TCC CGG GAT GAG CTG ACC AAG AAC CAG GTC AGC CTG ACC TGC CTG GTC AAA GGC TTC TAT CCC AGC GAC ATC GCC GTG GAG TGG GAG AGC
 P   S   R   D   E   L   T   K   N   Q   V   S   L   T   C   L   V   K   G   F   Y   P   S   D   I   A   V   E   W   E   S
-----------------------------------------------------------------------------------------------------------------------

AAT GGG CAG CCG GAG AAC AAC TAC AAG ACC ACG CCT CCC GTG CTG GAC TCC GAC GGC TCC TTC TTC CTC TAC AGC AAG CTC ACC GTG GAC AAG
 N   G   Q   P   E   N   N   Y   K   T   T   P   P   V   L   D   S   D   G   S   F   F   L   Y   S   K   L   T   V   D   K
-----------------------------------------------------------------------------------------------------------------------

AGC AGG TGG CAG CAG GGG AAC GTC TTC TCA TGC TCC GTG ATG CAT GAG GCT CTG CAC AAC CAC TAC ACG CAG AAG AGC CTC TCC CTG TCT CCG
 S   R   W   Q   Q   G   N   V   F   S   C   S   V   M   H   E   A   L   H   N   H   Y   T   Q   K   S   L   S   L   S   P
-----------------------------------------------------------------------------------------------------------------------

GGT AAA TGA
 G   K   *
---------->
```

FIGURE 3E

TRX1 Heavy Chain Nucleic Acid Sequence

ATGGAATGGATCTGGATCTTTCTCCTCATCCTGTCAGGAACTCGAGGTGTCCAGTCC
CAGGTTCAGCTGGTGCAGTCTGGAGCTGAAGTGAAGAAGCCTGGGGCTTCAGTGA
AGGTGTCCTGTAAGGCTTCTGGATACACATTCACTGCCTATGTTATAAGCTGGGTGA
GGCAGGCACCTGGACAGGGCCTTGAGTGGATGGGAGAGATTTATCCTGGAAGCGG
TAGTAGTTATTATAATGAGAAGTTCAAGGGCAGGGTCACAATGACTAGAGACACATC
CACCAGCACAGTCTACATGGAACTCAGCAGCCTGAGGTCTGAGGACACTGCGGTCT
ATTACTGTGCAAGATCCGGGGACGGCAGTCGGTTTGTTTACTGGGGCCAAGGGACA
CTAGTCACAGTCTCCTCAGCCTCCACCAAGGGCCCATCGGTCTTCCCCCTGGCACC
CTCCTCCAAGAGCACCTCTGGGGGCACAGCGGCCCTGGGCTGCCTGGTCAAGGAC
TACTTCCCCGAACCGGTGACGGTGTCGTGGAACTCAGGCGCCCTGACCAGCGGCG
TGCACACCTTCCCGGCTGTCCTACAGTCCTCAGGACTCTACTCCCTCAGCAGCGTG
GTGACCGTGCCCTCCAGCAGCTTGGGCACCCAGACCTACATCTGCAACGTGAATCA
CAAGCCCAGCAACACCAAGGTGGACAAGAAAGTTGAGCCCAAATCTTGTGACAAAA
CTCACACATGCCCACCGTGCCCAGCACCTGAACTCGCGGGGGCACCGTCAGTCTT
CCTCTTCCCCCCAAAACCCAAGGACACCCTCATGATCTCCCGGACCCCTGAGGTCA
CATGCGTGGTGGTGGACGTGAGCCACGAAGACCCTGAGGTCAAGTTCAACTGGTA
CGTGGACGGCGTGGAGGTGCATAATGCCAAGACAAAGCCGCGGGAGGAGCAGTAC
AACAGCACGTACCGTGTGGTCAGCGTCCTCACCGTCCTGCACCAGGACTGGCTGA
ATGGCAAGGAGTACAAGTGCAAGGTCTCCAACAAAGCCCTCCCAGCCCCCATCGAG
AAAACCATCTCCAAAGCCAAAGGGCAGCCCCGAGAACCACAGGTGTACACCCTGCC
CCCATCCCGGGATGAGCTGACCAAGAACCAGGTCAGCCTGACCTGCCTGGTCAAA
GGCTTCTATCCCAGCGACATCGCCGTGGAGTGGGAGAGCAATGGGCAGCCGGAGA
ACAACTACAAGACCACGCCTCCCGTGCTGGACTCCGACGGCTCCTTCTTCCTCTAC
AGCAAGCTCACCGTGGACAAGAGCAGGTGGCAGCAGGGGAACGTCTTCTCATGCT
CCGTGATGCATGAGGCTCTGCACAACCACTACACGCAGAAGAGCCTCTCCCTGTCT
CCGGGTAAATGA

FIGURE 3F
TRX1 Heavy Chain Amino Acid Sequence with CDRs Highlighted

With leader sequence:

MEWIWIFLLILSGTRGVQSQVQLVQSGAEVKKPGASVKVSCKASGYTFTAYVISWVRQAPGQGLEW
MGEIYPGSGSSYYNEKFKGRVTMTRDTSTSTVYMELSSLRSEDTAVYYCARSGDGSRFVYWGQG
TLVTVSSASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELAGAPSVFLFPPKPK
DTLMISRTPEVTCVVVDVSHEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNHYTQKSLSLSPGK

Without leader sequence:

QVQLVQSGAEVKKPGASVKVSCKASGYTFTAYVISWVRQAPGQGLEWMG**EIYPGSGSSYYNEKF
KGRVTMTRDTSTSTVYMELSSLRSEDTAVYYCARSGDGSRFVY**WGQGTLVTVSSASTKGPSVFPLA
PSSKSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELAGAPSVFLFPPKPKDTLMISRTPEVTCVVVDVSHE
DPEVKFNWYVDGVEVHNAKTKPREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQPENNYKTTPPVLDSDGSFFLY
SKLTVDKSRWQQGNVFSCSVMHEALHNHYTQKSLSLSPGK

FIGURE 4A
TRX1 Light Chain

```
ATG GAG ACA GAC ACA ATC CTG CTA TGG GTG CTG CTG CTC TGG GTT CCA GGC TCC ACT GGT GAC ATT GTG ATG ACC CAA TCT CCA GAT TCT TTG
 M   E   T   D   T   I   L   L   W   V   L   L   L   W   V   P   G   S   T   G   D   I   V   M   T   Q   S   P   D   S   L
<--------------------------------Leader-------------------------------------->  <-----------------------FR1---------------

GCT GTG TCT CTA GGT GAG AGG GCC ACC ATC AAC TGC AAG GCC AGC CAA AGT GTT GAT TAT GAT GGT GAT AGT TAT ATG AAC TGG TAT CAA CAG
 A   V   S   L   G   E   R   A   T   I   N   C   K   A   S   Q   S   V   D   Y   D   G   D   S   Y   M   N   W   Y   Q   Q
------------------------------------------------------><--------------------------CDR1---------------------------> <-------------

AAA CCA GGA CAG CCA CCC AAA CTC CTC ATC TAT GTT GCA TCC AAT CTA GAG TCT GGG GTC CCA GAC AGG TTT AGT GGC AGT GGG TCT GGG ACA
 K   P   G   Q   P   P   K   L   L   I   Y   V   A   S   N   L   E   S   G   V   P   D   R   F   S   G   S   G   S   G   T
--------------------FR2-------------------->  <-----------CDR2----------> <-------------------------FR3--------------------

GAC TTC ACC CTC ACC ATC AGT TCT CTG CAG GCG GAG GAT GTT GCA GTC TAT TAC TGT CAG CAA AGT CTT CAG GAC CCT CCG ACG TTC GGT GGA
 D   F   T   L   T   I   S   S   L   Q   A   E   D   V   A   V   Y   Y   C   Q   Q   S   L   Q   D   P   P   T   F   G   G
------------------------------------------------------>  <----------------CDR3-------------> <-----------

GGT ACC AAG GTG GAA ATC AAA CGA ACT GTG GCT GCA CCA TCT GTC TTC ATC TTC CCG CCA TCT GAT GAG CAG TTG AAA TCT GGA ACT GCC TCT
 G   T   K   V   E   I   K   R   T   V   A   A   P   S   V   F   I   F   P   P   S   D   E   Q   L   K   S   G   T   A   S
------------FR4-----------> <---------------------------------------Constant----------------------------------------------

GTT GTG TGC CTG CTG AAT AAC TTC TAT CCC AGA GAG GCC AAA GTA CAG TGG AAG GTG GAT AAC GCC CTC CAA TCG GGT AAC TCC CAG GAG AGT
 V   V   C   L   L   N   N   F   Y   P   R   E   A   K   V   Q   W   K   V   D   N   A   L   Q   S   G   N   S   Q   E   S
-------------------------------------------------------------------------------------------------------------------------

GTC ACA GAG CAG GAC AGC AAG GAC AGC ACC TAC AGC CTC AGC AGC ACC CTG ACG CTG AGC AAA GCA GAC TAC GAG AAA CAC AAA GTC TAC GCC
 V   T   E   Q   D   S   K   D   S   T   Y   S   L   S   S   T   L   T   L   S   K   A   D   Y   E   K   H   K   V   Y   A
-------------------------------------------------------------------------------------------------------------------------

TGC GAA GTC ACC CAT CAG GGC CTG AGC TCG CCC GTC ACA AAG AGC TTC AAC AGG GGA GAG TGT TAG
 C   E   V   T   H   Q   G   L   S   S   P   V   T   K   S   F   N   R   G   E   C   *
----------------------------------------------------------------------------------->
```

FIGURE 4B
TRX1 Light Chain Nucleic Acid Sequence

ATGGAGACAGACACAATCCTGCTATGGGTGCTGCTGCTCTGGGTTCCAGGCTCCACTGGTGACAT
TGTGATGACCCAATCTCCAGATTCTTTGGCTGTGTCTCTAGGTGAGAGGGCCACCATCAACTGCAAG
GCCAGCCAAAGTGTTGATTATGATGGTGATAGTTATATGAACTGGTATCAACAGAAACCAGGACAG
CCACCCAAACTCCTCATCTATGTTGCATCCAATCTAGAGTCTGGGGTCCCAGACAGGTTTAGTGG
CAGTGGGTCTGGGACAGACTTCACCCTCACCATCAGTTCTCTGCAGGCGGAGGATGTTGCAGTCT
ATTACTGTCAGCAAAGTCTTCAGGACCCTCCGACGTTCGGTGGAGGTACCAAGGTGGAAATCAAA
CGAACTGTGGCTGCACCATCTGTCTTCATCTTCCCGCCATCTGATGAGCAGTTGAAATCTGGAACT
GCCTCTGTTGTGTGCCTGCTGAATAACTTCTATCCCAGAGAGGCCAAAGTACAGTGGAAGGTGGAT
AACGCCCTCCAATCGGGTAACTCCCAGGAGAGTGTCACAGAGCAGGACAGCAAGGACAGCACCTA
CAGCCTCAGCACACCCTGACGCTGAGCAAAGCAGACTACGAGAAACACAAAGTCTACGCCTGCG
AAGTCACCCATCAGGGCCTGAGCTCGCCCGTCACAAAGAGCTTCAACAGGGGAGAGTGTTAG

FIGURE 4C
TRX1 Light Chain Amino Acid Sequence with CDRs Highlighted

With leader sequence:

METDTILLWVLLLWVPGSTGDIVMTQSPDSLAVSLGERATINCKASQSVDYDGDSYMNWYQQKPG
QPPKLLIYVASNLESGVPDRFSGSGSGTDFTLTISSLQAEDVAVYYCQQSLQDPPTFGGGTKVEIKR
TVAAPSVFIFPPSDEQLKSGTASVVCLLNNFYPREAKVQWKVDNALQSGNSQESVTEQDSKDSTYSL
SSTLTLSKADYEKHKVYACEVTHQGLSSPVTKSFNRGEC

Without leader sequence:

DIVMTQSPDSLAVSLGERATINCKASQSVDYDGDSYMNWYQQKPGQPPKLLIYVASNLESGVPDR
FSGSGSGTDFTLTISSLQAEDVAVYYCQQSLQDPPTFGGGTKVEIKRTVAAPSVFIFPPSDEQLKSGT
ASVVCLLNNFYPREAKVQWKVDNALQSGNSQESVTEQDSKDSTYSLSSTLTLSKADYEKHKVYACEV
THQGLSSPVTKSFNRGEC

FIGURE 4D
TRX1 Heavy Chain
(aglycosyl)

```
ATG GAA TGG ATC TGG ATC TTT CTC CTC ATC CTG TCA GGA ACT CGA GGT GTC CAG TCC CAG GTT CAG CTG GTG CAG TCT GGA GCT GAA GTG AAG
 M   E   W   I   W   I   F   L   L   I   L   S   G   T   R   G   V   Q   S   Q   V   Q   L   V   Q   S   G   A   E   V   K
<--------------------------------Leader---------------------------------> <--------------------FR1---------------------

AAG CCT GGG GCT TCA GTG AAG GTG TCC TGT AAG GCT TCT GGA TAC ACA TTC ACT GCC TAT GTT ATA AGC TGG GTG AGG CAG GCA CCT GGA CAG
 K   P   G   A   S   V   K   V   S   C   K   A   S   G   Y   T   F   T   A   Y   V   I   S   W   V   R   Q   A   P   G   Q
-----------------------------------------------------------------------> <------CDR1--------> <-----------FR2---------------

GGC CTT GAG TGG ATG GGA GAG ATT TAT CCT GGA AGC GGT AGT AGT TAT TAT AAT GAG AAG TTC AAG GGC AGG GTC ACA ATG ACT AGA GAC ACA
 G   L   E   W   M   G   E   I   Y   P   G   S   G   S   S   Y   Y   N   E   K   F   K   G   R   V   T   M   T   R   D   T
---------------------> <-----------------------------CDR2-----------------------------------> <---------------------------

TCC ACC AGC ACA GTC TAC ATG GAA CTC AGC AGC CTG AGG TCT GAG GAC ACT GCG GTC TAT TAC TGT GCA AGA TCC GGG GAC GGC AGT CGG TTT
 S   T   S   T   V   Y   M   E   L   S   S   L   R   S   E   D   T   A   V   Y   Y   C   A   R   S   G   D   G   S   R   F
----------------------------------FR3-----------------------------------------------------> <-------------CDR3---------

GTT TAC TGG GGC CAA GGG ACA CTA GTC ACA GTC TCC TCA GCC TCC ACC AAG GGC CCA TCG GTC TTC CCC CTG GCA CCC TCC TCC AAG AGC ACC
 V   Y   W   G   Q   G   T   L   V   T   V   S   S   A   S   T   K   G   P   S   V   F   P   L   A   P   S   S   K   S   T
------> <-------------------FR4--------------------> <------------------------------Constant-----------------------------

TCT GGG GGC ACA GCG GCC CTG GGC TGC CTG GTC AAG GAC TAC TTC CCC GAA CCG GTG ACG GTG TCG TGG AAC TCA GGC GCC CTG ACC AGC GGC
 S   G   G   T   A   A   L   G   C   L   V   K   D   Y   F   P   E   P   V   T   V   S   W   N   S   G   A   L   T   S   G
-------------------------------------------------------------------------------------------------------------------------

GTG CAC ACC TTC CCG GCT GTC CTA CAG TCC TCA GGA CTC TAC TCC CTC AGC AGC GTG GTG ACC GTG CCC TCC AGC AGC TTG GGC ACC CAG ACC
 V   H   T   F   P   A   V   L   Q   S   S   G   L   Y   S   L   S   S   V   V   T   V   P   S   S   L   G   T   Q   T
-------------------------------------------------------------------------------------------------------------------------

TAC ATC TGC AAC GTG AAT CAC AAG CCC AGC AAC ACC AAG GTG GAC AAG AAA GTT GAG CCC AAA TCT TGT GAC AAA ACT CAC ACA TGC CCA CCG
 Y   I   C   N   V   N   H   K   P   S   N   T   K   V   D   K   K   V   E   P   K   S   C   D   K   T   H   T   C   P   P
-------------------------------------------------------------------------------------------------------------------------

TGC CCA GCA CCT GAA CTC CTG GGG GGA CCG TCA GTC TTC CTC TTC CCC CCA AAA CCC AAG GAC ACC CTC ATG ATC TCC CGG ACC CCT GAG GTC
 C   P   A   P   E   L   L   G   G   P   S   V   F   L   F   P   P   K   P   K   D   T   L   M   I   S   R   T   P   E   V
-------------------------------------------------------------------------------------------------------------------------

ACA TGC GTG GTG GTG GAC GTG AGC CAC GAA GAC CCT GAG GTC AAG TTC AAC TGG TAC GTG GAC GGC GTG GAG GTG CAT AAT GCC AAG ACA AAG
 T   C   V   V   V   D   V   S   H   E   D   P   E   V   K   F   N   W   Y   V   D   G   V   E   V   H   N   A   K   T   K
-------------------------------------------------------------------------------------------------------------------------

CCG CGG GAG GAG CAG TAC GCC AGC ACG TAC CGT GTG GTC AGC GTC CTC ACC GTC CTG CAC CAG GAC TGG CTG AAT GGC AAG GAG TAC AAG TGC
 P   R   E   E   Q   Y   A   S   T   Y   R   V   V   S   V   L   T   V   L   H   Q   D   W   L   N   G   K   E   Y   K   C
-------------------------------------------------------------------------------------------------------------------------

AAG GTC TCC AAC AAA GCC CTC CCA GCC CCC ATC GAG AAA ACC ATC TCC AAA GCC AAA GGG CAG CCC CGA GAA CCA CAG GTG TAC ACC CTG CCC
 K   V   S   N   K   A   L   P   A   P   I   E   K   T   I   S   K   A   K   G   Q   P   R   E   P   Q   V   Y   T   L   P
-------------------------------------------------------------------------------------------------------------------------

CCA TCC CGG GAT GAG CTG ACC AAG AAC CAG GTC AGC CTG ACC TGC CTG GTC AAA GGC TTC TAT CCC AGC GAC ATC GCC GTG GAG TGG GAG AGC
 P   S   R   D   E   L   T   K   N   Q   V   S   L   T   C   L   V   K   G   F   Y   P   S   D   I   A   V   E   W   E   S
-------------------------------------------------------------------------------------------------------------------------

AAT GGG CAG CCG GAG AAC AAC TAC AAG ACC ACG CCT CCC GTG CTG GAC TCC GAC GGC TCC TTC TTC CTC TAC AGC AAG CTC ACC GTG GAC AAG
 N   G   Q   P   E   N   N   Y   K   T   T   P   P   V   L   D   S   D   G   S   F   F   L   Y   S   K   L   T   V   D   K
-------------------------------------------------------------------------------------------------------------------------

AGC AGG TGG CAG CAG GGG AAC GTC TTC TCA TGC TCC GTG ATG CAT GAG GCT CTG CAC AAC CAC TAC ACG CAG AAG AGC CTC TCC CTG TCT CCG
 S   R   W   Q   Q   G   N   V   F   S   C   S   V   M   H   E   A   L   H   N   H   Y   T   Q   K   S   L   S   L   S   P
-------------------------------------------------------------------------------------------------------------------------

GGT AAA TGA
 G   K   *           ---------->
```

FIGURE 4E

TRX1 aglycosyl mut Heavy Chain Nucleic Acid Sequence

ATGGAATGGATCTGGATCTTTCTCCTCATCCTGTCAGGAACTCGAGGTGTCCAGTCCCAG
GTTCAGCTGGTGCAGTCTGGAGCTGAAGTGAAGAAGCCTGGGGCTTCAGTGAAGGTGTC
CTGTAAGGCTTCTGGATACACATTCACTGCCTATGTTATAAGCTGGGTGAGGCAGGCACC
TGGACAGGGCCTTGAGTGGATGGGAGAGATTTATCCTGGAAGCGGTAGTAGTTATTATAA
TGAGAAGTTCAAGGGCAGGGTCACAATGACTAGAGACACATCCACCAGCACAGTCTACAT
GGAACTCAGCAGCCTGAGGTCTGAGGACACTGCGGTCTATTACTGTGCAAGATCCGGGG
ACGGCAGTCGGTTTGTTTACTGGGGCCAAGGGACACTAGTCACAGTCTCCTCAGCCTCCA
CCAAGGGCCCATCGGTCTTCCCCCTGGCACCCTCCTCCAAGAGCACCTCTGGGGGCACA
GCGGCCCTGGGCTGCCTGGTCAAGGACTACTTCCCCGAACCGGTGACGGTGTCGTGGA
ACTCAGGCGCCCTGACCAGCGGCGTGCACACCTTCCCGGCTGTCCTACAGTCCTCAGGA
CTCTACTCCCTCAGCAGCGTGGTGACCGTGCCCTCCAGCAGCTTGGGCACCCAGACCTA
CATCTGCAACGTGAATCACAAGCCCAGCAACACCAAGGTGGACAAGAAAGTTGAGCCCA
AATCTTGTGACAAAACTCACACATGCCCACCGTGCCCAGCACCTGAACTCCTGGGGGGA
CCGTCAGTCTTCCTCTTCCCCCCAAAACCCAAGGACACCCTCATGATCTCCCGGACCCCT
GAGGTCACATGCGTGGTGGTGGACGTGAGCCACGAAGACCCTGAGGTCAAGTTCAACTG
GTACGTGGACGGCGTGGAGGTGCATAATGCCAAGACAAAGCCGCGGGAGGAGCAGTAC
GCCAGCACGTACCGTGTGGTCAGCGTCCTCACCGTCCTGCACCAGGACTGGCTGAATGG
CAAGGAGTACAAGTGCAAGGTCTCCAACAAAGCCCTCCCAGCCCCCATCGAGAAAACCA
TCTCCAAAGCCAAAGGGCAGCCCCGAGAACCACAGGTGTACACCCTGCCCCCATCCCGG
GATGAGCTGACCAAGAACCAGGTCAGCCTGACCTGCCTGGTCAAAGGCTTCTATCCCAG
CGACATCGCCGTGGAGTGGGAGAGCAATGGGCAGCCGGAGAACAACTACAAGACCACG
CCTCCCGTGCTGGACTCCGACGGCTCCTTCTTCCTCTACAGCAAGCTCACCGTGGACAA
GAGCAGGTGGCAGCAGGGGAACGTCTTCTCATGCTCCGTGATGCATGAGGCTCTGCACA
ACCACTACACGCAGAAGAGCCTCTCCCTGTCTCCGGGTAAATGA

FIGURE 4F

TRX1 Heavy Chain aglycosyl mut Amino Acid Sequence with CDRs Highlighted

With leader sequence:

MEWIWIFLLILSGTRGVQSQVQLVQSGAEVKKPGASVKVSCKASGYTFTAYVISWVRQAPGQGLE
WMGEIYPGSGSSYYNEKFKGRVTMTRDTSTSTVYMELSSLRSEDTAVYYCARSGDGSRFVYWG
QGTLVTVSSASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYASTYRVVSVL
TVLHQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHNHYT
QKSLSLSPGK

Without leader sequence:

QVQLVQSGAEVKKPGASVKVSCKASGYTFTAYVISWVRQAPGQGLEWMG**EIYPGSGSSYYNEK
FKGRVTMTRDTSTSTVYMELSSLRSEDTAVYYCARSGDGSRFVY**WGQGTLVTVSSASTKGPSVFP
LAPSSKSTSGGTAALGCLVKDYFPEPVTVSWNSGALTSGVHTFPAVLQSSGLYSLSSVVTVPSSSLG
TQTYICNVNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYASTYRVVSVLTVLHQDWLNGKEYKCKVS
NKALPAPIEKTISKAKGQPREPQVYTLPPSRDELTKNQVSLTCLVKGFYPSDIAVEWESNGQPENNY
KTTPPVLDSDGSFFLYSKLTVDKSRWQQGNVFSCSVMHEALHNHYTQKSLSLSPGK

168137 v2 - (figures)

ANTI-CD4 ANTIBODIES

This is a continuation-in-part application of U.S. application Ser. No. 10/171,452, filed Jun. 13, 2002 now abandoned, which claims priority to G.B application No. 0114517.6, filed Jun. 14, 2001; G.B. application No. 0122724.8, filed Sep. 20, 2001; U.S. provisional application No. 60/345,194, filed Oct. 19, 2001; U.S. provisional application No. 60/373,470, filed Apr. 18, 2002; and U.S. provisional application No. 60/373,471, filed Apr. 18, 2002, the contents of which are incorporated herein by reference.

The present invention is applicable to inhibiting, preventing or ameliorating an immune response against an antigen(s). Such inhibiting, preventing, or ameliorating an immune response against an antigen(s) includes inducing tolerance to the antigen(s). This invention also relates to tolerance induction and/or preventing or inhibiting T cell activation and proliferation and, more particularly, to inducing tolerance in a primate.

Tolerance to foreign antigen or tissue, or self antigen or tissue is a state whereby an otherwise normal, mature immune system is specifically unable to respond aggressively to that antigen/tissue which it therefore treats like a normal (non-diseased) body tissue/component, yet at the same time it can respond aggressively to foreign or diseased antigens/tissues to which it has not been specifically made tolerant by the natural process of self tolerance or by creating a tolerance-permissive environment in vivo.

In accordance with one aspect of the present invention there is provided a process for inducing tolerance by use of a compound, or a combination of at least two compounds, wherein the compound or combination has certain characteristics when tested in vitro, with a non-limiting example of said compound in a preferred embodiment being a CD4 antibody.

It is to be understood that the terminology a "combination of at least two compounds" does not mean that the compounds have to be administered in admixture with each other. Thus, treatment with or use of such a combination encompasses a mixture of the compounds, or separate administering of the compounds, and includes administration on the same day or different days. Thus the terminology "combination" means two or more compounds are used for the treatment, either individually or in admixture with each other. The term "compound" is used in a broad sense and encompasses materials, such as materials used in gene therapy (for example a vector that includes a polynucleotide encoding a therapeutic protein).

In accordance with another aspect of the present invention there is provided a novel CD4 antibody and uses therefor.

In accordance with a further aspect of the present invention there is provided a compound or combination of at least two compounds for inducing tolerance in a primate.

In accordance with a further aspect of the present invention there is provided a novel CD4 antibody in combination with a drug, treatment or method.

In accordance with a further aspect of the invention there is provided a process for inducing tolerance in a primate by use of a compound or a combination of at least two compounds, wherein the compound or combination has certain characteristics by use of a dosing regimen that induces such tolerance in a primate, with a non-limiting example of said compound in a preferred embodiment being a CD4 antibody.

In accordance with a further aspect of the present invention, there is provided a screen or test for identifying a compound, or compound combinations that are useful for inducing tolerance against one or more antigens.

In accordance with a further aspect of the invention is provided a novel method of treating, curing or ameliorating symptoms associated with disease or pathological states including but not limited to transplant rejection, graft-versus-host disease, autoimmune disease including but not limited to rheumatoid arthritis, diabetes and multiple sclerosis, inflammatory diseases and conditions associated with an inflamatory process, allergy, anaphylaxis and those conditions associated with anaphylaxis, asthma, cancer, and infections including but not limited to viral infections.

In accordance with a further aspect of the invention is provided a novel method of inducing tolerance to therapeutic agents such as proteins, peptides, cells, gene therapy agents, etc.

BRIEF DESCRIPTION OF THE DRAWINGS

FIG. 1 shows the amino acid sequences of the heavy and light chains of the first embodiment of TRX1 antibody, as well as the CDR and framework regions of the heavy and light chains.

FIG. 2 shows the amino acid sequences of the heavy and light chains of another embodiment of the TRX1 antibody, as well as the CDR and framework regions of the heavy and light chains.

FIG. 3 shows the amino acid sequences of the heavy and light chains of another embodiment of the TRX1 antibody, as well as the CDR and framework regions of the heavy and light chains.

FIG. 4 shows the amino acid sequences of the heavy and light chains of another embodiment of the TRX1 antibody, as well as the CDR and framework regions of the heavy and light chains.

DETAILED DESCRIPTION OF THE INVENTION

Figure 5:
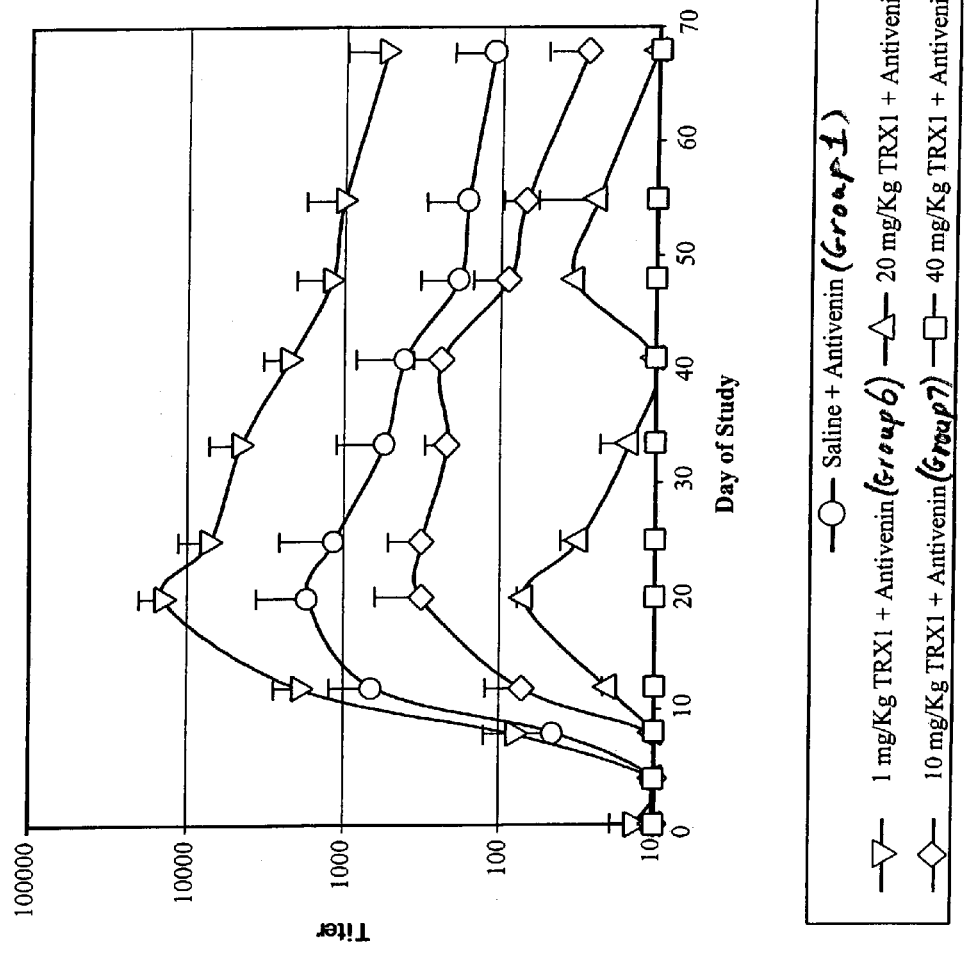
FIG. 5 shows the immune response to antivenin for the first 68 days (i.e., the tolerization phase) of a study of groups of baboons which were given antivenin alone or in combination with TRX1 antibody.

In accordance with one aspect of the present invention, there is provided a process for tolerizing a primate against an antigen(s) by use of a compound or a combination of at least two compounds, as hereinafter described. The compound, or combination is administered in an amount and in accordance with a dosage regimen that is effective for inducing tolerance in a primate. The compound, or a combination of at least two compounds is a compound, or combination that when present in a primary mixed lymphocyte reaction (MLR) as compared to a mixed lymphocyte reaction in the absence of the compound, or said combination reduces the amount of cells that are positive for both CD4 and CD25 (CD4+CD25+ cells) that result from the mixed lymphocyte reaction. In a preferred embodiment, the compound, or said combination is a compound, or said combination that reduces the amount of such CD4+CD25+ cells by at least 40% and preferably by at least 60% and still more preferably by at least 70%.

In a preferred embodiment, such a compound, or said combination produces a cell population that inhibits a primary mixed lymphocyte reaction (performed with cells that have not been previously exposed to the compound, or said compound in combination with a drug, treatment or method,) by reducing the CD4+CD25+ cells produced in the primary MLR. In a preferred embodiment, there is at least a 10% reduction and preferably at least a 20% reduction. Protocols for performing the hereinabove described mixed lymphocyte reactions are described in Example 5.

In addition, in a preferred embodiment, the compound, or said combination is a compound, or said combination that reduces the amount of CD4+CD25+ cells produced in a primary mixed lymphocyte reaction and generates a cell population in such primary mixed lymphocyte reaction which cell population inhibits a secondary mixed lymphocyte reaction. In a preferred embodiment, the cells are generated in a primary mixed lymphocyte reaction that is performed in the presence of the compound, or said combination, which cells when added to the secondary mixed lymphocyte reaction preferably reduce the CD4+CD25+ cells generated in such secondary mixed lymphocyte reaction, as compared to a secondary mixed lymphocyte reaction in the absence of the added cells by at least 20% more preferably by at least 35%, and more preferably by at least 50%.

An inhibition of either a primary or secondary MLR by such a cell population is evidenced by a reduction in the amount of CD4+CD25+ cells produced in the MLR as compared to the MLR performed in the absence of such a cell population.

Thus, in accordance with an aspect of the present invention, a primate is treated with a compound, or a combination of at least two compounds having the characteristics as hereinabove described (reduction of the amount of CD4+CD25+ cells produced in an in vitro primary MLR, with such primary MLR generating a cell population that reduces the amount of CD4+CD25+ cells produced in vitro in a primary and/or secondary MLR and that preferably effects such reduction in both a primary and secondary MLR).

In one embodiment, the cells generated in the primary MLR in the presence of the compound, or said combination, are cells which when added to a secondary MLR (as compared to a secondary MLR without the added cells) reduces and/or eliminates the generation of one or more of cytokines; in particular, one or more of IL-2, IL-4 and IL-12 in the secondary MLR. In general, such reduction of at least one of IL-2, IL-4 and IL-12 is at least 40%, preferably by at least 60%.

Thus, a preferred compound, or preferred combination is one that generates cells in a primary MLR that in a secondary MLR, as compared to control, reduces production of CD4+CD25+ cells or one or more or all (preferably all) of IL-2, IL-4 and IL-12 and preferably reduces production of both such cells and such cytokines.

In accordance with an additional aspect, there is provided a screen or test in which, in vitro, T cells are exposed to a material(s) or compound(s) under conditions which stimulate and cause the T cells to proliferate, with such exposure being effected in the presence of a compound, or a combination of at least two compounds that is to be tested for its ability to induce tolerance. The T cell proliferation test may be a mixed lymphocyte reaction or a test in which T cells are caused to proliferate by a non-antigen specific stimulation through the T cell receptor (TCR) or a component of the TCR complex, for example a CD3 component. Typically, an anti-CD3 monoclonal antibody is used to stimulate T cells and cause them to proliferate. In addition to stimulation through the TCR complex, co-stimulatory signals sometimes are provided by addition of antibodies which bind co-stimulatory molecules such as CD28. The T cells that have been caused to proliferate, in the presence and absence of the compound, or said compound in combination with a drug, treatment or method, that is being tested, are examined to determine a subset of T cells that are CD4 positive (CD4+) and CD25 positive (CD25+) in order to determine whether the presence of the compound, or said combination inhibited the production of such T cell subset.

The in vitro test that is used to test a compound, or said combination for tolerance-inducing activity is preferably a mixed lymphocyte reaction (MLR). Mixed lymphocyte reactions are generally known in the art, and a protocol therefor is described in Example 5, however, the scope of the invention is not to be limited thereby.

The cell population produced in the initial test may then be tested in at least one further test in which T cells, in vitro are caused to proliferate in order to determine whether such cell population inhibits production of CD4+CD25+ cells.

The at least one further test may be a mixed lymphocyte reaction (a primary or secondary mixed lymphocyte reaction) or a test in which T cells are caused to proliferate in response to a non-antigen specific stimulation through the T cell receptor (TCR) or a component of the TCR complex or with co-stimulation which mimics an antigen specific stimulation through TCR.

A protocol for such a test is described in Example 5; however, the scope of the invention is not to be limited thereby.

In a preferred embodiment, the screen or test for determining a compound or a combination of at least two different compounds to be used for inducing tolerance involves both the initial test to determine whether the compound, or said combination in an in vitro T cell proliferation test, such as an MLR, reduces the production of CD4+CD25+ cells and a subsequent test to determine whether cells produced in the first test inhibit the production of CD4+CD25+ cells in a second T cell proliferation test, such as a primary and/or secondary MLR and, in particular, a secondary MLR and/or cytokine production in a secondary MLR.

In accordance with a preferred embodiment, a compound, or said combination selected for inducing tolerance is one that causes reduction of production of CD4+CD25+ cells in the initial test and produces a cell population therein that reduces production of such T cell subset in a second test, as hereinabove described and/or that reduces cytokine production and, in particular, one or more of IL-2, IL-4 and IL-12 in a second test.

Thus, in accordance with an aspect of the invention, the selected compound or combination of at least two compounds is a compound, or combination that when present in a T cell proliferation assay such as a primary mixed lymphocyte reaction (MLR) as compared to a mixed lymphocyte reaction in the absence of the compound, or said combination reduces the amount of cells that are positive for both CD4 and CD25 (CD4+CD25+ cells) that result from the mixed lymphocyte reaction. In a preferred embodiment, the compound, or said combination is a compound, or said combination that reduces the amount of such CD4+CD25+ cells by at least 40% and preferably by at least 60% and still more preferably by at least 70%.

In addition, in a preferred embodiment, the selected compound or combination is one that reduces the amount of CD4+CD25+ cells produced in a primary mixed lymphocyte reaction and generates a cell population in such primary mixed lymphocyte reaction which cell population inhibits a secondary mixed lymphocyte reaction. In a preferred embodiment, the cells are generated in a primary mixed lymphocyte reaction that is performed in the presence of the compound, or said combination which cells when added to the secondary mixed lymphocyte reaction preferably reduce the CD4+CD25+ cells generated in such secondary mixed lymphocyte reaction, (as compared to a secondary mixed lymphocyte reaction in the absence of the added cells) by at least 20% more preferably by at least 35% and more preferably by at least 50%. In a preferred embodiment, such cells in the secondary MLR, as compared to a control, reduce the production of at least one of IL-2, IL-4 and IL-12 by at least 40% and preferably by at least 60%.

An inhibition of either a primary or secondary MLR by such a cell population is evidenced by a reduction in the amount of CD4+CD25+ cells produced in the MLR as compared to the MLR performed in the absence of such a cell population, and with respect to the secondary MLR, may be evidenced by reduction of CD4+CD25+ cells or reduced cytokine production and preferably by both.

In one embodiment, the compound that is used to induce tolerance in a primate is an antibody (or fragment thereof) or a combination of an antibody (or fragment thereof) with another antibody or a compound other than an antibody, however, the present invention is not limited to such antibody use.

Thus, the present invention with respect to one aspect for inducing tolerance in a primate contemplates the use of a compound that is capable of inducing tolerance in a primate that has characteristics as hereinabove described, which compound may be used alone or in combination with one or more other compounds, which one or more other compounds may or may not have the characteristics as hereinabove described. In addition, the present invention contemplates the use of a combination of at least two compounds wherein one or more of the compounds have characteristics as hereinabove described or wherein none of the compounds of such combination individually have characteristics as hereinabove described but wherein when combined, the combination has such characteristics. Thus, a combination of at least two compounds may have characteristics as hereinabove described as a result of one or more of the compounds thereof having such characteristics or as a result of the combination of two or more of the compounds of the combination imparting such characteristics.

In some cases, a compound of the present invention is employed in combination with a compound(s) that is an immunosuppressant. The compound(s) that is an immunosuppressant may be employed in dosages less than that required to effect a generalized immunosuppression or may be used in dosages that effect a general immunosuppression. The combination and relative amounts of the compounds of the combination that is used is effective for inducing tolerance in a primate.

Some examples of compounds used in combination with a compound having the hereinabove described characteristics to induce tolerance in a primate include but are not limited to Rituxan™ (Genentech); an antibody which binds specifically to B cells; an antibody specific for plasma cells, including but not limited to ID4 (Research Diagnostics); CellCept™ (Roche); cyclosporin; rapamycin; anti-CD40L; anti-IL12; anti-IL18; anti-interferon-gamma; proteosome inhibitor(s); an antagonist of CXCR3; 15-deoxyspergualin; FK506; monoclonal antibodies directed against co-stimulatory molecules such as CD2, CD8 and CD28, as well as monoclonal antibodies directed against adhesion molecules.

Additional non-limiting examples of compounds that may be used in combinations include gene therapy materials for expressing a protein, in vivo, peptidomimetics, ribozymes, antisense oligonucleotides, nucleid acid aptamers, peptides, small organic molecules and antibodies, As used herein, the term "tolerize" or "tolerant" with respect to an antigen means that, without requiring total, general immunosuppression, the primate does not produce an adverse immune response to the antigen over a period of time after treatment is stopped even when subsequently challenged with the antigen and/or when the antigen remains present in the primate, but is capable of providing an immune response against other antigens The tolerized or tolerant state may be induced in a primate by administering an effective dose of a compound of the present invention or a combination of at least two compounds as described herein. As hereinabove described when using a combination of compounds, they may be administered concurrently or sequentially.

The antigen(s) as to which tolerance is induced may be a self antigen or a foreign antigen.

The foreign antigen may be one or more of the following types of antigens:

(i) a foreign antigen present on transplanted tissue or cells, including tissue or cells present in an organ wherein the transplant may be allogeneic or xenogeneic;

(ii) a therapeutic agent (which also includes therapeutic agents used for disease prevention) that produces an immune response in a primate, which immune response diminishes the ability of the agent to function as a therapeutic agent. Such agents include, but are not limited to, delivery vehicles, such as vectors used in gene therapy; active agents such as proteins delivered to the primate, such as recombinant proteins such as monoclonal antibodies, enzymes, clotting factors and some small molecule drugs, or proteins produced from an agent delivered to the primate, such as in gene therapy.

The foreign antigens against which tolerance is induced in accordance with the present invention are not foreign antigens as present in disease-causing bacteria, fungi, viruses, etc. that infect a host, i.e., the term foreign antigen does not include a foreign antigen as part of an organism that infects a primate and causes a disease or disorder.

In accordance with one aspect, a primate is treated to produce tolerance against an antigen(s) by treating the primate with at least one CD4 antibody or fragment thereof or at least one CD4 antibody or fragment thereof in combination with another compound(s) (a compound other than a CD4 antibody or a different CD4 antibody) in an amount and for a time that is effective for providing such tolerance, with the antibody being present in the primate at a time when such antigen is also present in the primate, with such treatment resulting in the primate being tolerant to the antigen. Such CD4 antibody or fragment thereof or at least one CD4 antibody or fragment thereof in combination with another compound has the hereinabove described characteristics when tested in vitro in an MLR (reduces the amount of CD4+ CD25+ cells produced in a primary MLR, with the cell population produced in the primary MLR when tested in vitro in at least one of a primary or a secondary MLR reduces the amount of CD4+CD25+ cells produced therein).

The CD4 antibody is preferably a monoclonal antibody (or fragment thereof that retains the ability to bind to CD4). The antibody may be a human antibody or a non-human antibody, with non-human antibodies including humanized antibodies, chimeric antibodies, murine antibodies, etc.

The CD4 antibody or fragment thereof or at least one CD4 antibody or fragment thereof in combination with another compound is administered to a primate in an amount and for a time effective to induce tolerance against a foreign or self-antigen and preferably a foreign antigen.

In accordance with a preferred embodiment, the CD4 antibody or fragment thereof is administered over a period of time in order to maintain in the primate appropriate levels of such antibody or fragment or if said antibody or fragment is used in combination with another compound as described herein at an effective dose of said combination over a period of time that is sufficient to induce tolerance.

In general, the antibody (or fragment thereof) is administered in an initial dose of at least about 40 mg, preferably at least about 50 mg and more preferably in an amount of at least about 70 mg alone or in combination with another compound(s) as described herein.

In one preferred embodiment, the initial dose is at least 400 mg, preferably at least about 500 mg and in a particular embodiment in an amount of at least about 700 mg. alone or in combination with another compound(s) as described herein.

The initial dose may be administered in one or more doses over a twenty-four hour period and preferably in one dose over twenty-four hours, alone or in combination with another compound(s) as described herein.

As used herein in reference to a dosage amount a dose is the total amount of antibody administered over a twenty-four hour period, even if administered more than once in 24 hours, alone or in combination with another compound(s) as described herein.

In most cases, after the initial dose, the CD4 antibody (or appropriate fragment thereof) is administered in one or more follow-up doses over several day(s), with each follow-up dose being administered in one or more doses in a twenty-four hour period, alone or in combination with another compound(s) as described herein. The follow-up dose(s) is generally provided in an amount to return serum levels of the antibody to those that were achieved by the initial dose, given alone or in combination with another compound(s) as described herein.

In a preferred embodiment, the minimum follow-up dose or doses is in an amount that is at least equal to the amounts hereinabove described and may or may not be identical to the dose given as the original or initial dose alone or in combination with another compound(s) as described herein. Thus, a follow-up dose is generally at least 40 mg, preferably at least 50 mg, and more preferably at least 70 mg alone or in combination with another compound(s) as described herein. As hereinabove described, in one preferred embodiment, the follow-up dose(s) is at least 400 mg, preferably at least 500 mg, and in a particular embodiment at least 700 mg. alone or in combination with another compound(s) as described herein. In some cases, the follow-up dose or doses may be less than the minimum amount alone or in combination with a another compound(s) as described herein.

If there is more than one follow-up dose, each such additional follow-up dose over a 24-hour period may be the same or different than another follow-up dose alone or in combination with another compound(s) as described herein.

The number of follow-up doses will vary, but in a preferred embodiment, there is generally at least one follow-up dose and in most cases there is no more than seven follow-up doses, i.e., the total number of doses generally does not exceed eight doses alone or in combination with another compound(s) as described herein.

The total period over which the antibody is administered generally does not exceed four weeks and more preferably does not exceed three weeks alone or in combination with another compound(s) as described herein. In many cases, tolerance can be achieved by using an initial dose and one or more follow-up doses over a period that does not exceed two weeks alone or in combination with another compound(s) as described herein.

Although, in accordance with the present invention, initial tolerance to an antigen(s) can be achieved in a primate in a period of no more than four weeks, in some cases, periodic follow-up treatments with the antibody alone or in combination with another compound(s) as described herein may be required in order to maintain tolerance.

As hereinabove described, at least one CD4 antibody (or appropriate fragment thereof) is delivered in an amount that is at least sufficient to induce tolerance in a primate against an antigen(s) and in a preferred embodiment against a foreign antigen alone or in combination with another compound(s) as described herein. The maximum amount is of course limited by safety considerations. In general, the daily dosage of antibody would be less than 6000 mg alone or in combination with another compound(s) as described herein.

The number of follow-up doses and the spacing thereof will be determined, in part, by the half-life of the at least one CD4 antibody. Although the present invention is not to be limited thereby, it is believed that the CD4 antibody should be initially delivered in an amount to achieve antibody serum levels that exceed the amount required to saturate all of the CD4 of the primate being treated, with follow-up doses being given at times to maintain such excess over a period that induces tolerance in the primate against the antigen(s) alone or in combination with another compound(s) as described herein.

In a preferred embodiment, the CD4 antibody is a CD4 antibody that would have a reduced effector (i.e. lytic) function as compared to human IgG1. As representative examples of antibodies that would have reduced effector function, there may be mentioned antibodies that have an Fc portion that is aglycosylated and/or that has reduced binding to the Fc receptor and/or is non-lytic.

In one embodiment, a CD4 antibody with a reduced effector function is a non-depleting CD4 antibody. As used herein, "a non-depleting CD4 antibody" is a CD4 antibody that depletes less than 50% of CD4 cells and preferably less than 10% of CD4 cells.

In treating a primate and in particular a human, the CD4 antibody may be employed in combination with a pharmaceutically acceptable carrier alone or in combination with another compound(s) as described herein. A composition that contains a CD4 antibody may include other ingredients, for example, stabilizers and/or other active agents alone or in combination with another compound(s) as described herein.

The use of a CD4 antibody alone or in combination with another compound(s) as described herein to induce tolerance against an antigen(s) in a primate in accordance with the present invention provides tolerance against one or more antigens and the primate is capable of immunologically responding to other antigens. Thus, in this respect, the primate is made tolerant to one or more antigens, and the immune system is capable of providing an immune response against other foreign antigens whereby the primate is not immunocompromised.

In the preferred embodiment where tolerance is induced against an antigen, the CD4 antibody is administered to the primate prior to, in conjunction with or subsequent to the antigen being delivered to the primate alone or in combination with another compound(s) as described herein. In a preferred embodiment, the primate is provided with the CD4 antibody alone or in combination with another compound(s) as described herein at a time such that the antibody is present in the primate. In a particularly preferred embodiment, the CD4 antibody (or fragment thereof) alone or in combination with another compound(s) as described herein is delivered to the primate prior to the primate coming into contact with the antigen to which the primate is to be tolerized or within a few hours or less than one day thereafter. In a preferred embodiment, the antibody alone or in combination with another compound(s) as described herein is administered to the primate no more than about two, preferably no more than one day prior to the primate receiving the antigen.

As hereinabove indicated, in one embodiment, a primate is tolerized against a therapeutic protein that is to be used in treating the primate. Such therapeutic protein may be a therapeutic antibody (other than the CD4 antibody), which therapeutic antibody may be a human antibody, humanized antibody, chimeric antibody or a non-human antibody; an enzyme such as one used for replacement therapy; a hormone; clotting factor; a protein produced in gene therapy; a gene therapy delivery vehicle such as a vector used in gene therapy (for example, an adenovirus vector) alone or in combination with another compound(s) as described herein.

The present invention also contemplates kits or packages that contain the therapeutic protein against which tolerance is to be induced as well as a compound or a combination of two or more compounds as described herein with such compound or combination being used to induce tolerance against the therapeutic protein.

The foreign antigen(s) may be present in a transplanted organ, or in transplanted cells used in cell therapy, or in other tissue transplants, such as skin.

The treatment of a primate, in particular, a human, in order to tolerize the primate against a foreign antigen(s) by use of a CD4 may be accomplished in some cases without adjunct therapy, such as a bone marrow transplant to promote acceptance of a foreign antigen and/or T-cell depletion and/or immunosuppression.

In one non-limiting embodiment, the antibody is preferably a TRX1 antibody (as hereinafter described) or one that binds to the same epitope as TRX1, as hereinafter described, and such antibody is preferably used with the dosing regimen as hereinabove described alone or in combination with a drug, treatment or method as described herein.

In accordance with an aspect of the present invention, there is provided a molecule (preferably a humanized antibody or fragment thereof) which binds to the same epitope (or a portion thereof) on human lymphocytes as the humanized antibody selected from the group consisting of the humanized antibody shown in FIG. 1 and the humanized antibody shown in FIG. 2 and the humanized antibody of FIG. 3 and the humanized antibody shown in FIG. 4.

The antibody is hereinafter sometimes referred to as TRX1. The term "molecule" or "antibody that binds the same epitope as TRX1" includes TRX1. The term TRX1 " " includes the antibody shown in FIG. 1, the antibody shown in FIG. 2 and the one of FIG. 3, and the one of FIG. 4, and those identical thereto which may be produced, for example, by recombinant technology.

Although the preferred antibody is TRX1, from the teachings herein, one skilled in the art can produce antibodies that are equivalent to TRX1. As representative but non-limiting examples of such equivalent TRX1 antibodies there may be mentioned:

1) humanized antibodies that bind to the same epitope as TRX1;

2) humanized antibodies that have the same CDRs as TRX1 but which have a different humanized framework and/or a different human constant region;

3) humanized antibodies that bind to the same epitope as TRX1 in which one or more amino acids of one or more of the CDRs of TRX1 have been changed (preferably but not necessarily a conservative amino acid substitution) and in which the framework may be the same framework as TRX1 or have a different humanized framework or in which one or more of the amino acids of the framework region of TRX1 have been changed and/or in which the constant region may be the same as or different from TRX1;

4) humanized antibodies that bind to the same epitope as TRX1 wherein the antibody does not bind to the Fc region of the receptor.

5) humanized antibodies that bind to the same epitope as TRX1 wherein the CDRs thereof do not include a glycosylation site;

6) humanized antibodies that bind to the same epitope as TRX1 and that do not bind to the Fc region of the receptor and the CDRs do not include a glycosylation site;

7) a chimeric antibody that binds to the same epitope as TRX1; and 8) a murine antibody that binds to the same epitope as TRX1.

The antibodies that are equivalent to TRX1 may be used in the same manner and for the same purposes as TRX1.

The molecules or antibodies of the present invention may be used in a method for treating an animal, in particular a human, especially for use in inhibiting, ameliorating, or reducing an immune response to an antigen, which may be a foreign antigen or a self antigen, including inducing tolerance to an antigen. The molecules or antibodies may be used to inhibit, ameliorate, or reduce an immune response to a Class I presented antigen and/or to a Class II presented antigen. The molecules or antibodies may be used to inhibit, ameliorate, or reduce an immune response to such antigens. In the case of a transplant, for example, Class I and Class II major histocompatibility (MHC) antigens and non-MHC or minor histocompatibility antigens may be presented. Apart from transplantation antigens, the molecules or antibodies may be used to inhibit, ameliorate, or reduce an immune response to globular proteins, glycoproteins such as immunoglobulins, materials carried on particles such as pollen proteins, polypeptides intended for therapeutic use such as interferon, Interleukin-2 or tumor necrosis factor, or hormone replacements such as lutenizing hormone, its analogues and antagonists. Further specific antigens to which an immune response can be inhibited, ameliorated, or reduced include synthetic peptide analogues of protein therapeutic agents which are used to aid in receptor blocking, and alloantigens. Alloantigens may be responsible for rejection of foreign tissue in tissue transplants or skin grafts. The term "antigen" as used herein is a substance or material that induces an immune response in an animal, preferably a primate, more preferable a human. The immune response may be a T-cell response which may or may not be accompanied by a humoral response.

The molecules or antibodies of the present invention inhibit and/or alter T-cell activation and proliferation and Applicant has found that such inhibition can be effected when adding the molecule or antibody either before or after an agent which stimulates T-cell activation alone or in combination with a drug, treatment or method as described herein.

The molecules or antibodies of the present invention have the characteristics of binding to an epitope of a CD4 antigen (CD4 positive human T-cells), but it is to be understood, however, that although the antibody is believed to function by binding to a CD4 antigen on T-cells, the antibody may function by binding to a CD4 antigen on other cells; e.g., monocytes. As a result, the ability of such molecules or antibodies to inhibit and/or alter T-cell activation or proliferation may or may not be effected through binding to CD4 positive cells.

In accordance with another aspect of the present invention, there is provided a method of preventing and/or inhibiting an on-going immune response in human patients through the administration to the patient of an antibody, hereafter referred to as TRX1 (or fragment or derivative thereof) or any molecule that mimics such antibody or derivative or fragment thereof, i.e., binds to the same epitope as TRX1.

The term "inhibit" as used herein throughout this application is intended to mean prevention, or inhibition, or reduction in severity, or amelioration of an immune response to one or more antigens. The antigen may be a foreign antigen or a self antigen. The term "graft" as used herein for purposes of this application shall mean any and all transplantation, including but not limited to, allograft and xenograft transplantation. Such transplantation may by way of example include, but not be limited to, transplantation of cells, bone marrow, tissue, solid-organ, bone, etc.

The term "immune response(s)" as used herein is intended to mean immune responses dependent upon T cell activation and proliferation which includes both cellular effects and T cell dependent antibodies which may be elicited in response to, by way of example and not limitation: (i) grafts, (ii) graft versus host disease, and (iii) autoantigens resulting in autoimmune diseases, which by way of example include but are not limited to rheumatoid arthritis, systemic lupus, multiple sclerosis, diabetes mellitus, etc.

The compound employed in the present invention is one which binds to the same epitope (or a part of that epitope) as the TRX1 humanized antibody. The term "binds to the same epitope as TRX1 humanized antibody" is intended to describe not only the TRX1 humanized antibody but also describes other antibodies, fragments or derivatives thereof or molecules which bind to the same such epitope as the TRX1 humanized antibody.

Such molecules are preferably antibodies, but may include nucleic acid aptamers. In a preferred embodiment, the antibody does not bind to Fc receptors through the Fc region of the antibody and the CDRs do not include a glycosylation site.

The constant region may or may not include a glycosylation site. In one embodiment, the constant region includes a glycosylation site. An example of a heavy chain sequence which includes a glycosylation site is shown in FIGS. 1D and 1F and FIGS. 3D and 3F. In another embodiment, the constant region does not include a glycosylation site. An example of a heavy chain sequence which does not include a glycosylation site is shown in FIGS. 2D and 2F and in FIGS. 4D and 4F.

Such other antibodies include, by way of example and not by limitation, rat, murine, porcine, bovine, human, chimeric, humanized antibodies, or fragments or derivatives thereof.

The term "fragment" as used herein means a portion of an antibody, by way of example such portions of antibodies shall include but not be limited to CDR, Fab, or such other portions, which bind to the same epitope or any portion thereof as recognized by TRX1.

The term "antibody" as used herein includes polyclonal and monoclonal antibodies as well as antibody fragments and derivatives, as well as antibodies prepared by recombinant techniques, such as chimeric or humanized antibodies, single chain or bispecific antibodies which bind to the same epitope or a portion thereof as recognized by the humanized antibody TRX1. The term "molecules" includes by way of example and not limitation, peptides, oligonucleotides or other such compounds derived from any source which mimic the antibody or binds to the same epitope or a portion thereof as the antibody fragment or derivative thereof.

Another embodiment of the present invention provides for a method of treating a patient who is to receive or has received a graft transplant with an effective amount of at least one member selected from the group consisting of TRX1 antibody, or an antibody, or derivative or fragment thereof or molecules which bind to the same epitope (or a portion thereof) as the TRX1 antibody alone or in combination with another compound(s) as described herein. The treatment is preferably effected with the whole or intact TRX1 antibody alone or in combination with another compound(s) as described herein.

In one embodiment, the antibody is TRX1 which is a humanized antibody that includes modified constant regions of a human antibody, and light and heavy chain framework and CDR regions, in which the framework regions of the light and heavy chain variable regions correspond to the framework regions of the light and heavy chain variable region of a human antibody, and the CDRs derived from a mouse monoclonal antibody designated NSM4.7.2.4. The TRX1 antibody is shown in FIG. 1. FIG. 1A shows the amino acid (SEQ ID NO: 38) and DNA (SEQ ID NO: 37) sequences for the TRX1 light chain. FIG. 1B shows the TRX1 light chain nucleic acid sequence (SEQ ID NO: 37). FIG. 1C shows the TRX1 light chain amino acid sequence (SEQ ID NO: 38) and (SEQ ID NO: 39) with the CDRs highlighted. FIG. 1D shows the amino acid (SEQ ID NO: 41) and DNA (SEQ ID NO: 40) sequences for the TRX1 heavy chain which includes a glycosylation site. FIG. 1E shows the TRX1 heavy chain nucleotide sequence (SEQ ID NO: 40). FIG. 1F shows the TRX1 heavy chain amino acid sequences (SEQ ID NO: 41) and (SEQ ID NO: 42), which include a glycosylation site, with the CDRs highlighted.

In another embodiment, the antibody is TRX1 which is a humanized antibody that includes modified constant regions of a human antibody, and light and heavy chain framework and CDR regions, in which the framework regions of the light and heavy chain variable regions correspond to the framework regions of the light and heavy chain variable region of a human antibody, and the CDRs derived from a mouse monoclonal antibody designated NSM4.7.2.4. The TRX1 antibody is shown in FIG. 3. FIG. 3A shows the amino acid (SEQ ID NO:50) and DNA (SEQ ID NO:49) sequences for the TRX1 light chain. FIG. 3B shows the TRX1 light chain nucleic acid sequence (SEQ ID NO:49). FIG. 3C shows the TRX1 light chain amino acid sequence (SEQ ID NO:50) and (SEQ ID NO:51) with the CDRs highlighted. FIG. 3D shows the amino acid (SEQ ID NO:53) and DNA sequences (SEQ ID NO:52) for the TRX1 heavy chain which includes a glycosylation site. FIG. 3E shows the TRX1 heavy chain nucleotide sequence (SEQ ID NO:52). FIG. 3F shows the TRX1 heavy chain amino acid sequences (SEQ ID NO:53) and (SEQ ID NO:54), which include a glycosylation site, with the CDRs highlighted.

Another embodiment of the TRX1 antibody is shown in FIG. 2. FIG. 2A shows the amino acid (SEQ ID NO:44) and DNA sequences (SEQ ID NO:43) for the light chain. FIG. 2B shows the light chain nucleic acid sequence (SEQ ID NO:43). FIG. 2C shows the light chain amino acid sequence (SEQ ID NO:44) and (SEQ ID NO:45) with the CDRs highlighted. FIG. 2D shows the amino acid (SEQ ID NO:47) and DNA sequences (SEQ ID NO:46) for the heavy chain. FIG. 2E shows the heavy chain nucleotide sequence (SEQ ID NO:46). FIG. 2F shows the heavy chain amino acid sequences (SEQ ID NO:47) and (SEQ ID NO:48) with the CDRs highlighted.

Another embodiment of the TRX1 antibody is shown in FIG. 4. FIG. 4A shows the DNA (SEQ ID NO:55) and amino acid (SEQ ID NO:56) sequences for the light chain. FIG. 4B shows the light chain nucleic acid sequence (SEQ ID NO:55). FIG. 4C shows the light chain amino acid sequence (SEQ ID NO:56) and (SEQ ID NO:57) with the CDRs highlighted. FIG. 4D shows the amino acid (SEQ ID NO:59) and DNA sequences (SEQ ID NO:58) for the heavy chain. FIG. 4E shows the heavy chain nucleotide sequence (SEQ ID NO:58). FIG. 4F shows the heavy chain amino acid sequences (SEQ ID NO:59) and (SEQ ID NO:60) with the CDRs highlighted.

In the figures, amino acid residue 1 is the first amino acid, in each of the heavy and light chains, after the leader sequence. It also is the first residue in FR1 in the sequences.

The preparation of TRX1 humanized antibody suitable for the purposes of the present invention should be apparent to those skilled in the art from the teachings herein. Such antibody may be prepared by recombinant techniques known to those skilled in the art.

The antibodies of the present invention may be used to inhibit an immune response in an animal by administering the antibody (or fragment thereof) in an amount effective to inhibit such immune response alone or in combination with another compound(s) as described herein.

For example, in some cases, treatment with a therapeutic agent includes an immune response against the therapeutic agent. As representative examples of such therapeutic agents there may be mentioned monoclonal antibodies such as ReoPro and OKT3, enzymes for replacement therapy such as, but not limited to, glucocerebrosidase for Gaucher's disease and clotting factors such as Factor VIII, and products of gene therapy and gene therapy delivery vehicles such as adenovirus derived vectors.

In accordance with an aspect of the present invention, an antibody as hereinabove described (or fragment of such antibody) is administered to a patient that is to be treated with such therapeutic agent, with the antibody (or fragment) being administered in an amount effective to inhibit the immune response against the therapeutic agent. The antibody may be administered prior to, in combination with, or subsequent to administration of the therapeutic agent. The method of administration is dependent on a variety of factors, including, but not limited to, the specific indication, specific therapeutic agent and optimal dosing schedule If administered prior to the administration of the therapeutic agent, the antibody is administered from about 1 hour to about 10 days prior to the administration of the therapeutic agent, preferably from about 1 hour to about 24 hours prior to the administration of the therapeutic agent. If administered after the administration of the therapeutic agent, the antibody is administered from about 1 hour to about 10 days after the administration of the therapeutic agent, preferably from about 1 hour to about 24 hours after the administration of the therapeutic agent.

The amount of antibody administered, the dosing schedule and the number of times that the antibody is administered is dependent upon the therapeutic agent and the regimen used for treating a patient with the therapeutic agent.

In general, the antibody may be used in an amount from 0.1 milligram to 3 grams per dose provided, however, that in inducing tolerance in a primate, the antibody is preferably used in amounts as hereinabove described.

The antibody of the present invention may also be used to inhibit an immune response against a self-antigen and/or a foreign antibody, e.g., against a transplant (for example, transplant rejection) and/or to inhibit or ameliorate an immune response of a graft against a host.

The antibody of the present invention may also be used to inhibit an immune response against gene therapy products as well as an immune response against gene therapy delivery vehicles such as adenovirus derived vectors which limit the effectiveness of the gene therapy.

Thus, an immune response to an antigen in a host can be inhibited, ameliorated, or reduced by administering TRX1 antibody along with the antigen. A patient may be given a tissue transplant such as an organ transplant or a bone marrow transplant and may be given TRX1 antibody along with the transplant to inhibit rejection thereof. Also, tolerance may be induced to an antigen already possessed by a patient. Long-term specific tolerance can be induced to a self-antigen or antigens in order to treat autoimmune diseases.

Persistent or periodic antigen presence is required to maintain tolerance. A tissue graft, for example, supplies the antigen to maintain tolerance to itself. In the case of extraneous foreign antigens such as allergens, antigen "reminders" can be given at regular intervals.

In accordance with the present invention, an antibody or fragment thereof or molecule of the type hereinabove described may be administered in vivo alone or in combination with another compound(s) as described herein, to inhibit the activation and proliferation of T-cells, and decrease the density of functional CD4 expression on the cell surface and/or affect signal transduction thereby reducing the functionality of CD4+ T lymphocytes and/or the number of CD4+ T lymphocytes.

Thus, for example, in an in vivo procedure, such antibodies are administered to prevent and/or inhibit an immune response and thereby inhibit T cell activation and proliferation.

In accordance with an aspect of the invention, an antibody or fragment thereof or molecule of the type hereinabove described may be administered ex vivo alone or in combination with another compound(s) as described herein to decrease the density of functional CD4+ expression on the cell surface and/or affect signal transduction, thus reducing the functionality of CD4+ T lymphocytes and/or the number of CD4+ cells of the donor cells. By way of example and not limitation, in an ex vivo procedure, such antibodies or fragments or derivatives thereof or molecules would be infused into donor bone marrow prior to transplantation to prevent the onset of graft versus host disease upon transplantation.

The antibody or fragment thereof is generally administered in a pharmaceutically acceptable carrier alone or in combination with another compound(s) as described herein. As representative examples of such carriers, there may be mentioned normal saline solution, buffers, etc. Such pharmaceutical carriers are well known in the art and the selection of a suitable carrier is deemed to be within the scope of those skilled in the art from the teachings contained herein.

The TRX1 antibody or other antibody of the present invention may be administered in vivo intravenously, subcutaneously, or by intramuscular administration, etc alone or in combination with a drug, treatment or method as described herein.

As hereinabove indicated, TRX1 antibody or other antibody of the present invention is administered in vivo in an amount effective to inhibit an immune response against an antigen(s) alone or in combination with another compound(s) as described herein. The term an "effective amount" for purposes of this application shall mean that amount of antibody capable of producing the desired effect. In general, such antibody is administered in an amount of at least 0.1 milligram per dose. It is to be understood that lower amounts could be used. In addition after the initial treatment, the hereinabove described amounts may be reduced for subsequent treatments, if any. Thus the scope of the invention is not limited by such amounts. However, in order to induce tolerance in a primate, the antibody should be used in amounts as hereinabove described.

The TRX1 antibody or other antibody of the present invention may be employed alone or in combination with another compound(s) as described herein to induce tolerance to an antigen. The term "tolerance", as used herein, means that a T-cell non-response persists against an antigen after stopping the antibody treatment, even in the case of challenge. If needed, however, booster or reinforcing doses of the antibody may be given in order to maintain such tolerance.

The techniques of the present invention for inhibiting the activation of T-cells may be employed alone or in combination with other treatments, drugs or methods; for example other treatments, drugs or methods for inhibiting the activation of T-cells or inhibiting graft rejection or graft versus host disease or in treating various autoimmune diseases. Some examples of such drugs, treatments or methods used in combination with a compound to induce tolerance in a primate include but are not limited to Rituxan™ (Genentech); an antibody specific for B cell; an antibody specific for plasma cells, including but not limited to ID4 (Research Diagnostics); CellCept™(Roche); cyclosporine; rapamycin; anti-CD40L; anti-IL12; anti-IL18; anti-interferon-gamma; a proteosome inhibitor; an antagonist of CXCR3; 15-deoxyspergualin; FK506. monoclonal antibodies directed against co-stimulatory molecules such as CD2, CD8 and CD28, as well as monoclonal antibodies directed against adhesion molecules.

The antibodies of the present invention also may be employed in a method of selecting for or determining the presence of CD4 positive cells in a sample, such a blood sample, for example. In such method, a sample is contacted with the molecule or antibody, and the presence of CD4 positive cells is determined, and/or CD4 positive cells then can be selected or isolated form the sample.

In a preferred embodiment, the TRX1 antibody or an antibody that binds to the same epitope as TRX1 is employed alone or in combination with a drug, treatment or method as described herein to induce tolerance against an antigen(s) in a primate (in particular a human).

EXAMPLES

The invention now will be described with respect to the following examples; however, the scope of the present invention is not intended to be limited thereby.

Example 1

A cDNA library was constructed from the mouse hybridoma NSM 4.7.2.4 using the Superscript plasmid system (Gibco/BRL, cat. no. 82485A) according to the manufacturer's suggested protocol. Heavy and light chain cDNAs were cloned from the library by DNA hybridization using as probes rat heavy and light chain gene cDNAs from the rat hybridoma YTS 177.

The rat heavy and light chain gene cDNAs of YTS 177 were isolated from the expression vector pHA Pr-1 as BamH1/Sal 1 fragments and labeled with 32P and used independently to screen the NSM 4.7.2.4. cDNA library using standard molecular biology techniques (Sambrook, et al., Molecular Cloning, A. Laboratory Manual, 3rd edition, Cold Spring Harbor Laboratory Press, Cold Spring Harbor, N.Y. (2001); Ausubel, et al., Current Protocols in Molecular Biology, John Wiley & Sons, New York (2001).) Sequence analysis of the cDNAs derived from the NSM 4.7.2.4 cDNA library confirmed the NSM 4.7.2.4 heavy chain to be mouse gamma-1 subclass and the NSM 4.7.2.4 light chain to be kappa. The NSM 4.7.2.4 heavy and light V regions (VH and VL, respectively) were reshaped to the human VH and VL regions with the best fit " " or highest sequence similarity in the framework regions to that of the mouse. For the light chain, human antibody HSIGKAW (from EMBL) with a sequence similarity of 79%, was used (LA Spatz et al., 1990 J. Immunol. 144:2821-8). The sequence of HSIGKAW VL is:

MVLQTQVFISLLLWISGAYGDIVMTQSP-
DSLAVSLGERATINCKSSQSLLYS SNNKNYLAW-
YQQKPGQPPKLLIYWASTRESGVPDRF-
SGSGSGTDFTLTISS
LQAEDVAVYYCQQYYSTPPMFGQGTKVEIKRT (SEQ ID NO: 1)

D start of framework 1

Q changed to G

For the heavy chain, human antibody A32483 (From GenBank) with a sequence similarity of 74%, was used (Larrick, et al., Biochem. Biophys. Res. Comm., Vol. 160, pgs. 1250-1256 (1989)). The sequence of A32483 VH is:

LLAVAPGAHSQVQLVQSGAEVKKPGAS-
VKVSCKASGYTFTNYYMHWVRQ APGQGLEWMGI-
INPSGNSTNYAQKFQGRVTMTRDTST-
STVYMELSSLRSE
DTAVYYCAREKLATTIFGVLIITGMDY-
WGQGTLVTVSSGSASA (SEQ ID NO:2)

Q start of framework 1

For the humanization process, anti-CD4 light chain clone 77.53.1.2 (insert size 1 kb) and anti-CD4 heavy chain clone 58.59.1 (insert size 1.7 kb) were chosen from the cDNA library and inserts isolated from the pSport vector as Sal I/Not I fragments and cloned into M13mp18 vector to produce single stranded DNA for sequencing and template for mutagenesis. The humanization of NSM 4.7.2.4 was performed by site-directed mutagenesis of the mouse cDNA using a kit from Amersham International (RPN 1523) according to the manufacturer's suggested protocol.

Mutagenesis of the VL gene framework regions was performed using five oligonucleotides ranging in length from 29 to 76 bases. The oligos used were:

```
Primer #1998 76 bases
5'-TGA CAT TGT GAT GAC CCA ATC TCC AGA TTC TTT GGC
TGT GTC TCT AGG TGA GAG GGC CAC CAT CAA CTG CAA
GGC C
(SEQ ID NO:3)

Primer #1999 29 bases
5'-TGA ACT GGT ATC AAC AGA AAC CAG GAC AG
(SEQ ID NO:4)

Primer #2000 28 bases
5'-AGA GTC TGG GGT CCC AGA CAG GTT TAG T
(SEQ ID NO:5)

Primer #2001 42 bases
5'-GTC TTC AGG ACC CTC CGA CGT TCG GTG GAG GTA CCA
AGC TGG
(SEQ ID NO:6)

Primer #2008 52 bases
5'-CAC CCT CAC CAT CAG TTC TCT GCA GGC GGA GGA TGT
TGC AGT CTA TTA GTG T
(SEQ ID NO:7)
```

The oligos were phosphorylated and mutagenesis performed in three steps using no more than two oligos per step to introduce changes according to the following procedure:

(1) Annealing phosphorylated mutant oligos to ssDNA template
(2) Polymerization
(3) Filtration to remove single-stranded DNA
(4) Nicking non mutant strand with Nci I
(5) Digestion of non-mutant strand with Exo III
(6) Repolymerization of gapped DNA
(7) Transformation of competent JM101
(8) Sequencing of clones Mutations were confirmed by single strand DNA sequencing using M13 primers −20 and −40 and also the mutagenic primers #1999 and #2000.

A Sal I site at the 5' end of the variable region was changed to Hind III by linker oligos #2334 and #2335 to allow cloning of the variable region as a Hind III/Kpn I fragment into the light chain constant region of CAMPATH-1H.

```
Primer #2334 24 bases
5'-AGC TTT ACA GTT ACT GAG CAC ACA
(SEQ ID NO:8)

Primer #2335 24 bases
5'-TCG ATG TGT GCT CAG TAA CTG TAA
(SEQ ID NO:9)
```

Mutagenesis of the VH gene framework regions was performed using five oligonucleotides ranging in length from 24 to 75 bases. The oligos used were:

```
Primer #2003 75 bases
5'-GGT TCA GCT GGT GCA GTC TGG AGC TGA AGT GAA GAA
GCC TGG GGC TTC AGT GAA GGT GTC CTG TAA GGC TTC
TGG
(SEQ ID NO:10)

Primer #2004 52 bases
5'-AGC TGG GTG AGG CAG GCA CCT GGA CAG GGC CTT GAG
TGG ATG GGA GAG ATT T
(SEQ ID NO:11)

Primer #2005 60 bases
5'-CAA GGG CAG GGT CAC AAT GAC TAG AGA CAC ATC CAC
CAG CAC AGT CTA CAT GGA ACT CAG
(SEQ ID NO:12)

Primer #2006 44 bases
5'CAG CCT GAG GTC TGA GGA CAC TGC GGT CTA TTA CTG
TGC AAG A
(SEQ ID NO:13)

Primer #2007 24 bases
5'-GCC AAG GGA CAC TAG TCA CTG TGT
(SEQ ID NO:14)
```

Mutagenesis was carried out as described above for the light chain again using no more than two oligos at a time to introduce the changes. Mutations were confirmed by single strand DNA sequencing using M13 primers −20 and −40 as well as the mutagenic primers #2002 and #2004.

```
Primer #2002 was used to correct a reading frame
error in starting clone 58.59.1.
Primer #2002 39 bases
5'-ACT CTA ACC ATG GAA TGG ATC TGG ATC TTT CTC CTC
ATC
(SEQ ID NO:15)
```

```
Primer #2380 was used to correct extra mutation
added by #2004 which was missed in the first se-
quencing.
Primer #2380 39 bases
5'-TCA CTG CCT ATG TTA TAA GCT GGG TGA GGC AGG CAC
CTG
(SEQ ID NO:16)
```

As with the light chain, the heavy chain 5' Sal I site was changed to Hind III using linker oligo's #2334 and #2335 to allow cloning of the heavy chain variable region as Hind III/Spe I (site introduced by primer #2007) fragment into the heavy chain constant region of CAMPATH-1H.

Construction of Heavy Chain

The following samples of DNA were used

1. Plasmid 1990

Human gamma-1 heavy chain constant region gene cloned into pUC18 (obtained from Martin Sims, Wellcome Foundation Ltd).

2. Plasmid 2387

Reshaped heavy chain of NSM 4.7.2.4 containing human framework regions and mouse gamma 1 constant region.

A Sal I site in the reshaped CD4 heavy chain was altered to a Hind III site. The variable region gene was excised by digestion with Hind II/Spe I and ligated with the constant region gene in plasmid 1990 to give a complete humanized heavy chain (plasmid 2486). The heavy chain gene was cut out of this plasmid with Hind III/EcoR I and ligated with the expression vector pEE6.

Construction of Light Chain

The following samples of DNA were used.

1. Plasmid 2028

CAMPATH-1H light chain gene cloned into M13 mp18 at Sal I/BamH I restriction site.

2. Plasmid 2197

Reshaped light chain of NSM 4.7.2.4 containing human framework regions and mouse kappa constant region. A Kpn I site already had been introduced between variable and constant portions of this gene.

A Kpn I restriction site was introduced into the CAMPATH 1H light chain gene corresponding to the site in plasmid 2197 and an EcoR I site was introduced at the 3' end of the constant region. The constant region gene was excised from this plasmid (2502) by digestion with Hind III/Kpn I.

Meanwhile a Sal I site in plasmid 2197 was changed to a Hind III site (this step had to be repeated because a frameshift mutation inadvertently was introduced the first time). The new plasmid (2736) was digested with Hind III/Kpn I. The CD4 variable region fragment was cloned into a plasmid containing the kappa constant region gene from plasmid 2502 to give a complete humanized light chain (plasmid 2548). The light chain gene was cut out from this plasmid with Hind III/EcoR I and ligated with the expression vector pEE12 to give plasmid 2798.

Ligation of Heavy and Light Chains and Expression in NSO Cells

The heavy chain gene was excised from the pEE6 vector by digestion with Sal I/Bgl II and cloned into the light chain pEE12 vector which had been digested with BamH I/Sal I.

The final vector construct was checked by restriction digests with Hind III, EcoR I, Sal I, BamH I, Bgl II and Spe I for the presence of the expected fragments, including 700 bp light chain, 1400 bp heavy chain, 2300 bp fragment of pEE6 and 7000 bp fragment of pEE12.

The pEE12 vector was linearised by digestion with Sal I and transferred into NSO cells by electroporation, following a standard protocol (Celitech 1991) except that the selection medium was slightly modified, being based on IMDM rather than DMEM. Transfectants were selected in medium lacking glutamine, supplemented with dialysed FCS, ribonucleosides, glutamic acid, and asparagine as recommended.

The transfection mixes were cultured in three 96-well plates, and of 36 growing wells which were tested, 5 were strongly positive for production of human heavy and light chains (18 others were positive for one or other, or weakly positive for both).

A clone, designated SDG/B7B.A.7 was selected and stored frozen but no further characterization has been done on this wild type antibody.

Construction of Mutant IgG1 Antibody Designated to Abolish Effector Functions

Due to concerns about side effects of other CD4 antibodies reported in various clinical trials, it was considered desirable to avoid the possibility of engaging Fc receptors. Human IgG4 is thought to have minimal Fc binding or complement-activating ability. However, experiments have show that it does engage Fc receptors in some individuals (Greenwood et al., Eur. J. Immunol., Vol. 23, pgs. 1098-1104, 1993), and clinical studies with a human IgG4 variant to CAMPATH-1H have demonstrated an ability to kill cells in vivo (Isaacs et al., Clin. Exp. Immunol., Vol. 106, pgs. 427-433 (1996)). To eliminate the possibility of binding Fc receptors, constructs were made with mutations in the IgG1 heavy chain constant region.

TRX1 has the mutations Leu236 to Ala and Gly238 to Ala, as shown in FIGS. 1D and 1E and FIGS. 3D and 3E. These particular residues were chosen because they were predicted to disrupt maximally binding to all three types of human Fc receptors for IgG.

Either mutation is sufficient to reduce binding to FcγRI (Woof, et al., Mol. Immunol, Vol. 332, pgs. 563-564 1986; Duncan, et al., Nature, Vol. 332, pgs. 563-564 1988; Lund, et al., J. Immunol, Vol. 147, pgs. 2657-2662 1991) or FcγRII (Lund et al., 1991; Sarmay et al., Mol. Immunol., Vol. 29, pgs. 633-639 1992) whereas Gly238 to Ala has the biggest effect on binding to FcγRIII (Sarmay et al., 1992).

The following samples of DNA were used.

1. Plasmid 2555 and Plasmid 2555 Mut.

Humanized VH region of NSM 4.7.2.4 cloned into pEE6 expression vector at a Hind III/Spe I restriction site. Plasmid 2555 then was mutated by site directed mutagenesis such that amino acid residue Asn101 was changed to Asp101, as shown in FIGS. 1D and 1E and FIGS. 3D and 3E. The resulting plasmid is plasmid 2555 Mut.

2. Plasmid 2798

Humanized VH region of NSM 4.7.2.4 joined to human kappa constant regions to give approx. 700 bp fragment cloned into pEE12 expression vector at a Hind III/EcoR I.

3. Plasmid MF4260

Human IgG1 heavy chain associated with the humanized CD18 VH region, having the mutations Leu236 to Ala and Gly238 to Ala as well as a Spe I restriction site introduced into framework region 4, cloned into pUC18.

The purpose of the Spe I restriction site is to allow separation and recombination of different variable regions.

The CD18 VH region gene was excised from plasmid MF 4260 by digestion with Spe I and Hind III and the remaining vector, now having only the relevant heavy chain constant region, was purified using Geneclean. It was ligated with the humanized VH region DNA of NSM 4.7.2.4 which had been isolated from plasmid 2555 Mut in the same way. The product was used to transform "Sure" cells and colonies were checked for the presence of the expected 1400 bp complete heavy chain insert.

The complete VH and constant region insert was excised from the pUC vector by digestion with Hind III and EcoR I. The 1400 bp fragment was purified using QiaexII (Qiagen) and then ligated in turn into the vector pEE6, which had previously been cut with the same enzymes.

The next step was to excise the CD4 heavy chain genes from the pEE6 vector and clone them into pEE12, already containing the humanized CD4 light chain gene (plasmid 2798). The pEE6 vector was digested with Sal I and Bgl II and the pEE12 vector was digested with Sal I and BamH I to create the appropriate sites for re-ligation.

The final vector construct was checked by restriction digests with Hind III, EcoR I, Sal I and Spe I for the presence of the expected fragment, i.e., 700 bp light chain, 1400 bp heavy chain, 2300 bp fragment of pEE6, and 7000 bp fragment of pEE12.

The pEE12 vector was linearized by digestion with Sal I and transfected into NSO cells by electroporation as above. The transfection mixes were cultured in six 96-well plates, and of 90 growing wells which were tested, all were positive for production of human heavy and light chains. At this stage a sample of the pEE12 vector DNA was digested with Sal I, precipitated with ethanol and transferred to the Therapeutic Antibody Centre (TAC).

Target Cells for Final Transfection

NSO cells were obtained directly from the ECACC (clone CB1782, accession number 85110503). A master cell bank (MCB) was prepared at the Therapeutic Antibody Centre, Churchill Hospital, Oxford, England.

Transfection and Selection of Final Transfectant

The pEE12 vector was transfected into NSO cells from the MCB by electroporation as hereinabove described. A total of $2 \times 10^7$ cells were transfected with 80 μg of linearized plasmid DNA in a final volume of 2.0 ml. The transfection mix was plated out in twelve 96-well plates and fed with selective medium according to the standard protocol (The Cell Tech Glutamine Synthetase Gene Expression System, Version 2—Expression from Myeloma Cells, Revision 6.) Six plates received selective medium containing 10 (M methionine sulfoximine (MSX).

Purification of the Antibody

Culture supernatant is purified by using a Biopilot chromatography system (Pharmacia) in three steps as follows:

(1) Affinity chromatography on a column of Protein A-Sepharose Fast Flow (2) Ion exchange chromatography on S-Sepharose Fast Flow (3) Size exclusion chromatography on Superdex 20.

The purified product was filtered and pooled into a single biocontainer.

Throughout the purification process, precautions are taken to ensure that the system remains aseptic. All buffers and reagents are passed through a 0.2 micron membrane filter and the purified product is also passed through a 0.2 micron filter before being pooled. After a batch of antibody has been processed, the entire chromatography system and columns are sanitized with 0.5M NaOH, washed with sterile PBS and stored in 20% ethanol. Before it is used again, the ethanol is washed out with sterile PBS and a complete trial run is carried out. Samples of buffers and column eluates are checked for endotoxin level.

Example 2

Construction of TRX1 Antibody Starting from Nucleotide Sequence Cloning of Human Constant Regions Heavy Chain Constant Region The human gamma 1 heavy chain constant region (IgG1) is amplified from human leukocyte cDNA (QUICK-Clone™ cDNA Cat. No. 7182-1, Clontech) using the following primer set and cloned into pCR-Script (Stratagene). The plasmid containing the human gamma 1 heavy chain constant region in pCR-Script is designated pHCγ-1.

```
primer hcγ-1
             Spe I
5'primer:    5'-ACT AGT CAC AGT CTC CTC AGC
             (SEQ ID NO:17)

primer hcγ-2
             EcoR I
3'primer:    5'-GAA TTC ATT TAC CCG GAG ACA G
             (SEQ ID NO:18)
```

Non-Fc binding mutations (Leu236Ala, Gly238Ala) are made in the heavy chain constant region by site-directed mutagenesis using the following primer and the Transformer™ Site-Directed Mutagenesis Kit from Clontech (Cat. No. K1600-1). The plasmid containing the human gamma 1 heavy chain non-Fc binding mutant constant region in pCR-Script is designated pHCγ-1Fcmut.

```
primer hcγ-3
Fc mut oligo:  5'-CCG TGC CCA GCA CCT GAA CTC
               GCG GGG GCA CCG TCA GTC TTC CTC
               CCC C
               (SEQ ID NO:19)
```

Light Chain Constant Region

The human kappa light chain constant region is amplified from human leukocyte cDNA (QUICK-Clone™ cDNA Cat. No. 7182-1, Clontech) using the following primer set and cloned into pCR-Script (Stratagene). The plasmid containing the human kappa light chain constant region in pCR-Script is designated pLCκ-1.

```
primer lcκ-1
             Kpn I
5'primer:    5'-GGT ACC AAG GTG GAA ATC AAA CGA AC
             (SEQ ID NO:20)

primer lcκ-2
             Hind III
3'primer:    5'-AAG CTT CTA ACA CTC TCC CCT GTT G
             (SEQ ID NO:21)
```

Synthesis, Construction and Cloning of TRX1 Variable Regions

The heavy and light chain variable regions are constructed from a set of partially overlapping and complementary synthetic oligonucleotides encompassing the entire variable regions. The oligonucleotide set used for each variable region is shown below.

Heavy Chain Variable Region Synthetic Oligonucleotides

Coding Strand Heavy Chain Variable Region Primers

```
primer hv-1 (1-72)+6 nucleotide linker
5'-aagctt ATG GAA TGG ATC TGG ATC TTT CTC CTC ATC
CTG TCA GGA ACT CGA GGT GTC CAG TCC CAG GTT CAG
CTG GTG
(SEQ ID NO:22)

primer hv-2 (120-193)
5'-C TGT AAG GCT TCT GGA TAC ACA TTC ACT GCC TAT
GTT ATA AGC TGG GTG AGG CAG GCA CCT GGA CAG GGC
CTT G
(SEQ ID NO:23)

primer hv-3 (223-292)
5'-GGT AGT AGT TAT TAT AAT GAG AAG TTC AAG GGC
AGG GTC ACA ATG ACT AGA GAC ACA TCC ACC AGC ACA G
(SEQ ID NO:24)

primer hv-4 (322-399)
5'-GAG GAC ACT GCG GTC TAT TAC TGT GCA AGA TCC
GGG GAC GGC AGT CGG TTT GTT TAC TGG GGC CAA GGG
ACA CTA GT
(SEQ ID NO:25)
```

Non-Coding Strand Heavy Chain Variable Region Primers

```
primer hv-5 (140-51)
5'-GTG TAT CCA GAA GCC TTA CAG GAC ACC TTC ACT
GAA GCC CCA GGC TTC TTC ACT TCA GCT CCA GAC TGC
ACC AGC TGA ACC TGG GAC TGG
(SEQ ID NO:26)

primer hv-6 (246-170)
5'-CTT CTC ATT ATA ATA ACT ACT ACC GCT TCC AGG
ATA AAT CTC TCC CAT CCA CTC AAG GCC CTG TCC AGG
TGC CTG CC
(SEQ ID NO:27)

primer hv-7 (342-272)
5'-GTA ATA GAC CGC AGT GTC CTC AGA CCT CAG
GCT GCT GAG TTC CAT GTA GAC TGT GCT GGT GGA TGT
GTC TC
(SEQ ID NO:28)
```

Light Chain Variable Region Synthetic Oligonucleotides

Coding Strand Light Chain Variable Region Primers

```
primer lv-1 (1-63)+6 nucleotide linker
5'-gaattc ATG GAG ACA GAC ACA ATC CTG CTA TGG GTG
CTG CTG CTC TGG GTT CCA GGC TCC ACT GGT GAC
(SEQ ID NO:29)

primer lv-2 (93-158)
5'-GGC TGT GTC TCT AGG TGA GAG GGC CAC CAT
CAA CTG CAA GGC CAG CCA AAG TGT TGA TTA TGA TGG
(SEQ ID NO:30)

primer lv-3 (184-248)
5'-CAG AAA CCA GGA CAG CCA CCC AAA CTC CTC
ATC TAT GTT GCA TCC AAT CTA GAG TCT GGG GTC CC
(SEQ ID NO:31)
```

-continued

```
primer lv-4 (275-340)
5'-GGA CAG ACT TCA CCC TCA CCA TCA GTT CTC TGC AGG
CGG AGG ATG TTG CAG TCT ATT ACT GTC AGC
(SEQ ID NO:32)
```

Non-Coding Strand Light Chain Variable Region Primers

```
primer lv-5 (109-43)                    (SEQ ID NO:33)
5'-CAC CTA GAG ACA CAG CCA AAG AAT CTG GAG ATT GGG
TCA TCA CAA TGT CAC CAG TGG AGC CTG GAA C primer lv-6 (203-138)                   (SEQ ID NO:34)
5'-GGT GGC TGT CCT GGT TTC TGT TGA TAC CAG TTC ATA
TAA CTA TCA CCA TCA TAA TCA ACA CTT TGG primer lv-7 (294-228)                   (SEQ ID NO:35)
5'-GGT GAG GGT GAA GTC TGT CCC AGA CCC ACT GCC ACT
AAA CCT GTC TGG GAC CCC AGA CTC TAG ATT G primer lv-8 (378-319)                   (SEQ ID NO:36)
5'-GGT ACC TCC ACC GAA CGT CGG AGG GTC CTG AAG ACT
TTG CTG ACA GTA ATA GAC TGC AAC
```

After HPLC purification and removal of organic solvents the oligonucleotides are resuspended in TE pH8.0 and phosphorylated. An aliquot of each oligonucleotide in the respective variable region set then are combined in equal molar amounts. The oligonucleotide mixtures are heated to 68° C. for 10 minutes and allowed to cool slowly to room temperature. The annealed oligonucleotides then are extended to produce double stranded variable region DNA fragments. For the extension, dNTPs are added to a final concentration of 0.25 mM followed by an appropriate volume of 5× T4 DNA polymerase buffer [165 mM Tris acetate, pH 7.9, 330 mM sodium acetate, 50 mM magnesium acetate, 500 mg/ml BSA, 2.5 mM DTT] and 4 units of T4 DNA polymerase. The mixture is incubated at 37° C. for 1 hour followed by heat inactivation of the T4 DNA polymerase at 65° C. for 5 minutes.

The double stranded DNA is ethanol precipitated and resuspended in the same volume of TE pH 8.0. An appropriate volume of 5× T4 DNA ligase buffer [250 mM Tris-HCl, pH7.6, 50 mM MgCl2, 5 mM ATP, 5 mM DTT, 25% w/v polyethylene glycol-8000] then is added to the double stranded DNA followed by 2 units of T4 DNA ligase and the mixture incubated for 1 hour at 37° C. to ligate the extended fragments. The T4 DNA ligase then is heat inactivated at 65° C. for 10 minutes. The variable region DNA fragments then are phenol extracted, ethanol precipitated, and resuspended in TE, pH 8.0 and cloned into pCR-Script (Stratagene). The resulting plasmid containing the heavy chain variable region is designated pHV-1 and the plasmid containing the light chain variable region was designated pLV-1.

The final heavy and light chain expression vectors are constructed in pcDNA 3.1 (Invitrogen). For the heavy chain expression vector, the Fc mutated constant region is released from plasmid pHC-1 Fcmut by digestion with Spe I and EcoR I and isolated by agarose gel electrophoresis. The heavy chain variable region is released from plasmid pHV-1 by digestion with Hind III and Spe I and isolated by agarose gel electrophoresis. The two fragments in equal molar amounts are ligated into the Hind III/EcoR I sites of pcDNA3.1(+) (Invitrogen) using standard molecular biology techniques. The resulting TRX1 heavy chain expression vector is designated pTRX1/HC.

Similarly, for the light chain expression vector, the light chain constant region is released from plasmid pLC-1 by digestion with Kpn I and Hind III followed by agarose gel purification. The light chain variable region is released from pLV-1 by digestion with EcoR I and Kpn I followed by agarose gel purification. The two light chain fragments in equal molar amounts are ligated into the EcoR I/Hind III sites of pcDNA3.1(−) (Invitrogen) using standard molecular biology techniques yielding the TRX1 light chain expression vector pTRX1/LC.

For production of TRX1 antibody, the TRX1 heavy chain and TRX1 light chain expression plasmids are cotransfected into CHO cells using standard molecular biology techniques.

Example 3

A humanized antibody is shown in FIGS. 2A, 2C, 2D, and 2F is produced by a procedure similar to that of Example 1. The humanized antibody is an aglycosylated antibody.

Example 4

A humanized antibody as shown in FIGS. 4A, 4C, 4D and 4F is produced by a procedure similar to that of Example 1. The humanized antibody is an aglycosylated antibody.

Example 5

A mixed lymphocyte reaction (MLR) is used to generate human lymphocytes primed to recognize foreign human histocompatibility antigens. To generate this reaction human peripheral blood lymphocytes are isolated from heparinized whole blood from two different individuals (Donor A and Donor B) using Ficoll density gradient centrifugation or a similar method. Lymphocytes from Donor B are adjusted to 107/ml in RPMI 1640 media with no serum but containing 50 ug/ml of mitomycin C. The cells are incubated at 37° C. for 30 minutes and are then washed out of the media with mitomycin C in three centrifugations in RPMI 1640 with 10% Donor A plasma. Cells from Donor A, which have not been treated with mitomycin C, are adjusted to 4×106/ml in RPMI 1640 with 10% Donor A plasma. After washing, the mitomycin C treated lymphocytes from Donor B are adjusted to 4×106/ml in RPMI with 10% Donor A plasma. Equal volumes of Donor A and Donor B cells are combined and placed into the compound, or said compound in combination with a drug, treatment or method, to be tested ("Test Compound") suitably sized tissue culture flasks. Flasks with and without Test Compound are then incubated at 37° C. in 5% CO2 in air for 7-10 days. This is the primary mixed lymphocyte reaction.

It can be observed that the cells in the primary MLR will become activated and begin to divide between days 3-7 and following a period of active proliferation, the cells will return to a more resting state. The time of this can vary, however, cells will usually return to rest between days 7-10. Once cells appear to be at rest, cells from primary MLR flasks with and without Test Compound can be recovered by centrifugation and resuspended in RPMI 1640 with 10% Donor A plasma at 4×106/ml. Fresh PBL can be prepared by Ficoll density centrifugation from heparinized whole blood from Donor B and again inactivated with mitomycin C, the inactivated Donor B cells are adjusted to 4×106/ml in RPMI 1640 with 10% Donor A plasma. For the second MLR, equal volumes of primary MLR cells (cells from the primary MLR which was performed in the absence of Test Compound) are mixed with mitomycin C inactivated Donor B cells.

If the primary MLR cells (cells obtained from an MLR which was performed in the absence of Test Compound) are labeled with CFSE, a green fluorescent dye which is imported into living cells where it is acted upon by an enzyme and then reacts with cellular proteins, the number of cell divisions experienced over time by the labeled cells is reflected in the reduction of green label associated with each cell. If CFSE labeled MLR cells are stimulated in a secondary MLR to which has been added cells derived from the Test Compound treated primary MLR at a ratio of 2:1 to 10:1 MLR to Test Compound derived MLR cells, inhibition of the proliferation of the CFSE labeled MLR cells will be observed in the secondary MLR within 3-4 days of stimulation when compared with proliferation of CFSE labeled MLR cells stimulated in the secondary MLR in the absence of the Test Compound derived cells.

The cells produced in the primary MLR and secondary MLR (as well as cells provided in control MLRs) are analyzed for CD4+ CD25+ cells as hereinabove described.

When TRX1 was tested as hereinabove described, as compared to control, CD4+ CD25+ cells were reduced by more than 60% in the primary MLR and by more than 20% in the secondary MLR, and in the secondary MLR, as compared to control, the production of IL-2, IL-4 and IL-12 was essentially eliminated and the production of IL-5, IL-13, IFN, gamma and TNF alpha was reduced by more than 50%.

Example 6

The induction of antigen specific immunological tolerance in non-human primates by the use of the non-depleting anti-CD4 monoclonal antibody, TRX1, was demonstrated in the following study. Baboons (*Papio anubus*) were randomly divided into seven groups of three animals. The seven groups were comprised of four experimental groups designated Groups 4, 6, 7 and 8 and three control groups designated Groups 1, 5, and 9. The study was comprised of 2 phases, an Immunization/Tolerization phase followed by a Challenge phase. For the Immunization/Tolerization phase of the study, Groups 4, 6, 7 and 8 were immunized with 3 doses of Antigen 1 (10 mg/kg in saline), one dose each on day 0, day 4, and day 8. Antigen 1 is polyvalent aggregated horse IgG (Antivenin) given intravenously (i.v.) for the first dose and subcutaneously (SC) for all subsequent doses. During this phase of the protocol: groups 4, 6, 7 & 8 also received 4 doses i.v. of the non-depleting anti-CD4 monoclonal antibody, TRX1, as follows: Group 4 received 4 doses of 20 mg/kg at day −1, day 4, day 8 and day 12; Group 6 received 1 mg/kg of TRX1 on day −1, day 3, day 8, and day 12. Group 7 received 10 mg/kg on day −1, day 3, day 8 and day 12. Group 8 received 40 mg/kg on day −1, day 3, day 8, and day 12.

Control Groups 1 and 5 were treated as follows during the Immunization/Tolerization phase of the protocol: Group 1 received 3 doses of Antigen 1 at 10 mg/kg, one dose each on day 0, day 4, and day 8. Group 5 received 4 doses i.v. of TRX1 antibody, 20 mg/kg, one dose each on day −1, day 4, day 8, and day 12. Group 9 received four doses IV of TRX1 antibody, 40 mg/kg, one dose each on day −1, day 4, day 8, and day 12.

Blood was collected prior to each injection of Antigen 1 and/or TRX1 and weekly thereafter to assess serum level of TRX1 by ELISA, the pharmacodynamic effects of TRX1 treatment on the level of circulating lymphocyte subsets, as well as the percentage of CD4 receptor occupancy by flow cytometry, and the baboon antibody response to Antigen 1 by ELISA.

The immune response to antivenin for the first 68 days of the study for Groups 1, 4, 6, 7, and 8, as measured in antibody titer, is shown in FIG. 5.

The Challenge phase of the study was initiated once the serum levels of TRX1 reached undetectable levels. For the Challenge phase, all animals in all groups were challenged (Day 68) with Antigen 1 (10 mg/kg, SC) and Antigen 2 (1.7 ml/kg). Antigen 2 is a 10% saline solution of sheep red blood cells given IV for one dose. Challenges with Antigen 1 were repeated on day 95 and day 135 for Control Groups 5 and 9 and Test Groups 4 and 8. Blood was collected prior to each challenge to assess for serum levels of Antigen 1, TRX1, and the baboon antibody response to Antigen 1 and Antigen 2.

Figure 6:
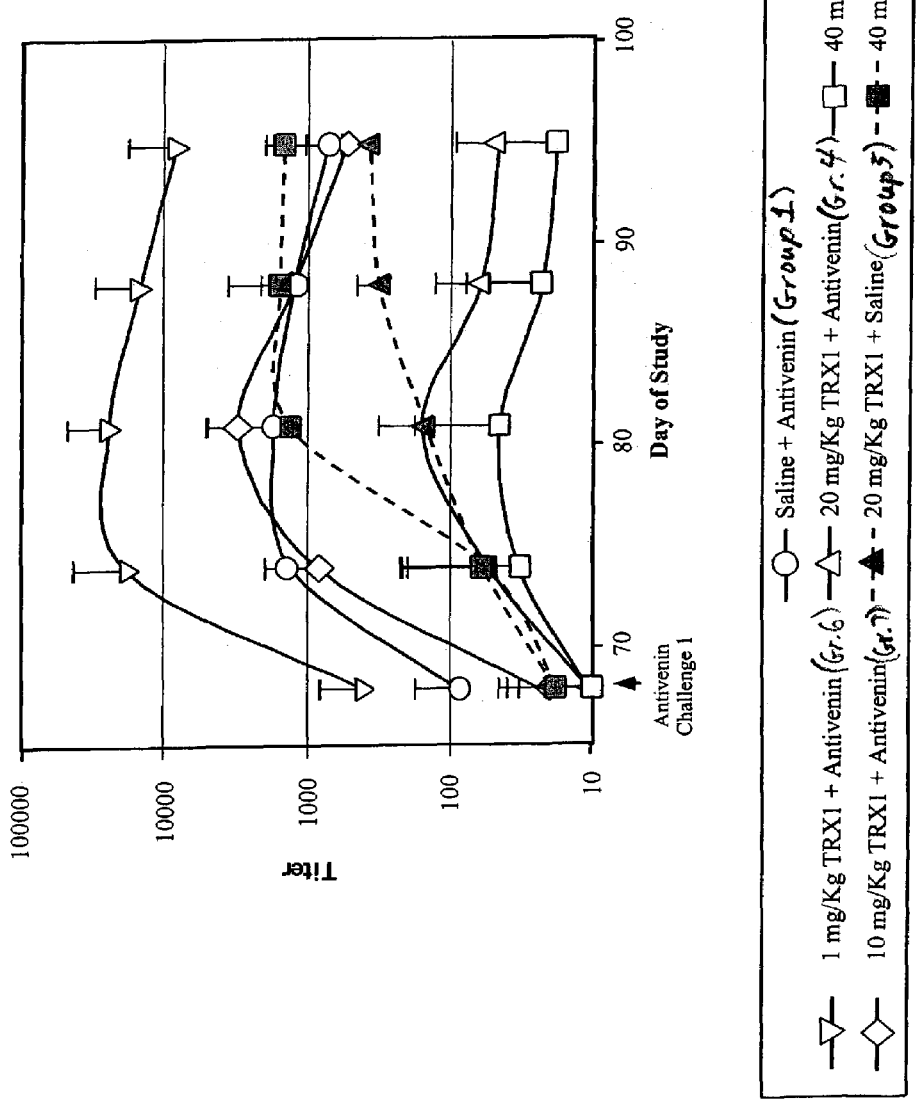
FIG. 6 shows the immune response to antivenin, subsequent to an antivenin and sheep red blood cell challenge, to groups of baboons which were given antivenin, alone or in combination with TRX1 antibody, 68 days before the challenge.
Figure 7:
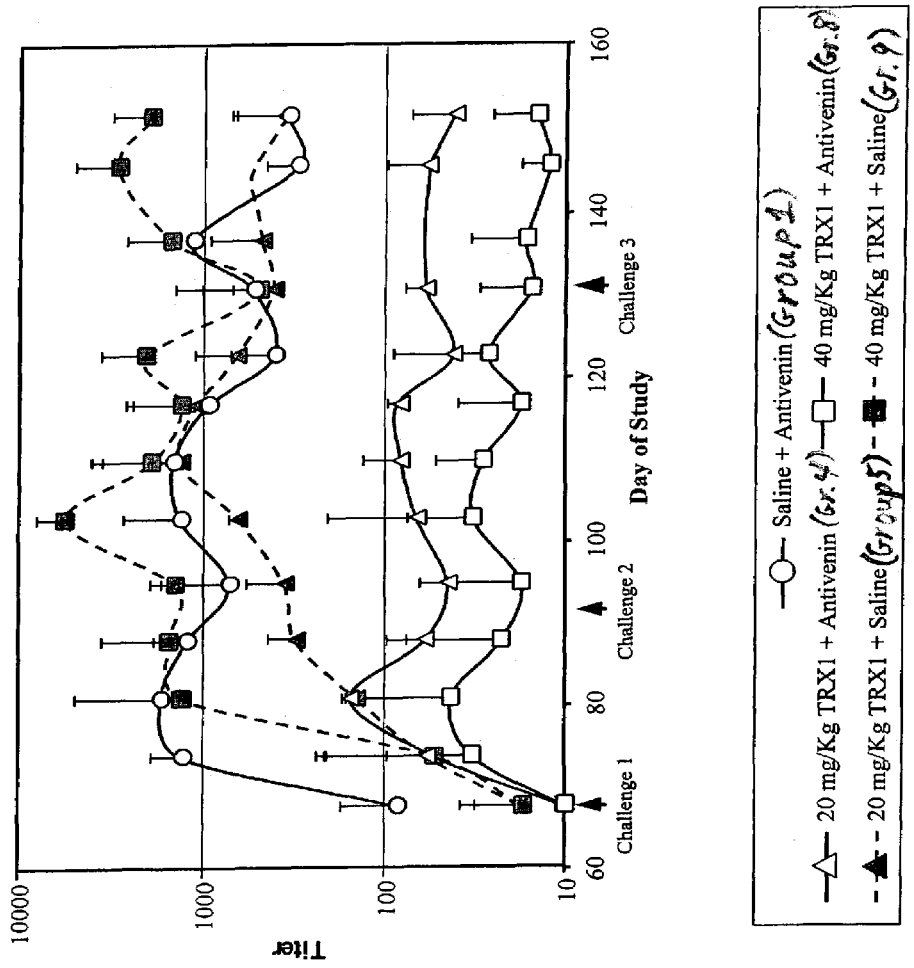
FIG. 7 shows the immune response to antivenin, subsequent to each of three antivenin challenges, to groups of baboons which were given antivenin, alone or in combination with TRX1 antibody, 68 days before the first challenge.

FIG. 6 shows the immune response to antivenin, as measured in antibody titer, for all groups after the first challenge (days 68-95). FIG. 7 shows the immune response to antivenin, as measured in antibody titer, for Groups 1, 4, 5, 8, and 9, after Challenge 1, Challenge 2, and Challenge 3.

Figure 8:
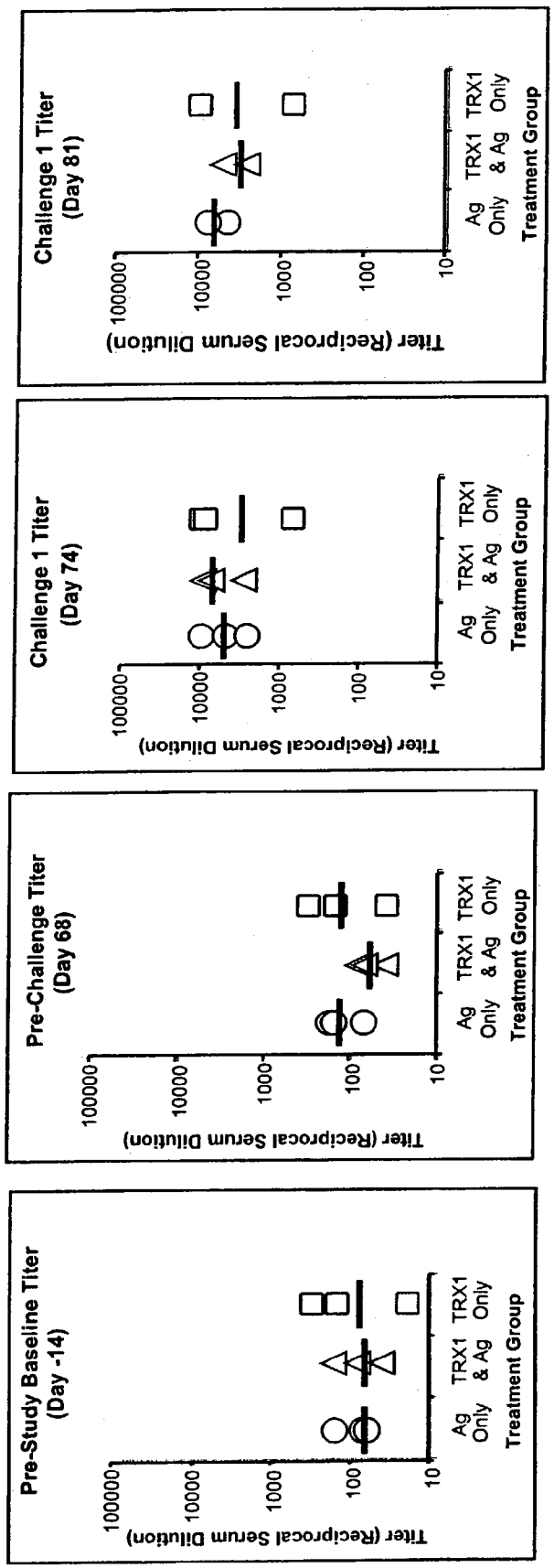
FIG. 8 is a chart depicting immune response to sheep red blood cells after TRX1 tolerization against antivenin.

The results of the immune response of groups 1, 4 and 5 to sheep red-blood cells is shown in FIG. 8.

The disclosures of all patents, publications (including published patent applications), depository accession numbers, and database accession numbers are hereby incorporated by reference to the same extent as if each patent, publication, depository accession number, and database accession number were specifically and individually incorporated herein by reference.

Example 7

The induction of tolerance by the administration of TRX1 in combination with a drug, treatment or method is exemplified by the following. A drug, treatment or method such as, but not limited to CellCept™ can be used in conjunction with a compound of the present invention, such as, but not limited to TRX1 to induce tolerance in a mammal, such as but not limited to a rodent.

Groups of rodents, such as, but not limited to C57BL6, can be treated with a priming dose of an antigen to which tolerance is required, such as human immunoglobulin G (hIgG). A appropriate single dose of hIgG (e.g. 2 mg/kg) would be given by for example, iv injection 24 days prior to the tolerization regimen.

On day 25, the tolerization phase would begin, with mice being treated with either TRX1 or a combination of TRX1 and CellCept™, along with additional doses of hIgG. The dosing regimen may be as follows. Group I would be given TRX1 alone at a dose of 50 mg/kg on days 1, 3, 5, 7, 9 and 11. Group II would receive in addition to the TRX1 as above, injections of CellCept™ (50 mg/kg) on days 2-14. Group III would receive CellCept™ alone, dosed as above. Groups I, II and III would receive in addition to above, hIgG at 10 mg/kg at days 0, 4 and 8. Group IV would receive hIGg, dosed as above, alone. All doses would be give for example by iv injection.

The challenge phase would begin on day 118 when each group would be given, for example, an iv injection of hIgG at 5/mg/kg. Sera would be collected and assayed by any of a number of art-recognized methods to determine whether the treated animals were capable of mounting an antibody response to the hIgG. Additional challenges would be mounted on days 152 and 180 with, for example, an iv injection of hIgG at 5 mg/kg and ovalbumin at 5 mg/kg. If the animals had been tolerized to the hIgG, the levels of antibody specific for hIGg in the treated groups (Groups I, II and III) would be reduced compared to the control group (Group IV).

It is to be understood, however, that the scope of the present invention is not to be limited to the specific embodiments described above. The invention may be practiced other than as particularly described and still be within the scope of the accompanying claims.

What is claimed is:

1. An isolated anti-CD4 antibody which comprises the light chain CDR sequences of FIG. 4C (SEQ ID NO: 57) and the heavy chain CDR sequences of FIG. 4F (SEQ ID NO: 60).

2. An anti-CD4 antibody which comprises the light chain variable region sequence of FIG. 4C (SEQ ID NO: 57) and the heavy chain CDR sequences of FIG. 4F (SEQ ID NO: 60).

3. An anti-CD4 antibody which comprises the light chain CDR sequences of FIG. 4C (SEQ ID NO: 57) and the heavy chain variable region sequence of FIG. 4F (SEQ ID NO: 60).

4. An anti-CD4 antibody which comprises the light chain variable region sequence of FIG. 4C (SEQ ID NO: 57) and the heavy chain variable region sequence of FIG. 4F (SEQ ID NO: 60).

5. The anti-CD4 antibody of claim 1, wherein the anti-CD4 antibody comprises an Fc region that is aglycosylated.

6. The anti-CD4 antibody of claim 4, wherein the anti-CD4 antibody comprises an Fc region that is aglycosylated.

7. The anti-CD4 antibody of claim 4, wherein the anti-CD4 antibody comprises a constant region that does not comprise a glycosylation site.

8. The anti-CD4 antibody of claim 1 wherein the antibody is a humanized antibody.

9. The anti-CD4 antibody of claim 2 wherein the antibody is a humanized antibody.

10. The anti-CD4 antibody of claim 3 wherein the antibody is a humanized antibody.

11. The anti-CD4 antibody of claim 4 wherein the antibody is a humanized antibody.

12. The anti-CD4 antibody of claim 4 wherein the antibody is a single chain antibody or a bispecific antibody.

13. An anti-CD4 antibody wherein the anti-CD4 antibody comprises a heavy chain and a light chain selected from the group consisting of:
   a. a light chain comprising the amino acid sequence SEQ ID NO: 39 and a heavy chain comprising the amino acid sequence SEQ ID NO: 42;
   b. a light chain comprising the amino acid sequence SEQ ID NO: 45 and a heavy chain comprising the amino acid sequence SEQ ID NO: 48;
   c. a light chain comprising the amino acid sequence SEQ ID NO: 51 and a heavy chain comprising the amino acid sequence SEQ ID NO: 54; and
   d. a light chain comprising the amino acid sequence SEQ ID NO: 57 and a heavy chain comprising the amino acid sequence SEQ ID NO: 60.

* * * * *

UNITED STATES PATENT AND TRADEMARK OFFICE
CERTIFICATE OF CORRECTION

| | | |
|---|---|---|
| PATENT NO. | : 7,541,443 B2 | Page 1 of 1 |
| APPLICATION NO. | : 10/353708 | |
| DATED | : June 2, 2009 | |
| INVENTOR(S) | : Frewin et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 761 days.

Signed and Sealed this
Eighth Day of February, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,541,443 B2 | Page 1 of 1 |
| APPLICATION NO. | : 10/353708 | |
| DATED | : June 2, 2009 | |
| INVENTOR(S) | : Frewin et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1366 days.

Signed and Sealed this
Twenty-ninth Day of March, 2011

David J. Kappos
*Director of the United States Patent and Trademark Office*

SEQUENCE LISTING

<160> NUMBER OF SEQ ID NOS: 60

<210> SEQ ID NO 1
<211> LENGTH: 135
<212> TYPE: PRT
<213> ORGANISM: Homo sapiens

<400> SEQUENCE: 1

Met Val Leu Gln Thr Gln Val Phe Ile Ser
                  5                  10

Leu Leu Leu Trp Ile Ser Gly Ala Tyr Gly
                 15                  20

Asp Ile Val Met Thr Gln Ser Pro Asp Ser
                 25                  30

Leu Ala Val Ser Leu Gly Glu Arg Ala Thr
                 35                  40

Ile Asn Cys Lys Ser Ser Gln Ser Leu Leu
                 45                  50

Tyr Ser Ser Asn Asn Lys Asn Tyr Leu Ala
                 55                  60

Trp Tyr Gln Gln Lys Pro Gly Gln Pro Pro
                 65                  70

Lys Leu Leu Ile Tyr Trp Ala Ser Thr Arg
                 75                  80

Glu Ser Gly Val Pro Asp Arg Phe Ser Gly
                 85                  90

Ser Gly Ser Gly Thr Asp Phe Thr Leu Thr
                 95                 100

Ile Ser Ser Leu Gln Ala Glu Asp Val Ala
                105                 110

Val Tyr Tyr Cys Gln Gln Tyr Tyr Ser Thr
                115                 120

Pro Pro Met Phe Gly Gln Gly Thr Lys Val
                125                 130

Glu Ile Lys Arg Thr
                135

<210> SEQ ID NO 2
<211> LENGTH: 142
<212> TYPE: PRT
<213> ORGANISM: Homo sapiens

<400> SEQUENCE: 2

Leu Leu Ala Val Ala Pro Gly Ala His Ser
                  5                  10

Gln Val Gln Leu Val Gln Ser Gly Ala Glu
                 15                  20

Val Lys Lys Pro Gly Ala Ser Val Lys Val
                 25                  30

Ser Cys Lys Ala Ser Gly Tyr Thr Phe Thr
                 35                  40

Asn Tyr Tyr Met His Trp Val Arg Gln Ala
                 45                  50

Pro Gly Gln Gly Leu Glu Trp Met Gly Ile
                 55                  60

```
Ile Asn Pro Ser Gly Asn Ser Thr Asn Tyr
                65                  70

Ala Gln Lys Phe Gln Gly Arg Val Thr Met
                75                  80

Thr Arg Asp Thr Ser Thr Ser Thr Val Tyr
                85                  90

Met Glu Leu Ser Ser Leu Arg Ser Glu Asp
                95                 100

Thr Ala Val Tyr Tyr Cys Ala Arg Glu Lys
               105                 110

Leu Ala Thr Thr Ile Phe Gly Val Leu Ile
               115                 120

Ile Thr Gly Met Asp Tyr Trp Gly Gln Gly
               125                 130

Thr Leu Val Thr Val Ser Ser Gly Ser Ala
               135                 140

Ser Ala

<210> SEQ ID NO 3
<211> LENGTH: 76
<212> TYPE: DNA
<213> ORGANISM: Artificial
<220> FEATURE:
<223> OTHER INFORMATION: PCR primer

<400> SEQUENCE: 3
tgacattgtg atgacccaat ctccagattc tttggctgtg tctctaggtg agagggccac    60
catcaactgc aaggcc                                                    76

<210> SEQ ID NO 4
<211> LENGTH: 29
<212> TYPE: DNA
<213> ORGANISM: Artificial
<220> FEATURE:
<223> OTHER INFORMATION: PCR primer

<400> SEQUENCE: 4
tgaactggta tcaacagaaa ccaggacag                                      29

<210> SEQ ID NO 5
<211> LENGTH: 28
<212> TYPE: DNA
<213> ORGANISM: Artificial
<220> FEATURE:
<223> OTHER INFORMATION: PCR primer

<400> SEQUENCE: 5
agagtctggg gtcccagaca ggtttagt                                       28

<210> SEQ ID NO 6
<211> LENGTH: 42
<212> TYPE: DNA
<213> ORGANISM: Artificial
<220> FEATURE:
<223> OTHER INFORMATION: PCR primer

<400> SEQUENCE: 6
gtcttcagga ccctccgacg ttcggtggag gtaccaagct gg                       42

<210> SEQ ID NO 7
```

<211> LENGTH: 52
<212> TYPE: DNA
<213> ORGANISM: Artificial
<220> FEATURE:
<223> OTHER INFORMATION: PCR primer

<400> SEQUENCE: 7
caccctcacc atcagttctc tgcaggcgga ggatgttgca gtctattagt gt        52

<210> SEQ ID NO 8
<211> LENGTH: 24
<212> TYPE: DNA
<213> ORGANISM: Artificial
<220> FEATURE:
<223> OTHER INFORMATION: PCR primer

<400> SEQUENCE: 8
agctttacag ttactgagca caca        24

<210> SEQ ID NO 9
<211> LENGTH: 24
<212> TYPE: DNA
<213> ORGANISM: Artificial
<220> FEATURE:
<223> OTHER INFORMATION: PCR primer

<400> SEQUENCE: 9
tcgatgtgtg ctcagtaact gtaa        24

<210> SEQ ID NO 10
<211> LENGTH: 75
<212> TYPE: DNA
<213> ORGANISM: Artificial
<220> FEATURE:
<223> OTHER INFORMATION: PCR primer

<400> SEQUENCE: 10
ggttcagctg gtgcagtctg gagctgaagt gaagaagcct ggggcttcag tgaaggtgtc        60
ctgtaaggct tctgg        75

<210> SEQ ID NO 11
<211> LENGTH: 52
<212> TYPE: DNA
<213> ORGANISM: Artificial
<220> FEATURE:
<223> OTHER INFORMATION: PCR primer

<400> SEQUENCE: 11
agctgggtga ggcaggcacc tggacagggc cttgagtgga tgggagagat tt        52

<210> SEQ ID NO 12
<211> LENGTH: 60
<212> TYPE: DNA
<213> ORGANISM: Artificial
<220> FEATURE:
<223> OTHER INFORMATION: PCR primer

<400> SEQUENCE: 12
caagggcagg gtcacaatga ctagagacac atccaccagc acagtctaca tggaactcag        60

<210> SEQ ID NO 13
<211> LENGTH: 43
<212> TYPE: DNA
<213> ORGANISM: Artificial
<220> FEATURE:
<223> OTHER INFORMATION: PCR primer

<400> SEQUENCE: 13
cagcctgagg tctgaggaca ctgcggtcta ttactgtgca aga                              43

<210> SEQ ID NO 14
<211> LENGTH: 24
<212> TYPE: DNA
<213> ORGANISM: Artificial
<220> FEATURE:
<223> OTHER INFORMATION: PCR primer

<400> SEQUENCE: 14
gccaagggac actagtcact gtgt                                                   24

<210> SEQ ID NO 15
<211> LENGTH: 39
<212> TYPE: DNA
<213> ORGANISM: Artificial
<220> FEATURE:
<223> OTHER INFORMATION: PCR primer

<400> SEQUENCE: 15
actctaacca tggaatggat ctggatcttt ctcctcatc                                   39

<210> SEQ ID NO 16
<211> LENGTH: 39
<212> TYPE: DNA
<213> ORGANISM: Artificial
<220> FEATURE:
<223> OTHER INFORMATION: PCR primer

<400> SEQUENCE: 16
tcactgccta tgttataagc tgggtgaggc aggcacctg                                   39

<210> SEQ ID NO 17
<211> LENGTH: 21
<212> TYPE: DNA
<213> ORGANISM: Artificial
<220> FEATURE:
<223> OTHER INFORMATION: PCR primer

<400> SEQUENCE: 17
actagtcaca gtctcctcag c                                                      21

<210> SEQ ID NO 18
<211> LENGTH: 22
<212> TYPE: DNA
<213> ORGANISM: Artificial
<220> FEATURE:
<223> OTHER INFORMATION: PCR primer

<400> SEQUENCE: 18
gaattcattt acccggagac ag                                                     22

<210> SEQ ID NO 19
<211> LENGTH: 49
<212> TYPE: DNA
<213> ORGANISM: Artificial
<220> FEATURE:
<223> OTHER INFORMATION: PCR primer

<400> SEQUENCE: 19
ccgtgcccag cacctgaact cgcggggca ccgtcagtct tcctcccccc                        49

<210> SEQ ID NO 20

```
<211> LENGTH: 26
<212> TYPE: DNA
<213> ORGANISM: Artificial
<220> FEATURE:
<223> OTHER INFORMATION: PCR primer

<400> SEQUENCE: 20
ggtaccaagg tggaaatcaa acgaac                                              26

<210> SEQ ID NO 21
<211> LENGTH: 25
<212> TYPE: DNA
<213> ORGANISM: Artificial
<220> FEATURE:
<223> OTHER INFORMATION: PCR primer

<400> SEQUENCE: 21
aagcttctaa cactctcccc tgttg                                               25

<210> SEQ ID NO 22
<211> LENGTH: 78
<212> TYPE: DNA
<213> ORGANISM: Artificial
<220> FEATURE:
<223> OTHER INFORMATION: PCR primer

<400> SEQUENCE: 22
aagcttatgg aatggatctg gatctttctc ctcatcctgt caggaactcg aggtgtccag         60
tcccaggttc agctggtg                                                       78

<210> SEQ ID NO 23
<211> LENGTH: 74
<212> TYPE: DNA
<213> ORGANISM: Artificial
<220> FEATURE:
<223> OTHER INFORMATION: PCR primer

<400> SEQUENCE: 23
ctgtaaggct tctggataca cattcactgc ctatgttata agctgggtga ggcaggcacc         60
tggacagggc cttg                                                           74

<210> SEQ ID NO 24
<211> LENGTH: 70
<212> TYPE: DNA
<213> ORGANISM: Artificial
<220> FEATURE:
<223> OTHER INFORMATION: PCR primer

<400> SEQUENCE: 24
ggtagtagtt attataatga gaagttcaag ggcagggtca caatgactag agacacatcc         60
accagcacag                                                                70

<210> SEQ ID NO 25
<211> LENGTH: 77
<212> TYPE: DNA
<213> ORGANISM: Artificial
<220> FEATURE:
<223> OTHER INFORMATION: PCR primer

<400> SEQUENCE: 25
gaggacactg cggtctatta ctgtgcaaga tccggggacg gcagtcggtt tgtttactgg         60
ggccaaggga cactagt                                                        77
```

```
<210> SEQ ID NO 26
<211> LENGTH: 90
<212> TYPE: DNA
<213> ORGANISM: Artificial
<220> FEATURE:
<223> OTHER INFORMATION: PCR primer

<400> SEQUENCE: 26
gtgtatccag aagccttaca ggacaccttc actgaagccc caggcttctt cacttcagct      60
ccagactgca ccagctgaac ctgggactgg                                       90

<210> SEQ ID NO 27
<211> LENGTH: 77
<212> TYPE: DNA
<213> ORGANISM: Artificial
<220> FEATURE:
<223> OTHER INFORMATION: PCR primer

<400> SEQUENCE: 27
cttctcatta taataactac taccgcttcc aggataaatc tctcccatcc actcaaggcc      60
ctgtccaggt gcctgcc                                                     77

<210> SEQ ID NO 28
<211> LENGTH: 71
<212> TYPE: DNA
<213> ORGANISM: Artificial
<220> FEATURE:
<223> OTHER INFORMATION: PCR primer

<400> SEQUENCE: 28
gtaatagacc gcagtgtcct cagacctcag gctgctgagt tccatgtaga ctgtgctggt      60
ggatgtgtct c                                                           71

<210> SEQ ID NO 29
<211> LENGTH: 69
<212> TYPE: DNA
<213> ORGANISM: Artificial
<220> FEATURE:
<223> OTHER INFORMATION: PCR primer

<400> SEQUENCE: 29
gaattcatgg agacagacac aatcctgcta tgggtgctgc tgctctgggt tccaggctcc      60
actggtgac                                                              69

<210> SEQ ID NO 30
<211> LENGTH: 66
<212> TYPE: DNA
<213> ORGANISM: Artificial
<220> FEATURE:
<223> OTHER INFORMATION: PCR primer

<400> SEQUENCE: 30
ggctgtgtct ctaggtgaga gggccaccat caactgcaag gccagccaaa gtgttgatta      60
tgatgg                                                                 66

<210> SEQ ID NO 31
<211> LENGTH: 65
<212> TYPE: DNA
<213> ORGANISM: Artificial
<220> FEATURE:
<223> OTHER INFORMATION: PCR primer

<400> SEQUENCE: 31
```
cagaaaccag gacagccacc caaactcctc atctatgttg catccaatct agagtctggg    60
gtccc    65

<210> SEQ ID NO 32
<211> LENGTH: 66
<212> TYPE: DNA
<213> ORGANISM: Artificial
<220> FEATURE:
<223> OTHER INFORMATION: PCR primer

<400> SEQUENCE: 32
ggacagactt caccctcacc atcagttctc tgcaggcgga ggatgttgca gtctattact    60
gtcagc    66

<210> SEQ ID NO 33
<211> LENGTH: 67
<212> TYPE: DNA
<213> ORGANISM: Artificial
<220> FEATURE:
<223> OTHER INFORMATION: PCR primer

<400> SEQUENCE: 33
cacctagaga cacagccaaa gaatctggag attgggtcat cacaatgtca ccagtggagc    60
ctggaac    67

<210> SEQ ID NO 34
<211> LENGTH: 66
<212> TYPE: DNA
<213> ORGANISM: Artificial
<220> FEATURE:
<223> OTHER INFORMATION: PCR primer

<400> SEQUENCE: 34
ggtggctgtc ctggtttctg ttgataccag ttcatataac tatcaccatc ataatcaaca    60
ctttgg    66

<210> SEQ ID NO 35
<211> LENGTH: 67
<212> TYPE: DNA
<213> ORGANISM: Artificial
<220> FEATURE:
<223> OTHER INFORMATION: PCR primer

<400> SEQUENCE: 35
ggtgagggtg aagtctgtcc cagacccact gccactaaac ctgtctggga ccccagactc    60
tagattg    67

<210> SEQ ID NO 36
<211> LENGTH: 60
<212> TYPE: DNA
<213> ORGANISM: Artificial
<220> FEATURE:
<223> OTHER INFORMATION: PCR primer

<400> SEQUENCE: 36
ggtacctcca ccgaacgtcg gagggtcctg aagactttgc tgacagtaat agactgcaac    60

<210> SEQ ID NO 37
<211> LENGTH: 717
<212> TYPE: DNA
<213> ORGANISM: Artificial
<220> FEATURE:
<223> OTHER INFORMATION: DNA Sequence encoding light chain of humanzied antibody

<400> SEQUENCE: 37

```
atggagacag acacaatcct gctatgggtg ctgctgctct ggttccagg ctccactggt    60
gacattgtga tgacccaatc tccagattct ttggctgtgt ctctaggtga gagggccacc   120
atcaactgca aggccagcca aagtgttgat tatgatggtg atagttatat gaactggtat   180
caacagaaac aggacagcc acccaaactc ctcatctatg ttgcatccaa tctagagtct   240
ggggtcccag acaggtttag tggcagtggg tctgggacag acttcaccct caccatcagt   300
tctctgcagg cggaggatgt tgcagtctat tactgtcagc aaagtcttca ggaccctccg   360
acgttcggtg gaggtaccaa ggtggaaatc aaacgaactg tggctgcacc atctgtcttc   420
atcttcccgc catctgatga gcagttgaaa tctggaactg cctctgttgt gtgcctgctg   480
aataacttct atcccagaga ggccaaagta cagtggaagg tggataacgc cctccaatcg   540
ggtaactccc aggagagtgt cacagagcag gacagcaagg acagcaccta cagcctcagc   600
agcaccctga cgctgagcaa agcagactac gagaaacaca agtctacgc ctgcgaagtc   660
acccatcagg gcctgagctc gcccgtcaca aagagcttca cagggagag tgttag        717
```

<210> SEQ ID NO 38
<211> LENGTH: 238
<212> TYPE: PRT
<213> ORGANISM: Artificial
<220> FEATURE:
<223> OTHER INFORMATION: Light chain of humanized antibody

<400> SEQUENCE: 38

```
Met Glu Thr Asp Thr Ile Leu Leu Trp Val Leu Leu Leu Trp Val Pro
1               5                   10                  15

Gly Ser Thr Gly Asp Ile Val Met Thr Gln Ser Pro Asp Ser Leu Ala
            20                  25                  30

Val Ser Leu Gly Glu Arg Ala Thr Ile Asn Cys Lys Ala Ser Gln Ser
        35                  40                  45

Val Asp Tyr Asp Gly Asp Ser Tyr Met Asn Trp Tyr Gln Gln Lys Pro
    50                  55                  60

Gly Gln Pro Pro Lys Leu Leu Ile Tyr Val Ala Ser Asn Leu Glu Ser
65                  70                  75                  80

Gly Val Pro Asp Arg Phe Ser Gly Ser Gly Ser Gly Thr Asp Phe Thr
                85                  90                  95

Leu Thr Ile Ser Ser Leu Gln Ala Glu Asp Val Ala Val Tyr Tyr Cys
            100                 105                 110

Gln Gln Ser Leu Gln Asp Pro Pro Thr Phe Gly Gly Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220
```

Leu Ser Ser Pro Val Thr Lys Ser Phe Asn Arg Gly Glu Cys
225                 230                 235

<210> SEQ ID NO 39
<211> LENGTH: 218
<212> TYPE: PRT
<213> ORGANISM: Artificial
<220> FEATURE:
<223> OTHER INFORMATION: Light chain of humanized antibody

<400> SEQUENCE: 39

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Val Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Leu
                85                  90                  95

Gln Asp Pro Pro Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 40
<211> LENGTH: 1404
<212> TYPE: DNA
<213> ORGANISM: Artificial
<220> FEATURE:
<223> OTHER INFORMATION: DNA encoding heavy chain of humanzied antibody

<400> SEQUENCE: 40
atggaatgga tctggatctt tctcctcatc ctgtcaggaa ctcgaggtgt ccagtcccag    60
gttcagctgg tgcagtctgg agctgaagtg aagaagcctg ggcttcagt gaaggtgtcc    120 tgtaaggctt ctggatacac attcactgcc tatgttataa gctgggtgag gcaggcacct   180
ggacagggcc ttgagtggat gggagagatt tatcctggaa gcgtagtag ttattataat    240 gagaagttca agggcagggt cacaatgact agagacacat ccaccagcac agtctacatg   300
gaactcagca gcctgaggtc tgaggacact gcggtctatt actgtgcaag atccggggac   360
ggcagtcggt ttgtttactg gggccaaggg acactagtca cagtctcctc agcctccacc   420

-continued

```
aagggcccat cggtcttccc cctggcaccc tcctccaaga gcacctctgg gggcacagcg    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga agttgagcc caaatcttgt    720 gacaaaactc acacatgccc accgtgccca gcacctgaac tcgcggggc accgtcagtc     780 ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggatga gctgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta cagcaagctc accgtggaca agagcaggtg gcagcagggg   1320
aacgtcttct catgctccgt gatgcatgag gctctgcaca accactacac gcagaagagc   1380
ctctccctgt ctccgggtaa atga                                          1404
```

<210> SEQ ID NO 41
<211> LENGTH: 467
<212> TYPE: PRT
<213> ORGANISM: Artificial
<220> FEATURE:
<223> OTHER INFORMATION: Heavy chain of humanized antibody

<400> SEQUENCE: 41

```
Met Glu Trp Ile Trp Ile Phe Leu Leu Ile Leu Ser Gly Thr Arg Gly
1               5                   10                  15

Val Gln Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ala Tyr Val Ile Ser Trp Val Arg Gln Ala Pro Gly Gln Gly Leu
    50                  55                  60

Glu Trp Met Gly Glu Ile Tyr Pro Gly Ser Gly Ser Ser Tyr Tyr Asn
65                  70                  75                  80

Glu Lys Phe Lys Gly Arg Val Thr Met Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Ser Gly Asp Gly Ser Arg Phe Val Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
```

-continued

```
                180                 185                 190
Val Leu Gln Ser Ser Gly Leu Tyr Ser Leu Ser Val Val Thr Val
                195                 200                 205
Pro Ser Ser Ser Leu Gly Thr Gln Thr Tyr Ile Cys Asn Val Asn His
        210                 215                 220
Lys Pro Ser Asn Thr Lys Val Asp Lys Val Glu Pro Lys Ser Cys
225                 230                 235                 240
Asp Lys Thr His Thr Cys Pro Pro Cys Pro Ala Pro Glu Leu Leu Gly
                245                 250                 255
Gly Pro Ser Val Phe Leu Phe Pro Pro Lys Pro Lys Asp Thr Leu Met
            260                 265                 270
Ile Ser Arg Thr Pro Glu Val Thr Cys Val Val Val Asp Val Ser His
            275                 280                 285
Glu Asp Pro Glu Val Lys Phe Asn Trp Tyr Val Asp Gly Val Glu Val
            290                 295                 300
His Asn Ala Lys Thr Lys Pro Arg Glu Glu Gln Tyr Ala Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
                340                 345                 350
Glu Lys Thr Ile Ser Lys Ala Lys Gly Gln Pro Arg Glu Pro Gln Val
            355                 360                 365
Tyr Thr Leu Pro Pro Ser Arg Asp Glu Leu Thr Lys Asn Gln Val Ser
        370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
            435                 440                 445
His Glu Ala Leu His Asn His Tyr Thr Gln Lys Ser Leu Ser Leu Ser
    450                 455                 460
Pro Gly Lys
465

<210> SEQ ID NO 42
<211> LENGTH: 448
<212> TYPE: PRT
<213> ORGANISM: Artificial
<220> FEATURE:
<223> OTHER INFORMATION: Heavy chain of humanized antibody

<400> SEQUENCE: 42

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ala Tyr
                20                  25                  30
Val Ile Ser Trp Val Arg Gln Ala Pro Gly Gln Gly Leu Glu Trp Met
            35                  40                  45
Gly Glu Ile Tyr Pro Gly Ser Gly Ser Tyr Tyr Asn Glu Lys Phe
        50                  55                  60
Lys Gly Arg Val Thr Met Thr Arg Asp Thr Ser Thr Ser Thr Val Tyr
```

```
                65                  70                  75                  80
Met Glu Leu Ser Ser Leu Arg Ser Glu Asp Thr Ala Val Tyr Tyr Cys
                        85                  90                  95

Ala Arg Ser Gly Asp Gly Ser Arg Phe Val Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 43
<211> LENGTH: 717
<212> TYPE: DNA
<213> ORGANISM: Artificial
<220> FEATURE:
<223> OTHER INFORMATION: DNA encoding light chain of humanized antibody
```

<400> SEQUENCE: 43

```
atggagacag acacaatcct gctatgggtg ctgctgctct gggttccagg ctccactggt      60
gacattgtga tgacccaatc tccagattct ttggctgtgt ctctaggtga gagggccacc     120
atcaactgca aggccagcca aagtgttgat tatgatggtg atagttatat gaactggtat     180
caacagaaac caggacagcc acccaaactc ctcatctatg ttgcatccaa tctagagtct     240
ggggtcccag acaggtttag tggcagtggg tctgggacag acttcaccct caccatcagt     300
tctctgcagg cggaggatgt tgcagtctat tactgtcagc aaagtcttca ggaccctccg     360
acgttcggtg gaggtaccaa ggtggaaatc aaacgaactg tggctgcact atctgtcttc     420
atcttcccgc catctgatga gcagttgaaa tctggaactg cctctgttgt gtgcctgctg     480
aataacttct atcccagaga ggccaaagta cagtggaagg tggataacgc cctccaatcg     540
ggtaactccc aggagagtgt cacagagcag gacagcaagg acagcaccta cagcctcagc     600
agcaccctga cgctgagcaa agcagactac gagaaacaca agtctacgc ctgcgaagtc      660
acccatcagg gcctgagctc gcccgtcaca aagagcttca acaggggaga gtgttag       717
```

<210> SEQ ID NO 44
<211> LENGTH: 238
<212> TYPE: PRT
<213> ORGANISM: Artificial
<220> FEATURE:
<223> OTHER INFORMATION: Light chain of humanized antibody

<400> SEQUENCE: 44

```
Met Glu Thr Asp Thr Ile Leu Leu Trp Val Leu Leu Leu Trp Val Pro
1               5                   10                  15

Gly Ser Thr Gly Asp Ile Val Met Thr Gln Ser Pro Asp Ser Leu Ala
            20                  25                  30

Val Ser Leu Gly Glu Arg Ala Thr Ile Asn Cys Lys Ala Ser Gln Ser
        35                  40                  45

Val Asp Tyr Asp Gly Asp Ser Tyr Met Asn Trp Tyr Gln Gln Lys Pro
    50                  55                  60

Gly Gln Pro Pro Lys Leu Leu Ile Tyr Val Ala Ser Asn Leu Glu Ser
65                  70                  75                  80

Gly Val Pro Asp Arg Phe Ser Gly Ser Gly Ser Gly Thr Asp Phe Thr
                85                  90                  95

Leu Thr Ile Ser Ser Leu Gln Ala Glu Asp Val Ala Val Tyr Tyr Cys
            100                 105                 110

Gln Gln Ser Leu Gln Asp Pro Pro Thr Phe Gly Gly Gly Thr Lys Val
        115                 120                 125

Glu Ile Lys Arg Thr Val Ala Ala Leu Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
```

<210> SEQ ID NO 45
<211> LENGTH: 218
<212> TYPE: PRT
<213> ORGANISM: Artificial
<220> FEATURE:
<223> OTHER INFORMATION: Light chain of humanized antibody

<400> SEQUENCE: 45

```
Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Val Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Leu
                85                  90                  95

Gln Asp Pro Pro Thr Phe Gly Gly Gly Thr Lys Val Glu Ile Lys Arg
            100                 105                 110

Thr Val Ala Ala Leu Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 46
<211> LENGTH: 1404
<212> TYPE: DNA
<213> ORGANISM: Artificial
<220> FEATURE:
<223> OTHER INFORMATION: DNA sequence encoding heavy chain of humanized antibody

<400> SEQUENCE: 46

```
atggaatgga tctggatctt tctcctcatc ctgtcaggaa ctcgaggtgt ccagtcccag    60
gttcagctgg tgcagtctgg agctgaagtg aagaagcctg ggcttcagt gaaggtgtcc    120 tgtaaggctt ctggatacac attcactgcc tatgttataa gctgggtgag gcaggcacct    180
ggacagggcc ttgagtggat gggagagatt tatcctggaa gcgtagtag ttattataat    240 gagaagttca aggcagggt cacaatgact agagacacat ccaccagcac agtctacatg    300
gaactcagca gcctgaggtc tgaggacact gcggtctatt actgtgcaag atccggggac    360
ggcagtcggt tgtttactg gggccaaggg acactagtca cagtctcctc agcctccacc    420
```

```
aagggcccat cggtcttccc cctggcaccc tcctccaaga gcacctctgg gggcacagcg    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga agttgagcc caaatcttgt     720
gacaaaactc acacatgccc accgtgccca gcacctgaac tcctgggggg accgtcagtc    780
ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacgc cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggatga gctgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta cagcaagctc accgtggaca agagcaggtg gcagcagggg   1320
aacgtcttct catgctccgt gatgcatgag gctctgcaca accactacac gcagaagagc   1380
ctctccctgt ctccgggtaa atga                                          1404
```

<210> SEQ ID NO 47
<211> LENGTH: 467
<212> TYPE: PRT
<213> ORGANISM: Artificial
<220> FEATURE:
<223> OTHER INFORMATION: Heavy chain of humanized antibody

<400> SEQUENCE: 47

```
Met Glu Trp Ile Trp Ile Phe Leu Leu Ile Leu Ser Gly Thr Arg Gly
1               5                   10                  15

Val Gln Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ala Tyr Val Ile Ser Trp Val Arg Gln Ala Pro Gly Gln Gly Leu
    50                  55                  60

Glu Trp Met Gly Glu Ile Tyr Pro Gly Ser Gly Ser Ser Tyr Tyr Asn
65                  70                  75                  80

Glu Lys Phe Lys Gly Arg Val Thr Met Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Ser Gly Asp Gly Ser Arg Phe Val Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190
```

```
Val Leu Gln Ser Ser Gly Leu Tyr Ser Leu Ser Ser Val Val Thr Val
            195                 200                 205

Pro Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Ala Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 48
<211> LENGTH: 448
<212> TYPE: PRT
<213> ORGANISM: Artificial
<220> FEATURE:
<223> OTHER INFORMATION: Heavy chain of humanized antibody

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Tyr
            20                  25                  30

Val Ile Ser Trp Val Arg Gln Ala Pro Gly Gln Gly Leu Glu Trp Met
        35                  40                  45

Gly Glu Ile Tyr Pro Gly Ser Gly Ser Tyr Tyr Asn Glu Lys Phe
    50                  55                  60

Lys Gly Arg Val Thr Met Thr Arg Asp Thr Ser Thr Ser Thr Val Tyr
65                  70                  75                  80
```

```
Met Glu Leu Ser Ser Leu Arg Ser Glu Asp Thr Ala Val Tyr Tyr Cys
                85                  90                  95

Ala Arg Ser Gly Asp Gly Ser Arg Phe Val Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 49
<211> LENGTH: 717
<212> TYPE: DNA
<213> ORGANISM: Artificial
<220> FEATURE:
<223> OTHER INFORMATION: DNA sequence encoding light chain of humanized
      antibody
```

<400> SEQUENCE: 49

```
atggagacag acacaatcct gctatgggtg ctgctgctct gggttccagg ctccactggt      60
gacattgtga tgacccaatc tccagattct ttggctgtgt ctctaggtga gagggccacc     120
atcaactgca aggccagcca aagtgttgat tatgatggtg atagttatat gaactggtat     180
caacagaaac caggacagcc acccaaactc ctcatctatg ttgcatccaa tctagagtct     240
ggggtcccag acaggtttag tggcagtggg tctgggacag acttcaccct caccatcagt     300
tctctgcagg cggaggatgt tgcagtctat tactgtcagc aaagtcttca ggaccctccg     360
acgttcggtg aggtaccaa ggtggaaatc aaacgaactg tggctgcact atctgtcttc     420
atcttcccgc catctgatga gcagttgaaa tctggaactg cctctgttgt gtgcctgctg     480
aataacttct atcccagaga ggccaaagta cagtggaagg tggataacgc cctccaatcg     540
ggtaactccc aggagagtgt cacagagcag gacagcaagg acagcaccta cagcctcagc     600
agcaccctga cgctgagcaa agcagactac gagaaacaca agtctacgc ctgcgaagtc     660
acccatcagg gcctgagctc gcccgtcaca aagagcttca cagggagag tgttag         717
```

<210> SEQ ID NO 50
<211> LENGTH: 238
<212> TYPE: PRT
<213> ORGANISM: Artificial
<220> FEATURE:
<223> OTHER INFORMATION: Light chain of humanized antibody

<400> SEQUENCE: 50

```
Met Glu Thr Asp Thr Ile Leu Leu Trp Val Leu Leu Leu Trp Val Pro
  1               5                  10                  15

Gly Ser Thr Gly Asp Ile Val Met Thr Gln Ser Pro Asp Ser Leu Ala
             20                  25                  30

Val Ser Leu Gly Glu Arg Ala Thr Ile Asn Cys Lys Ala Ser Gln Ser
         35                  40                  45

Val Asp Tyr Asp Gly Asp Ser Tyr Met Asn Trp Tyr Gln Gln Lys Pro
     50                  55                  60

Gly Gln Pro Pro Lys Leu Leu Ile Tyr Val Ala Ser Asn Leu Glu Ser
 65                  70                  75                  80

Gly Val Pro Asp Arg Phe Ser Gly Ser Gly Ser Gly Thr Asp Phe Thr
                 85                  90                  95

Leu Thr Ile Ser Ser Leu Gln Ala Glu Asp Val Ala Val Tyr Tyr Cys
            100                 105                 110

Gln Gln Ser Leu Gln Asp Pro Pro Thr Phe Gly Gly Gly Thr Lys Val
        115                 120                 125

Glu Ile Lys Arg Thr Val Ala Ala Leu Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
```

<210> SEQ ID NO 51
<211> LENGTH: 218
<212> TYPE: PRT
<213> ORGANISM: Artificial
<220> FEATURE:
<223> OTHER INFORMATION: Light chain of humanized antibody

<400> SEQUENCE: 51

```
Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Val Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Leu
                85                  90                  95

Gln Asp Pro Pro Thr Phe Gly Gly Gly Thr Lys Val Glu Ile Lys Arg
            100                 105                 110

Thr Val Ala Ala Leu Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 52
<211> LENGTH: 1404
<212> TYPE: DNA
<213> ORGANISM: Artificial
<220> FEATURE:
<223> OTHER INFORMATION: DNA encoding heavy chain of humanized antibody

<400> SEQUENCE: 52

```
atggaatgga tctggatctt tctcctcatc ctgtcaggaa ctcgaggtgt ccagtcccag      60
gttcagctgg tgcagtctgg agctgaagtg aagaagcctg ggcttcagt gaaggtgtcc     120 tgtaaggctt ctggatacac attcactgcc tatgttataa ctgggtgag gcaggcacct     180 ggacagggcc ttgagtggat gggagagatt tatcctggaa gcggtagtag ttattataat    240
gagaagttca gggcagggt cacaatgact agagacacat ccaccagcac agtctacatg     300
gaactcagca gcctgaggtc tgaggacact gcggtctatt actgtgcaag atccggggac    360
ggcagtcggt tgtttactg gggccaaggg acactagtca cagtctcctc agcctccacc     420
aagggcccat cggtcttccc cctggcaccc tcctccaaga gcacctctgg gggcacagcg    480
```

```
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga agttgagccc aaatcttgt     720 gacaaaactc acacatgccc accgtgccca gcacctgaac tcgcggggc accgtcagtc     780 ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaccatctc caaagccaaa    1080 gggcagcccc gagaaccaca ggtgtacacc ctgcccccat cccgggatga gctgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta cagcaagctc accgtggaca agagcaggtg gcagcagggg   1320
aacgtcttct catgctccgt gatgcatgag gctctgcaca accactacac gcagaagagc   1380
ctctccctgt ctccgggtaa atga                                          1404
```

<210> SEQ ID NO 53
<211> LENGTH: 467
<212> TYPE: PRT
<213> ORGANISM: Artificial
<220> FEATURE:
<223> OTHER INFORMATION: Heavy chain of humanized antibody

<400> SEQUENCE: 53

```
Met Glu Trp Ile Trp Ile Phe Leu Leu Ile Leu Ser Gly Thr Arg Gly
1               5                   10                  15

Val Gln Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ala Tyr Val Ile Ser Trp Val Arg Gln Ala Pro Gly Gln Gly Leu
    50                  55                  60

Glu Trp Met Gly Glu Ile Tyr Pro Gly Ser Gly Ser Ser Tyr Tyr Asn
65                  70                  75                  80

Glu Lys Phe Lys Gly Arg Val Thr Met Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Ser Gly Asp Gly Ser Arg Phe Val Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190
```

-continued

```
Val Leu Gln Ser Ser Gly Leu Tyr Ser Leu Ser Ser Val Val Thr Val
            195                 200                 205

Pro Ser Ser Leu Gly Thr Gln Thr Tyr Ile Cys Asn Val Asn His
210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Ala Gly
            245                 250                 255

Ala Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Asp Glu Leu Thr Lys Asn Gln Val Ser
            370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
            450                 455                 460

Pro Gly Lys
465
```

<210> SEQ ID NO 54
<211> LENGTH: 448
<212> TYPE: PRT
<213> ORGANISM: Artificial
<220> FEATURE:
<223> OTHER INFORMATION: Heavy chain of humanized antibody

<400> SEQUENCE: 54

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Tyr
            20                  25                  30

Val Ile Ser Trp Val Arg Gln Ala Pro Gly Gln Gly Leu Glu Trp Met
        35                  40                  45

Gly Glu Ile Tyr Pro Gly Ser Gly Ser Tyr Tyr Asn Glu Lys Phe
    50                  55                  60

Lys Gly Arg Val Thr Met Thr Arg Asp Thr Ser Thr Ser Thr Val Tyr
65                  70                  75                  80
```

```
Met Glu Leu Ser Ser Leu Arg Ser Glu Asp Thr Ala Val Tyr Tyr Cys
                85                  90                  95

Ala Arg Ser Gly Asp Gly Ser Arg Phe Val Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 55
<211> LENGTH: 717
<212> TYPE: DNA
<213> ORGANISM: Artificial
<220> FEATURE:
<223> OTHER INFORMATION: DNA encoding light chain of humanized antibody

<400> SEQUENCE: 55
```

```
atggagacag acacaatcct gctatgggtg ctgctgctct gggttccagg ctccactggt    60
gacattgtga tgacccaatc tccagattct ttggctgtgt ctctaggtga gagggccacc   120
atcaactgca aggccagcca aagtgttgat tatgatggtg atagttatat gaactggtat   180
caacagaaac aggacagcc acccaaactc ctcatctatg ttgcatccaa tctagagtct    240
ggggtcccag acaggtttag tggcagtggg tctgggacag acttcaccct caccatcagt   300
tctctgcagg cggaggatgt tgcagtctat tactgtcagc aaagtcttca ggaccctccg   360
acgttcggtg aggtaccaa ggtggaaatc aaacgaactg tggctgcacc atctgtcttc    420
atcttcccgc catctgatga gcagttgaaa tctggaactg cctctgttgt gtgcctgctg   480
aataacttct atcccagaga ggccaaagta cagtggaagg tggataacgc cctccaatcg   540
ggtaactccc aggagagtgt cacagagcag gacagcaagg acagcaccta cagcctcagc   600
agcaccctga cgctgagcaa agcagactac gagaaacaca agtctacgc ctgcgaagtc    660 acccatcagg gcctgagctc gcccgtcaca aagagcttca caggggaga gtgttag      717
```

<210> SEQ ID NO 56
<211> LENGTH: 238
<212> TYPE: PRT
<213> ORGANISM: Artificial
<220> FEATURE:
<223> OTHER INFORMATION: Light chain of humanized antibody

<400> SEQUENCE: 56

```
Met Glu Thr Asp Thr Ile Leu Leu Trp Val Leu Leu Leu Trp Val Pro
1               5                   10                  15

Gly Ser Thr Gly Asp Ile Val Met Thr Gln Ser Pro Asp Ser Leu Ala
            20                  25                  30

Val Ser Leu Gly Glu Arg Ala Thr Ile Asn Cys Lys Ala Ser Gln Ser
        35                  40                  45

Val Asp Tyr Asp Gly Asp Ser Tyr Met Asn Trp Tyr Gln Gln Lys Pro
    50                  55                  60

Gly Gln Pro Pro Lys Leu Leu Ile Tyr Val Ala Ser Asn Leu Glu Ser
65                  70                  75                  80

Gly Val Pro Asp Arg Phe Ser Gly Ser Gly Ser Gly Thr Asp Phe Thr
                85                  90                  95

Leu Thr Ile Ser Ser Leu Gln Ala Glu Asp Val Ala Val Tyr Tyr Cys
            100                 105                 110

Gln Gln Ser Leu Gln Asp Pro Pro Thr Phe Gly Gly Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

```
<210> SEQ ID NO 57
<211> LENGTH: 218
<212> TYPE: PRT
<213> ORGANISM: Artificial
<220> FEATURE:
<223> OTHER INFORMATION: Light chain of humanized antibody

<400> SEQUENCE: 57

Asp Ile Val Met Thr Gln Ser Pro Asp Ser Leu Ala Val Ser Leu Gly
 1               5                  10                  15

Glu Arg Ala Thr Ile Asn Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Val Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Leu
                85                  90                  95

Gln Asp Pro Pro Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 58
<211> LENGTH: 1404
<212> TYPE: DNA
<213> ORGANISM: Artificial
<220> FEATURE:
<223> OTHER INFORMATION: DNA encoding heavy chain of humanized antibody

<400> SEQUENCE: 58
atggaatgga tctggatctt tctcctcatc ctgtcaggaa ctcgaggtgt ccagtcccag     60
gttcagctgg tgcagtctgg agctgaagtg aagaagcctg ggcttcagt gaaggtgtcc    120 tgtaaggctt ctggatacac attcactgcc tatgttataa gctgggtgag gcaggcacct    180
ggacagggcc ttgagtggat gggagagatt tatcctggaa gcgtagtag ttattataat    240 gagaagttca agggcagggt cacaatgact agagacacat ccaccagcac agtctacatg    300
gaactcagca gcctgaggtc tgaggacact gcggtctatt actgtgcaag atccggggac    360
ggcagtcggt ttgtttactg gggccaaggg acactagtca cagtctcctc agcctccacc    420
aagggcccat cggtcttccc cctggcaccc tcctccaaga gcacctctgg ggcacagcg    480 gccctgggct gcctggtcaa ggactacttc cccgaaccgg tgacggtgtc gtggaactca    540
```

```
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga agttgagcc caaatcttgt     720 gacaaaactc acacatgccc accgtgccca gcacctgaac tcctgggggg accgtcagtc    780
ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacgc cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggatga gctgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta cagcaagctc accgtggaca agagcaggtg gcagcagggg   1320
aacgtcttct catgctccgt gatgcatgag gctctgcaca accactacac gcagaagagc   1380
ctctccctgt ctccgggtaa atga                                           1404
```

<210> SEQ ID NO 59
<211> LENGTH: 467
<212> TYPE: PRT
<213> ORGANISM: Artificial
<220> FEATURE:
<223> OTHER INFORMATION: Heavy chain of humanized antibody

<400> SEQUENCE: 59

```
Met Glu Trp Ile Trp Ile Phe Leu Leu Ile Leu Ser Gly Thr Arg Gly
1               5                   10                  15

Val Gln Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ala Tyr Val Ile Ser Trp Val Arg Gln Ala Pro Gly Gln Gly Leu
    50                  55                  60

Glu Trp Met Gly Glu Ile Tyr Pro Gly Ser Gly Ser Ser Tyr Tyr Asn
65                  70                  75                  80

Glu Lys Phe Lys Gly Arg Val Thr Met Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Ser Gly Asp Gly Ser Arg Phe Val Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205
```

```
Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Ala Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
450                 455                 460

Pro Gly Lys
465

<210> SEQ ID NO 60
<211> LENGTH: 448
<212> TYPE: PRT
<213> ORGANISM: Artificial
<220> FEATURE:
<223> OTHER INFORMATION: Heavy chain of humanized antibody

<400> SEQUENCE: 60

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Tyr
                20                  25                  30

Val Ile Ser Trp Val Arg Gln Ala Pro Gly Gln Gly Leu Glu Trp Met
            35                  40                  45

Gly Glu Ile Tyr Pro Gly Ser Gly Ser Tyr Tyr Asn Glu Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95
```

-continued

```
Ala Arg Ser Gly Asp Gly Ser Arg Phe Val Tyr Trp Gly Gln Gly Thr
            100                 105                 110
Leu Val Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
            130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                    165                 170                 175
Ser Ser Gly Leu Tyr Ser Leu Ser Ser Val Val Thr Val Pro Ser Ser
                    180                 185                 190
Ser Leu Gly Thr Gln Thr Tyr Ile Cys Asn Val Asn His Lys Pro Ser
                    195                 200                 205
Asn Thr Lys Val Asp Lys Lys Val Glu Pro Lys Ser Cys Asp Lys Thr
                    210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                    245                 250                 255
Thr Pro Glu Val Thr Cys Val Val Val Asp Val Ser His Glu Asp Pro
                    260                 265                 270
Glu Val Lys Phe Asn Trp Tyr Val Asp Gly Val Glu Val His Asn Ala
                    275                 280                 285
Lys Thr Lys Pro Arg Glu Glu Gln Tyr Ala Ser Thr Tyr Arg Val Val
                    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                    325                 330                 335
Ile Ser Lys Ala Lys Gly Gln Pro Arg Glu Pro Gln Val Tyr Thr Leu
                    340                 345                 350
Pro Pro Ser Arg Asp Glu Leu Thr Lys Asn Gln Val Ser Leu Thr Cys
                    355                 360                 365
Leu Val Lys Gly Phe Tyr Pro Ser Asp Ile Ala Val Glu Trp Glu Ser
                    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                    405                 410                 415
Arg Trp Gln Gln Gly Asn Val Phe Ser Cys Ser Val Met His Glu Ala
                    420                 425                 430
Leu His Asn His Tyr Thr Gln Lys Ser Leu Ser Leu Ser Pro Gly Lys
                    435                 440                 445
```